(12) United States Patent
Suzuki et al.

(10) Patent No.: US 8,588,364 B2
(45) Date of Patent: Nov. 19, 2013

(54) MEDICAL X-RAY APPARATUS

(75) Inventors: Masakazu Suzuki, Kyoto (JP); Hideki Yoshikawa, Kyoto (JP); Takahiro Yoshimura, Kyoto (JP); Makoto Honjo, Kyoto (JP)

(73) Assignee: J. Morita Manufacturing Corporation, Kyoto (JP)

(*) Notice: Subject to any disclaimer, the term of this patent is extended or adjusted under 35 U.S.C. 154(b) by 54 days.

(21) Appl. No.: 12/806,694

(22) Filed: Aug. 19, 2010

(65) Prior Publication Data

US 2011/0064188 A1    Mar. 17, 2011

(30) Foreign Application Priority Data

Aug. 19, 2009  (JP) ................................. 2009-190082
Dec. 28, 2009  (JP) ................................. 2009-297445

(51) Int. Cl.
  *A61B 6/14*    (2006.01)
(52) U.S. Cl.
  USPC .............................................. 378/40; 378/38
(58) Field of Classification Search
  USPC .......................................... 378/38, 39, 40, 95
  See application file for complete search history.

(56) References Cited

U.S. PATENT DOCUMENTS 5,214,686 A * 5/1993 Webber ............................ 378/38
6,256,364 B1 * 7/2001 Toth et al. ......................... 378/4
2004/0066877 A1  4/2004 Arai et al.
2006/0233301 A1 * 10/2006 Erhardt et al. .................. 378/38
2007/0092061 A1  4/2007 Razzano et al.
2009/0168966 A1 * 7/2009 Suzuki et al. ................. 378/116
2009/0323891 A1 * 12/2009 Borghese et al. ............... 378/38

FOREIGN PATENT DOCUMENTS

| EP | 1 457 155 A | 9/2004 |
|---|---|---|
| JP | 2787169 | 6/1998 |
| JP | 2824602 | 9/1998 |
| JP | 2002-17718 | 1/2002 |
| JP | 2007-29168 | 2/2007 |
| JP | 3919048 | 2/2007 |
| JP | 2008-284137 | 11/2008 |
| WO | WO 2008/092009 A | 7/2008 |

* cited by examiner

*Primary Examiner* — Glen Kao
(74) *Attorney, Agent, or Firm* — DLA Piper LLP (US)

(57) ABSTRACT

A medical X-ray apparatus comprising a supporting part for supporting an X-ray generator and a two-dimensional X-ray detector while interposing an object to be examined therebetween, a radiation area restricting part for restricting a radiation area of X-ray generated from the X-ray generator, and a scan driving part for scanning the object with the X-ray restricted by the radiation area restricting part as X-ray beam and for executing radiography. A direction intersecting with X-ray scan direction is defined as a height direction, the apparatus further comprises a radiation area setting part for setting at least one of both ends of width of the X-ray beam in the height direction at a desired position in accordance with the position of an interested area of the object; and the X-ray beam is irradiated only to the radiation area as set by the radiation area setting part with its beam width in height direction restricted by the radiation area restricting part.

20 Claims, 40 Drawing Sheets

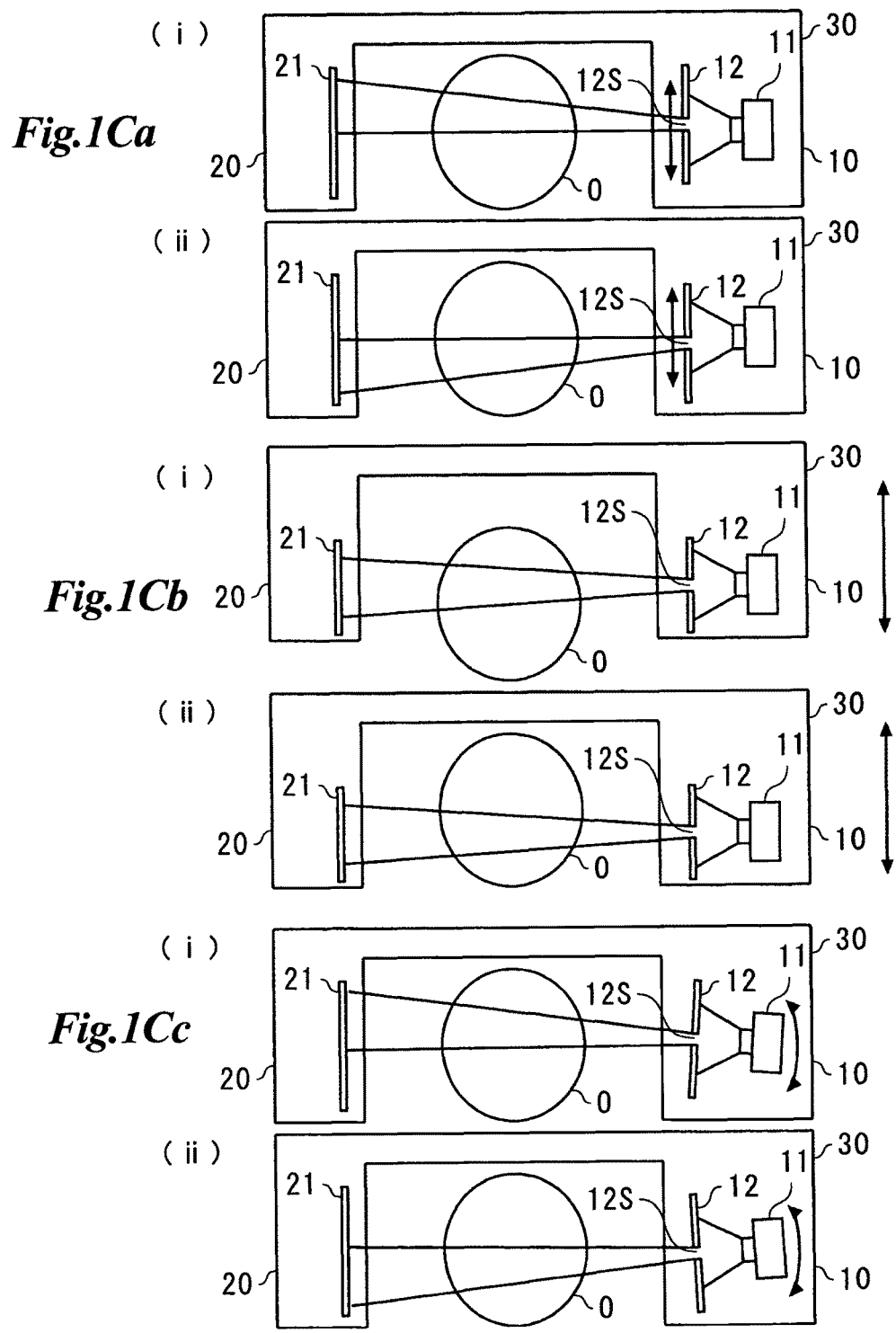

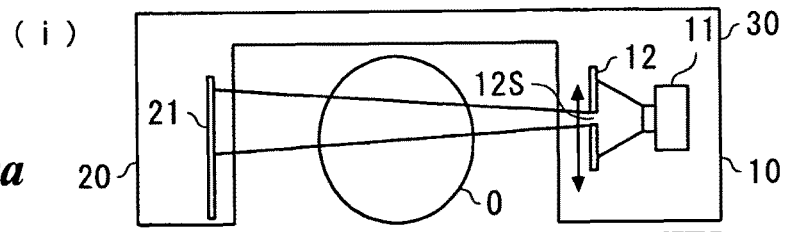
*Fig.1Da*
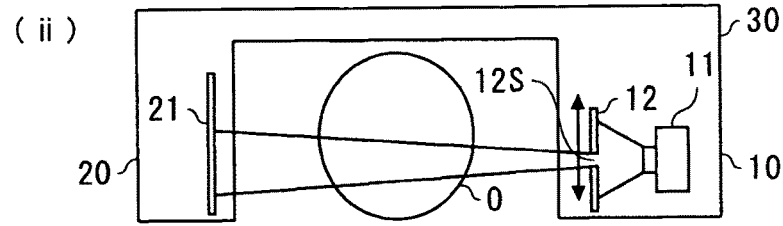
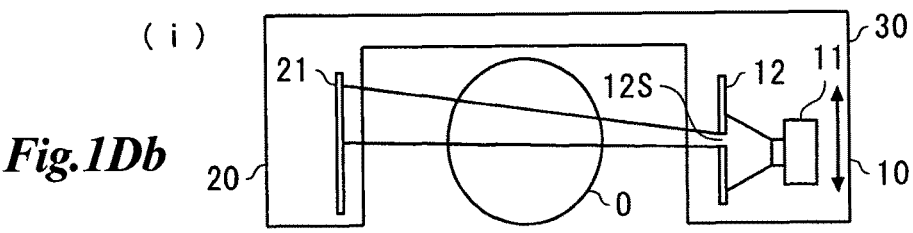
*Fig.1Db*
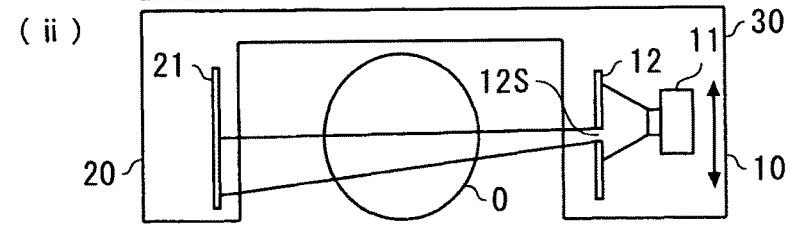
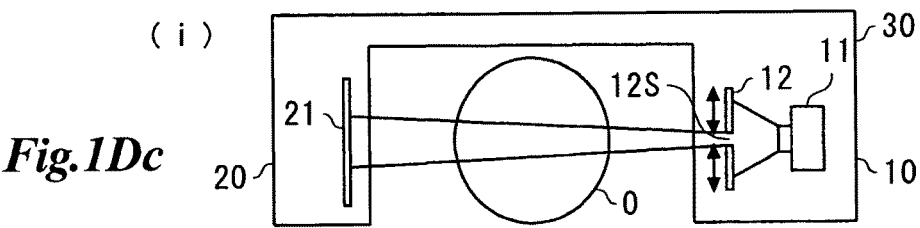
*Fig.1Dc*
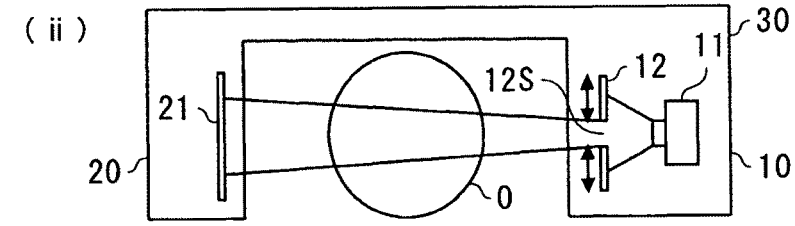

MEDICAL X-RAY APPARATUS

TECHNICAL FIELD

The present invention relates to a medical X-ray apparatus for obtaining the information on a curved sectional plane by X-ray projection and obtaining a two-dimensional panoramic X-ray image.

BACKGROUND ART

A medical X-ray apparatus has an X-ray generator for projecting X-ray and an X-ray detector for receiving the X-ray from the X-ray generator, receives the X-ray generated at the X-ray generator and transmitted through an object to be examined, thereby obtaining an X-ray transmitted image based on the transmitted X-ray amount. In case of panoramic radiography, X-ray is projected while the X-ray generator and the X-ray detector are moved around the object along a predetermined orbit and a two-dimensional panoramic X-ray image of a curved sectional plane is obtained.

The applicant of this invention has proposed a digital panoramic radiography apparatus in which the X-ray detector is a two-dimensional X-ray detector and a panoramic X-ray image on an optional sectional plane is produced from a plurality of frame images successively obtained from the two-dimensional X-ray detector (refer to patent citations 1 and 2). A sectional plane which has an equal distance from the detection surface of the X-ray detector which moves along a predetermined orbit is called as a "tubular sectional plane".

According to the digital panoramic radiography apparatus in the patent citations 1 and 2, a panoramic X-ray image is produced by combining a plurality of frame images obtained by panoramic radiography. In this case, a panoramic X-ray image on an optional sectional plane is produced by setting the fetch interval and the shift amount of the frame images which are used for calculation for producing a panoramic X-ray image. Specifically in the digital panoramic radiography apparatus in the patent citation 1, a panoramic X-ray image produced with the image information on the tubular sectional plane which is different from each area can be produced by changing the fetch interval and the shift amount of the frame images which are used for calculation for producing a panoramic X-ray image.

According to the digital, panoramic radiography apparatus in the patent citations 1 and 2, respectively, when a panoramic X-ray image is produced by adding the image data of a plurality of frame images, a panoramic X-ray image on an objective sectional plane can be produced when the fetch interval and the shift amount are set at an appropriate value. Specifically in the digital panoramic radiography apparatus in the patent citation 1, the facial direction of the sectional plane can be made optional when the image data on the tubular sectional plane which are selected to each area is combined on a sheet of panoramic X-ray image. In addition, according to a medical X-ray apparatus which executes panoramic radiography with a frame image like this digital panoramic radiography apparatus, the image data per the tubular sectional plane can be extracted from a plurality of frame images obtained by panoramic radiography with respect to an optional local region.

According to the panoramic imaging apparatus of the patent citation 3, the frame data obtained by panoramic radiography are synthesized to produce a panoramic X-ray image and a shutter for shielding X-ray is provided on the front surface of an X-ray tube to execute panoramic radiography only on a part of a dental arch. However, the patent citation 3 only discloses a structure for projecting X-ray on an object to be examined in a fixed distance during panoramic radiography on the entire dental arch. Namely, the patent citation 3 discloses that the X-ray radiation area is partially restricted along the scanning direction of X-ray beam.

The panoramic radiography apparatus in which electronic image data are obtained in a two-dimensional X-ray detector and a panoramic X-ray image is produced by an image process has been already proposed. In such a panoramic radiography apparatus like those in the patent citations 1 to 3, a plurality of frame images being X-ray transmitted images of a dental arch are rendered to shift operation to produce a panoramic X-ray image. Such production of panoramic X-ray image by the shift operation of the frame images has an advantage that a clear panoramic X-ray image is produced by synthesizing a sectional plane with plural planes in which a sectional plane on a desired position can be set.

The panoramic radiography apparatus in the patent citations 1 and 2 only proposes an idea that so called a panoramic sectional plane traverses longitudinally all over the dental arch and shift operation of frame image is executed based on the panoramic sectional plane of the entire dental arch. In addition, the panoramic radiography apparatus in the patent citation 2 discloses restriction of X-ray beam in a scanning direction, however, it does not disclose or suggest restriction of X-ray beam in a direction intersecting a scanning direction.

PRIOR ART CITATION

Patent Citation

PATENT CITATION 1 Japanese Patent No. 2787169B
PATENT CITATION 2 Japanese Patent No. 2824602B
PATENT CITATION 3 Japanese Patent Publication No. 2008-284137-A

DISCLOSURE OF INVENTION

Problem to be Solved in the Invention

Recently, a panoramic X-ray image only for a local region such as front teeth is sometimes required depending on process and content of medical treatment in a medical practice. However, in the digital panoramic X-ray apparatus disclosed in the patent citations 1 to 3, the region where data are not required becomes a radiography object. For example, in case that only the data for front teeth are required, X-ray is projected also on the region which is not directly required for diagnosis such as the region between the bone of the nose and the dental root end of the front teeth, so that a subject (patient) being an object to be examined is rendered to unnecessary exposure to X-ray. Further, it takes time for radiography, so a patient bears a great burden.

In view of such problems, in a medical X-ray apparatus wherein radiography is executed on a radiography region and a sectional image on an optional sectional plane on the radiography region is obtained, the present invention has an object to provide a medical X-ray apparatus which mainly improves reduction of exposure of the object to radiation.

Means to Solve the Problems

The medical X-ray apparatus proposed for the above-mentioned object comprises a supporting part for supporting an X-ray generator and a two-dimensional X-ray detector while interposing an object to be examined therebetween, a radiation area restricting part for restricting the radiation area of X-ray generated from the X-ray generator, and a scan driving part for scanning the object to be examined with the X-ray restricted by the radiation area restricting part as X-ray beam and for executing radiography, wherein a direction intersecting with X-ray scan direction is defined as a height direction. The apparatus further comprises a radiation area setting part for setting at least one of both ends of width of the X-ray beam in the height direction at a desired position in accordance with the position of an interested area of the object, and X-ray beam is irradiated only to the X-ray radiation area as set by the radiation area setting part with its beam width in height direction restricted by the radiation area restricting part.

The radiation area restricting part may further restrict the width of the X-ray beam in scan direction intersecting with in the height direction of the X-ray radiation area, or the radiation area setting part may change a position of at least one of both ends of the width of the X-ray beam in the height direction of the X-ray radiation area while the X-ray beam is scanned. At least one of the both ends of the X-ray beam width means one of the upper end and the lower end of the X-ray beam width and the X-ray radiation area is focused to be restricted in order to irradiate X-ray only on the minimum area required for diagnosis comparing to the prior art.

The applicant of the present invention also proposes the following inventions in order to achieve the above-mentioned problems.

The medical X-ray apparatus further comprises an object holding part for holding the object, and a moving mechanism for moving the supporting part at least in the height direction with respect to the object held with the object holding part, and the supporting part is driven for changing the X-ray beam in the height direction for the area set by the radiation area setting part in conformity with the corresponding part of the interested area of the object.

The medical X-ray apparatus further comprises a driving mechanism for driving the radiation area restricting part. The radiation area restricting part comprises an open part having an opening through which the X-ray beam generated at the X-ray generator passes, and the driving mechanism actuates the radiation area restricting part to change the position of at least one of both ends of the width of the opening in the height direction for the area set by said radiation area setting part in conformity with the corresponding part of the interested area of the object.

The open part comprises a slit member having a slit extending in the height direction and restricting the X-ray beam in slit-like form and a shielding member for restricting at least one end and the other end in the height direction of the slit for varying shielding amount, and the open part is constituted and disposed in front of the X-ray generator by combination of the slit member and the shielding member.

The radiography executed by the scan driving part is X-ray tomography, the radiation area setting part is adapted to set an X-ray tomography objective area as a radiography objective area, whereby only a part of the X-ray tomography objective area may be set as a radiation area for partial X-ray tomography.

The X-ray beam is X-ray slit beam restricted by the radiation area restricting part, the radiography is panoramic radiography in which the X-ray slit beam is irradiated on the object for scanning, the radiation area setting part is adapted to set a panoramic radiography objective area as the X-ray tomography objective area, whereby only a part of the panoramic radiography objective area may be set as a radiation area for partial panoramic radiography for the partial X-ray tomography.

The radiation area setting part may set as the X-ray radiation area for partial panoramic radiography only a tooth on an upper jaw or a tooth on a lower jaw as selected from an dental arch as used for the panoramic radiography objective area.

The X-ray generator may irradiate the X-ray beam to the X-ray radiation area only while the X-ray beam should pass through the radiation area for partial panoramic radiography.

The medical X-ray apparatus further comprises an X-ray generation controlling means for controlling a tube voltage and a tube current of the X-ray generator, when the panoramic radiography including the partial panoramic radiography is executed, the X-ray generation controlling means controls at least one of the tube voltage and the tube current of the X-ray generator in conformity with the area of the object where the X-ray beam is irradiated on the object from the X-ray generator.

The radiography may be cephalometric radiography in which X-ray slit beam restricted by the radiation area restricting part is irradiated to the object for scanning.

The medical X-ray apparatus may further comprise a camera for taking a picture of the object, wherein the radiation area setting part sets the X-ray radiation area of the object based on the picture of the object taken by the camera.

The medical X-ray apparatus may further comprise an image processing par for producing an X-ray tomography image of the X-ray radiation area of the partial X-ray tomography in such a manner that X-ray transmitted images with respect to the object detected on the two-dimensional X-ray detector are synthesized together to produce image data in a predetermined section of the object, when the partial X-ray tomography is executed setting only a part of the X-ray tomography objective area as the radiographic objective area.

The medical X-ray apparatus may further comprises an image processing means for producing a partial panoramic X-ray image of the X-ray radiation area of the partial panoramic radiography in such a manner that X-ray transmitted images as frame images with respect to the object detected on the two-dimensional X-ray detector are synthesized together to produce image data in a predetermined section of the object, when the partial X-ray tomography is executed.

The medical X-ray apparatus may further comprises a mode switching part adapted to switch partial panoramic radiography mode for executing the partial panoramic radiography and entire panoramic radiography mode for executing an entire panoramic radiography to produce an entire panoramic X-ray image. The radiation area setting part is capable of setting the entire area of the panoramic radiography objective area as the X-ray radiation area of the entire panoramic radiography, and the image processing part produces the entire panoramic X-ray image in such a manner that X-ray transmitted images as frame images with respect to the object detected on the two-dimensional X-ray detector with respect to the object are synthesized together to produce entire panoramic X-ray image data in a predetermined section of the object in all the area of the panoramic radiography objective area, when the entire panoramic radiography is executed in the entire panoramic radiography mode.

The image processing part may produce a plurality of image data of the sectional plane from the frame images along a panoramic sectional plane and thus produced image data of plurality of sectional planes are synthesized together.

The image processing part may set a space between the plurality of sectional planes at each region of the panoramic radiography area.

The image processing part may set the thickness of an objective area to be processed of a panoramic radiography image at each region of the X-ray radiation area of the panoramic radiography.

The image processing part may produce a three-dimensional image of the X-ray radiation area from the image data of plurality of sectional planes as produced.

ADVANTAGEOUS EFFECTS

According to the present invention, the direction intersecting with scan direction is defined as a height direction, at least one of both ends of width of the X-ray beam in the height direction is set at an optional position in accordance with the position of an interested area of the object, and the X-ray restricted in the height direction is irradiated only on the interested area of the object, thereby reducing X-ray exposure amount on the object.

According to the structure in which the width of the X-ray beam in scan direction intersecting with the height direction of the X-ray radiation area is restricted, the X-ray amount exposed on the object can be further reduced.

According to the structure in which a position of at least one of both ends of the width of the X-ray beam in the height direction of the X-ray radiation area is changed in the height direction, the width of the X-ray in the height direction can be dynamically changed depending on the shape of the interested area, thereby reducing the X-ray exposure amount on the area around the interested area.

According to the structure wherein the medical X-ray apparatus comprises a moving mechanism for moving the supporting part at least in the height direction with respect to the object to change the radiating position of the X-ray beam in the height direction, the scan driving part displaces the X-ray radiation area of the X-ray beam in the height direction, so that the structure of the radiation area restricting part in the X-ray generating part can be simplified and can be downsized.

According to the structure in which the medical X-ray apparatus further comprises a driving mechanism for driving the radiation area restricting part, the radiation area restricting part comprises an open part having an opening for passing through the X-ray beam, and the driving mechanism changes the position of at least one of both ends of the width of the opening in the height direction corresponding to the interested area of the object, the supporting part is not required to be moved in the height direction, so that the driving mechanism of the supporting par can be simplified.

According to the structure in which the open part comprises a slit member having a slit restricting the X-ray beam in slit-like form and a shielding member for restricting at least one end and the other end in the height direction of the slit so as to have variable shielding amount, the X-ray radiation area of the X-ray beam can be displaced in the height direction only by controlling the shielding member, so that a large scale driving mechanism is not necessary, thereby reducing the cost.

According to the structure in which the radiography executed by the medical X-ray apparatus is X-ray tomography, the radiation area setting part makes an X-ray tomography objective area as a radiography objective area, and only a part of the X-ray tomography objective area is set as a radiation area of partial X-ray tomography, the objective area is limited and the X-ray exposure amount can be reduced.

According to the structure wherein the radiography executed by the medical X-ray apparatus is panoramic radiography in which the X-ray slit beam is irradiated to scan the object, and only a part of the panoramic radiography objective area is set as a radiation area of partial panoramic radiography for the partial X-ray tomography, the objective area is limited and the X-ray exposure amount can be reduced.

According to the structure in which the X-ray radiation area for only a tooth on an upper jaw or a tooth on a lower jaw is set as the radiation area of partial panoramic radiography among an dental arch, the objective area is limited and the X-ray exposure amount can be reduced.

According to the structure in which X-ray beam is irradiated only while the X-ray beam should pass through the radiation area of partial panoramic radiography, the objective area is limited and the X-ray exposure amount can be reduced.

According to the structure wherein the radiography executed by the medical X-ray apparatus is cephalometric radiography in which X-ray slit beam restricted by the radiation area restricting part is irradiated to scan the object, a member such as a shielding plate for shielding the area other than the objective area is not required, thereby achieving smart appearance.

According to the structure in which the radiation area setting part specifies the X-ray radiation area of the object based on the picture of the object obtained by the camera, the radiography area can be automatically set, thereby saving labor.

According to the structure in which a partial X-ray tomography image is produced in such a manner of image processing that image data of a predetermined sectional plane are formed by synthesizing frame images of X-ray transmitted images, the X-ray exposure dose can be reduced and in addition, a clear partial X-ray tomography image can be obtained by one radiography.

According to the structure in which a partial X-ray panoramic X-ray image is produced in such a manner of image processing that image data of a predetermined sectional plane are formed by synthesizing frame images of X-ray transmitted images, the X-ray exposure dose can be reduced and in addition, a clear partial panoramic X-ray image can be obtained by one radiography.

According to the structure in which a space between the plurality of sectional planes is set at each region of the panoramic radiography area, the partial panoramic X-ray image can be obtained at each region under the best image production conditions.

According to the structure in which the thickness of an objective area to be processed with a panoramic radiography image is set at each region of the X-ray radiation area of the panoramic radiography, the panoramic X-ray image can be obtained at each region with the best data amount.

According to the structure in which a three-dimensional image of the X-ray radiation area of panoramic radiography is produced from the produced image data of the plurality of sectional planes, the three-dimensional image data of the objective area can be obtained in addition to the panoramic X-ray image.

BRIEF DESCRIPTION OF DRAWINGS

FIG. 1Ca to FIG. 1Cc show an example of the radiation area restricting part driving mechanism, respectively.

FIG. 1Da to FIG. 1Dc show other example of the radiation area restricting part driving mechanism, respectively.

BEST MODE FOR CARRYING OUT THE INVENTION

A medical X-ray apparatus of the present invention is detailed. Before explaining preferred embodiments, the basic structure, the basic principle, and the basic concept of the present invention are explained.

The basic idea of the present invention is that in case of radiography mode wherein a capable radiography area is determined in advance, the diaphragm of X-ray beam XB in the height direction and the position for turning on or off X-ray beam XB are controlled to be minimum with respect to the X-ray beam XB for scanning the entire capable radiography area in order before radiography.

For this purpose, the apparatus of the present invention has means for designating a desirable radiography area in the capable radiography area, means for calculating the control conditions such as the position for turning on or off the X-ray beam XB with respect to the orbit of the X-ray beam XB by designating the radiography area and the diaphragm of the X-ray beam XB in the height direction, and means for scan radiography according to the calculated conditions.

A medical X-ray apparatus of the present invention can execute local radiography in which the X-ray beam XB is projected only on a designated radiography area as partial radiography. In this case, when the position of an interested area "r" is determined in advance, exposure to radiation can be reduced at minimum.

On the other hand, in prior art, the capable radiography area and the radiography area are basically same per radiography mode and even if the interested area being a radiography region is specified, the area is limited to a stereotypical form like a cube, a cuboid, or a horseshoe shape including the interested area "r" being a radiography region, so that there has been such a problem that X-ray is projected around the radiography region and thus projected area is exposed to radiation. Radiography for the entire capable radiography area is called as an entire radiography and radiography in which the radiography area is designated on a part of the capable radiography area is called as partial radiography. According to the present invention, only a part of area, which has been rendered to radiography in the prior art, can be irradiated with X-ray. Such a radiography in which only a part of the X-ray radiation objective area of prior radiography is designated as a radiography area may be called as a partial radiography.

Figure 1:
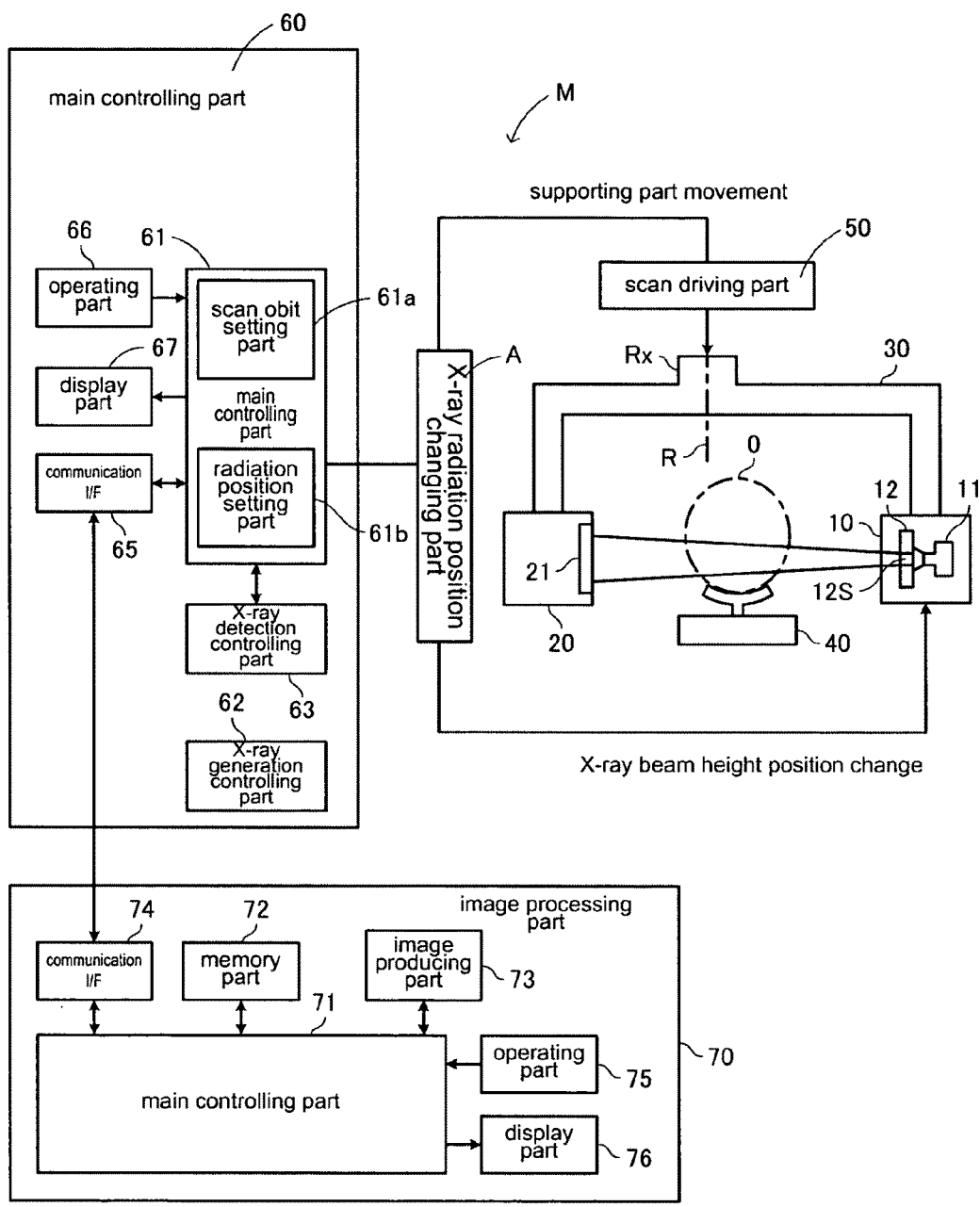
FIG. 1 shows a diagrammatic structure of a medical X-ray apparatus of the present invention.

FIG. 1 shows a diagrammatic structure of a medical X-ray apparatus of the present invention.

The medical X-ray apparatus M is provided with an X-ray generating part 10 having an X-ray generator 11 for projecting X-ray on an object to be examined "O", an X-ray detecting part 20 having an X-ray detector 21 receiving the X-ray beam XB transmitted through the object "O", a supporting part 30 for supporting the X-ray generating part 10 and the X-ray detecting part 20, respectively, while interposing the object "O" therebetween, an object holding part 40 for fixing the position of the object "O", a scan driving part 50 for driving the supporting part 30 for scanning with the X-ray beam XB during radiography, a main body controlling part 60 for controlling the apparatus body, an image processing part 70 for processing the X-ray transmitted image obtained from the X-ray detecting part 20 and for producing an X-ray image corresponding to radiography mode like panoramic radiography and cephalometric radiography, and a radiation area setting part 61b in the main body controlling part 60 as shown in FIG. 1.

The X-ray detector 21 may be provided with a casing 22 like a cassette and the casing 22 may be designed to be detachable to the X-ray detecting part 20.

The scan driving part 50 is in particular constituted with an X-Y table as mentioned in the second embodiment later.

The supporting part 30 is provided with a rotary shaft (shaft portion) Rx. The supporting part 30 is designed to be rotatable around a rotary shaft R at the shaft portion Rx, to be strict, around the rotary shaft R at the shaft center Rxc of the shaft portion Rx.

When the supporting part 30 rotates around the shaft center Rxc, the X-ray generator 11 and the X-ray detector 21 rotate around the shaft center Rxc as shown in the figure. The rotary shaft R of the supporting part 30 and the rotary shaft R of the X-ray generator 11 and the X-ray detector 21 may not conform to the mechanical shaft center Rxc of the rotary shaft Rx.

For example, in the structure in Japanese patent publication JP-2007-29168-A which is an application of the present applicant, the composite motion by the simultaneous interaction of rotation of the rotary means and movement of the rotary shaft by a rotary shaft moving mechanism generates the rotary center of radiography regardless of the position of the rotary shaft. The mechanism like the publication JP-2007-29168-A may be appropriately used to set the rotary shaft R regardless of the position of the rotary shaft Rx and the shaft center Rxc.

The X-ray generating part 10 has the X-ray generator 11 for generating X-ray and a radiation area restricting part 12 for restricting the radiation area of X-ray "X" generated from the X-ray generator 11. The radiation area restricting part 12 is the first slit or a so-called collimater having an opening 12S, the X-ray generated from the X-ray generator 11 is projected to the radiography region of the object "O" as X-ray beam XB whose projection area is restricted by the opening 12S and the X-ray transmitted image of the radiography region of the object "O" is produced on the X-ray detector 21. Namely, the radiation area restricting part 12 restricts the X-ray "X" generated from the X-ray generator 11 and permits a part thereof to pass through to be projected as the X-ray beam XB. The main body controlling part 60 and the image processing part 70 are detailed later.

The X-ray detecting part 20 sends the X-ray transmitted image produced by the X-ray detector 21 as image data to the main body controlling part 60. The X-ray detecting part 20 may be designed to be detachably provided with the X-ray detector 21 having the cassette (casing) 22 as mentioned above or to be fixed with the X-ray detector The X-ray detector 21 comprises a scintillator converting incident X-ray to visible light and a two-dimensional sensor like a CCD (Charge Coupled Device) sensor or a CMOS (Complementary Metal Oxide Semiconductor) which receives the visible light converted by the scintillator and converts it into electric signal, or comprises a cadmium telluride sensor which directly converts X-ray into electric signal without requiring a scintillator. A sensor directly converting X-ray into electric signal may be used. Or these sensors are combined.

The image sensor constituting the two-dimensional X-ray detector 21 is preferably a frame sensor is formed specifically on a flat panel, the frame sensor comprising picture elements of "m" rows and "n" columns ("m" and "n" are natural numbers, wherein m>1, n>1) in which a photoelectric conversion element like photo diode and a solid-state image sensing device are arranged like a sheet.

The main body controlling part 60 has a main controlling part 61, an operating part 66, and a displaying part 67, on which necessary information can be displayed other than the radiography image of the object to be examined "O". The main controlling part 61 comprises CPU, not shown, a scan orbit setting part 61a and the radiation area setting part 61b.

The main controlling part 61 receives setting or selection of the interested area "r" at a desirable position in the predetermined capable radiography area with the operating part 66. Specifically, a dental arch is for example divided and a plurality of selectable divisions are prepared in advance, then a part of the division may be selected as the interested area "r". The division may be a large one like an upper jaw and a lower jaw, or may be a smaller one including only a few teeth. Otherwise, each tooth may be allotted with a specific number and when a number is selected, a predetermined area including the tooth may be designed and selected. Or an X-ray image of wide area obtained by the apparatus itself or another apparatus is used as a scout view and an optional area may be designated with a mouse. The scout view is not always an actual X-ray image, but it may be a diagrammatic illustration. Designation or selection of the interested area "r" may be received in the operating part 66 and the scout view may be displayed on the displaying part 67.

When the main controlling part 61 receives designation or selection of the interested area "r" as mentioned above, it specifies a radiography area including the interested area "r" and calculates the control conditions like the position for turning on or off the X-ray beam XB with respect to the orbit of the X-ray beam XB selected by the scan orbit setting part 61a and diaphragm of the X-ray beam XB in the height direction. In scan radiography thereafter, the X-ray generating part 10, the radiation area restricting part 12 and the X-ray detecting part 20 are controlled to execute only on the specified radiography area.

The image processing part 70 has an operating part 75 receiving input by an operator with a mouse or a keyboard, an image producing part 73 producing X-ray image depending on the radiography mode like panoramic radiography or cephalometric radiography and a display part 76 displaying the produced panoramic X-ray image.

Figure 8:
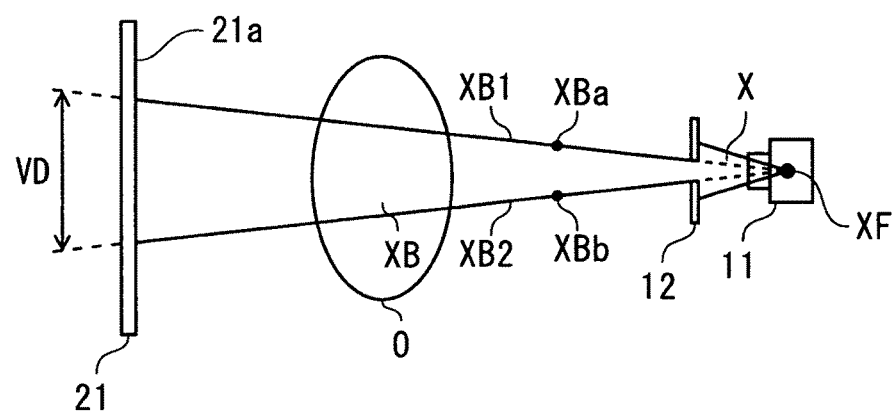
FIG. 8 shows the basic principle of radiography.
Figure 9A:
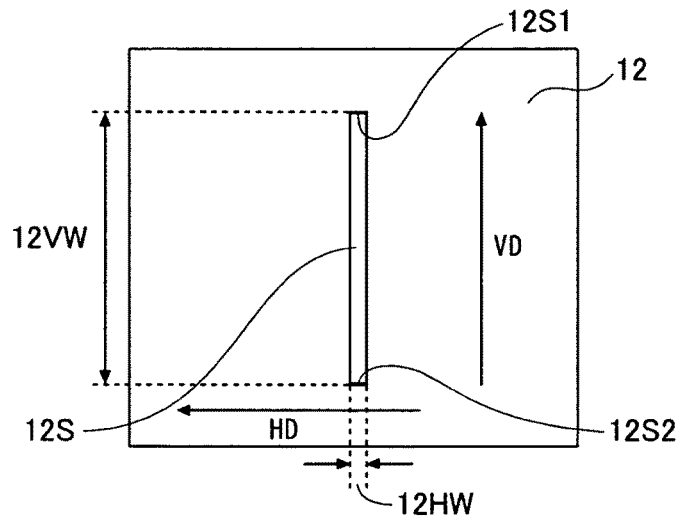
FIG. 9a and FIG. 9b are examples of scan control of X-ray beam according to the prior art.
Figure 9B:
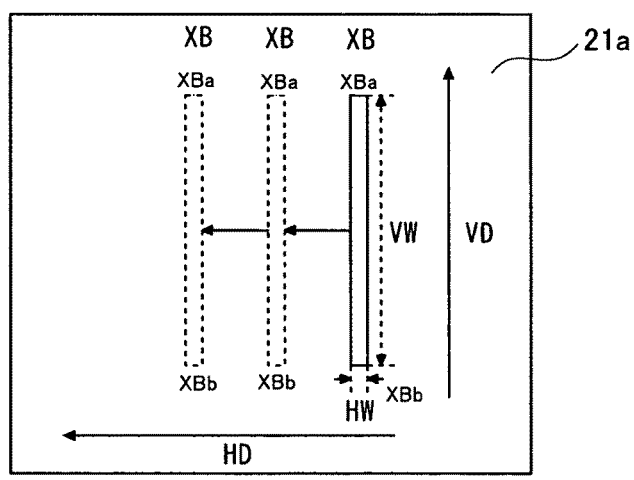
Figure 9C:
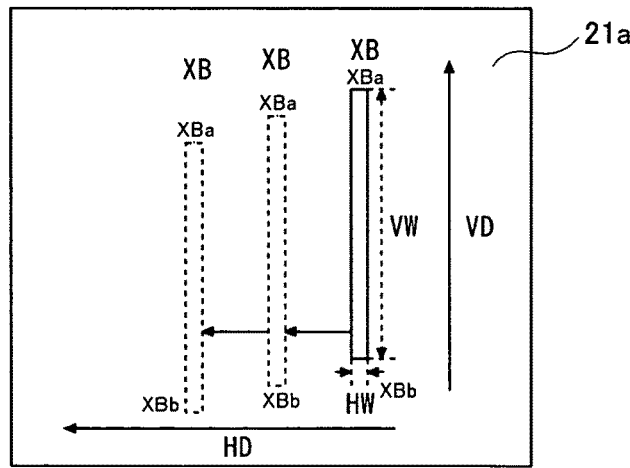
FIG. 9c is an example of scan control of X-ray beam according to the present invention.

FIG. 8 shows the basic principle of radiography and FIG. 9a to FIG. 9c show comparison of prior example of scan control of X-ray beam XB and the example of scan control of X-ray beam according to the present embodiment.

FIG. 8 is a diagrammatic view when radiography is seen from side in which the rotary shaft of the supporting part 30 is in vertical direction. In FIG. 9a the first slit 12 being the radiation area restricting part is seen from the front in the projection direction from the focus XF of the X-ray beam XB.

The radiation area restricting part 12 restricts the X-ray "X" from the X-ray generator 11 and produces the X-ray beam "XB".

Generally in radiography, as shown in FIG. 8, the positional relation of the focus XF of the X-ray beam XB, one end XB1 of the width of the X-ray beam XB in the height direction and the other end XB2 determines an X-ray projection area, an X-ray receiving area on a detection surface 21a of the X-ray detector 21 and the X-ray transmitted image to be produced on the detection surface 21a of the X-ray detector 21 with respect to the object to be examined "O". The X-ray beam XB to be projected on the object "O" and the radiography area are specified by the position of a specific point XBa on XB1 and a specific point XBb on XB2. XBa and XBb are shown with two points aligned in vertical direction in the figure.

The position of one end XB1 and the other end XB2 is determined by the position of one end 12S1 and the other end 12S2 of the opening 12S of the radiation area restricting part 12 in the height direction.

The width of the X-ray beam XB is specified by the width 12VW of the opening 12S of the radiation area restricting part 12 in the height direction and the width 12HW of the X-ray beam XB in scanning direction HD and extends to a height direction VD on the detection surface 21a of the detector 21 as shown in FIG. 9a.

In FIG. 9b the X-ray beam XB on the surface intersecting with the X-ray beam XB is seen from the front from the focus XF into projection direction.

In the example in the figure, the X-ray beam XB is seen wherein the detection surface 21a of the X-ray detector 21 is the above-mentioned intersecting surface.

In scanning the X-ray beam XB moves in the scanning direction HD. The direction intersecting the scanning (scan) direction HD is the height direction VD.

When the X-ray beam XB is a long slit beam whose shape is long in the height direction VD and the scanning direction HD is a direction intersecting the height direction VD, for example orthogonally intersecting direction, radiography can be effectively executed on a wide radiography area. In the example in the figure, the X-ray beam XB is a slit X-ray beam extending in the height direction VD and the scanning direction HD is orthogonal to the height direction VD. The scanning direction HD may be straight line or curved line as far as it crosses the height direction VD.

In the prior scan radiography, the radiography area of the object to be examined "O" is scanned in the scanning direction HD with the X-ray beam XB restricted by the opening 12S of the first slit 12. In this case, the X-ray beam XB is a slit beam and the distance VW in the height direction and the width HW in the scanning direction are constant, respectively. One end of the X-ray beam XB, which is a point XBa at the upper end on the detecting surface 21a, and the other end of the X-ray beam, which is a point XBb at the lower end on the detecting surface 21a are kept constant.

On the other hand, according to the present invention, the object "O" is scanned while displacing the X-ray beam XB in the scanning direction HD corresponding to the radiography region of the object "O" as shown in FIG. 9c. When the X-ray beam XB is displaced in the direction VD, the X-ray beam XB can be projected only on the interested area "r" as a radiography area. Or the scanning area may be designed to be variable.

The X-ray beam XB in FIG. 9c is such that the X-ray beam XB on the detection surface 21a of the X-ray detector 21 is seen from the front from the focus XF into the projection direction like FIG. 9b.

In this embodiment, at least one position of the end XB1 and the end XB2 in FIG. 8 is displaced in the height direction while scanning. It means at least one position of a point XBa on the end XB1 and a point XBb on the end XB2 on the route of the X-ray beam XB is displaced in the height direction with respect to the object "O" while scanning.

FIG. 1C and FIG. 1D exemplify a scanning pattern of the X-ray beam XB executed in the present invention. FIG. 1Ca to 1Cc and FIG. 1Da to FIG. 1Dc are diagrammatic view seen from side assuming that the rotary shaft of the supporting part 30 is in vertical. In FIG. 1Ca to FIG. 1Cc, FIG. 1Da and FIG. 1Db, (i) shows an example when the projecting position of the X-ray beam XB is high, (ii) shows an example when the projecting position of the X-ray beam XB is low, and (i) in FIG. 1Dc shows when the projection width of the X-ray beam XB is narrow and (ii) in FIG. 1Dc shows when the projection width of the X-ray beam XB is wide. The object "O" is fixed and the X-ray beam XB is moved in the embodiment, however, the present invention includes an embodiment in which the X-ray beam XB is fixed and the object "O" is moved, or an embodiment in which both the X-ray beam XB and the object "O" are moved. Namely, the X-ray beam XB may relatively move with respect to the object "O" along a predetermined radiography orbit.

In FIG. 1Ca, the X-ray generator 11 is fixed to the supporting part 30, only the radiation area restricting part 12 is moved, and the X-ray transmitting hole 12S is displaced in the height direction, thereby the X-ray beam XB being displaced in the height direction depending on the radiography region of the object "O". The X-ray beam XB may be displaced in the height direction during scanning, in such a case it is executed at the same time of horizontal or rotary movement of the X-ray beam XB in the scanning direction HD. This is also applied in the following embodiment.

FIG. 1Cb shows the structure in which the supporting part 30 is moved in the height direction to displace the X-ray beam XB in the height direction. Namely, the X-ray generator 11 and the radiation area restricting part 12 provided at its front are fixed to the supporting part 30 and the supporting part 30 is moved up and down corresponding to the radiography region of the object "O". The supporting part 30 may move during scanning with X-ray beam XB.

FIG. 1Cc shows when the radiation area restricting part 12 is pivoted to the front of the X-ray generator 11 to be integrally connected in a manner such that the X-ray generator 11 is oscillated to displace the X-ray beam XB in the height direction.

FIG. 1Da shows the structure in which the radiation area restricting part 12 is fixed to the front of the X-ray generator 11 to move the X-ray generator 11 in the height direction in the X-ray generating part 10 and the X-ray beam XB is displaced in the height direction.

In FIG. 1Db the radiation area restricting part 12 is fixed and only the X-ray generator 11 is moved in the height direction in the X-ray generating part 10, thus the X-ray beam XB is displaced in the height direction.

In FIG. 1Dc the radiation area restricting part 12 provided on the front of the X-ray generator 11 has a function capable of changing the open width of the opening in the height direction, wherein the X-ray beam XB is displaced in the height direction by changing the open width of the opening 12S in the height direction. The displacement may be executed during scanning.

The entire radiography is explained as below in case of panoramic radiography.

Figure 2:
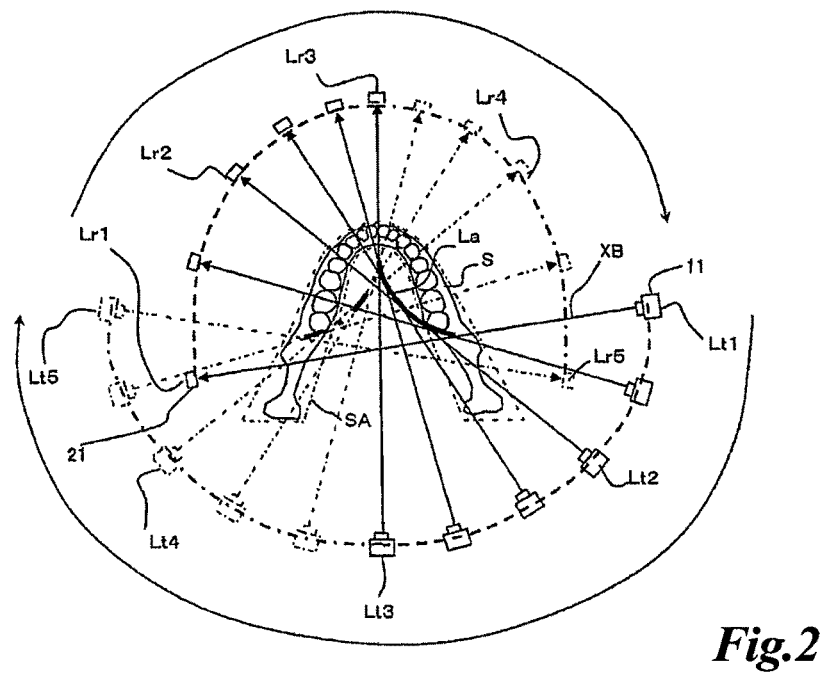
FIG. 2 shows the basic principle of panoramic radiography.

FIG. 2 shows the basic principle of panoramic radiography. In panoramic radiography, the X-ray generator 11 and X-ray detector 21 are rotated while interposing the dental arch S. Accordingly, X-ray beam XB moves for example from a position for irradiating X-ray on a left jaw, through front teeth, to a position for irradiating X-ray on a right jaw. Namely, the X-ray generator 11 sequentially moves from a position Lt1, Lt2, Lt3 . . . , and the X-ray detector 21 sequentially moves from a position Lr1, Lr2, Lr3 . . . . Then, the X-ray generator 11 moves in the order of Lt4, Lt5 and the X-ray detector 21 moves in the order of Lr4, Lr5. The curved line La in the figure shows an envelope curve drawn with the orbit of the X-ray beam XB.

FIG. 2 shows with solid lines how X-ray is irradiated from the left jaw to the center of the front teeth with respect to the X-ray generator 11, the X-ray detector 21, the X-ray beam XB, and the envelope curve La and shows with dotted lines how X-ray is irradiated from the center of the front teeth to the right jaw.

When the radiography mode like panoramic radiography and cephalometric radiography is selected in the medical X-ray apparatus M, the drive information to be executed in the scan driving part 50 for a corresponding radiography orbit is set and the radiation area setting part 61b sets the radiation area of the X-ray beam XB corresponding to the radiography region of the object to be examined "O".

In each embodiment of the present invention, the radiation area setting part 61b sets at a desired position at least one of the both ends of the width in the height direction of the X-ray beam XB corresponding to the position of the interested area "r".

Figure 5A:
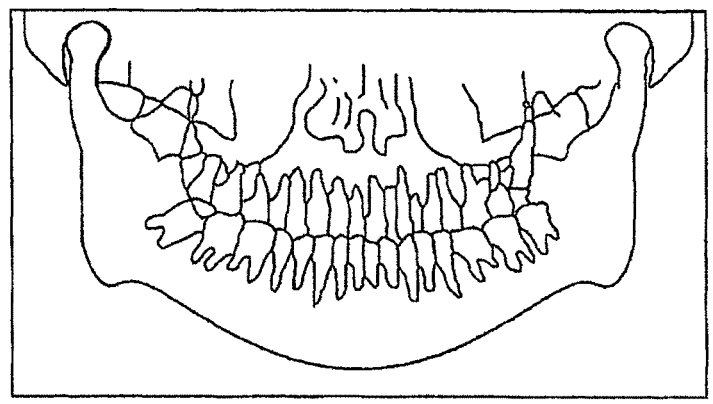
FIG. 5a is an example of panoramic X-ray image for the entire dental arch.

Panoramic radiography for the entire curved sectional plane area SA as shown in FIG. 5a is called as "entire panoramic radiography" in the present invention and the image obtained this radiography is called as the entire panoramic X-ray image. The curved sectional plane area SA is entire radiography objective area of panoramic radiography.

During panoramic radiography, the rotary shaft Rx horizontally moves in two-dimensionally by being controlled with the scan driving part 50 and the supporting part 30 horizontally rotates around the shaft center Rxc (refer to FIG. 1). The X-ray generator 11 always irradiates X-ray beam XB to the object "O", and the radiation direction becomes substantially perpendicular to the tangential line at each position of the curved sectional plane area SA which is a radiography object including the dental arch S because the two-dimensional movement of the rotary shaft Rx and the rotary movement of the supporting part 30 are combined. Consequently, the orbit of the X-ray beam XB forms the envelope curve La.

In panoramic radiography, it is required that the distance between the X-ray generator 11 and the dental arch S and the distance between the dental arch S and the X-ray detector 21 are kept almost constant in order to keep a constant magnification percentage of the image obtained at each position of the scan orbits. For this purpose, several control patterns such as the orbit of two-dimensional movement of the rotary axis Rx are desirably prepared in order to comply with the sizes of the dental arch S. A control pattern which is optimized for a presumed size of the dental arch S may be calculated with CPU under the input characteristic or the radiography region of the objet "O" such as adult or child.

The strength of the X-ray beam XB is controlled by the tube current or the tube voltage of the X-ray generator 11 with the X-ray generation controlling part 62 according to a well-known method. The X-ray beam XB irradiated from the X-ray generator 11 and restricted by the opening 12S (see FIG. 8) transmits through the object "O" and is received by the X-ray detector 21.

The X-ray detector 21 receives a clock pulse at a predetermined timing from the X-ray detection controlling part 63 and operates radiography depending on the shift amount by the rotary movement of the supporting part 30.

The horizontal transfer and the vertical transfer of the signal from the two-dimensional image sensor are controlled by the X-ray detection controlling part 63, so that the image data produced in the two-dimensional image sensor are outputted from the X-ray detecting part 20 as serial data. This output is executed each time the position of the X-ray generating part 10 and that of the X-ray detecting part 20 are shifted respectively, so that the frame image which is a corresponding X-ray projection image can be obtained at each scan orbit position (positional relation of the X-ray generating part 10, the X-ray detecting part 20 and the object "O").

The shape of the X-ray detector 21 is not specifically limited as far as it can detect the X-ray beam XB. For example, the slit X-ray beam can be received on a part of the detection surface of the flat panel detector having enough width for detecting cone-beam, and the detection surface is not limited to be long and narrow.

The image data outputted from the X-ray detecting part 20 are transferred to the X-ray detection controlling part 63, then is sent to the image processing part 70 via a communication interface 65. The image processing part 70 receives the image data in the communication interface 74 and stores it in the memory part 72. The memory part 72 stores the image data obtained by the same panoramic radiography as one data group. The memory part 72 may link the image data group of the same panoramic radiography to the information specifying the radiography date and the object to store them. Accordingly, the image data group of plural frame images obtained by one panoramic radiography can be managed as a whole per a panoramic radiography.

The image data of each frame image are stored in the memory part 72 together with the position of the rotary shaft R and the rotary angle at each radiography. The coordinate processing part 77 specifies the direction of X-ray radiation with respect to the object "O" on which each picture element on the frame image constituting the image data group is obtained based on the data stored in the memory 72, namely it specifies the line on the three-dimensional coordinate (transmitted line of object "O") on which each element exists.

Figure 4:
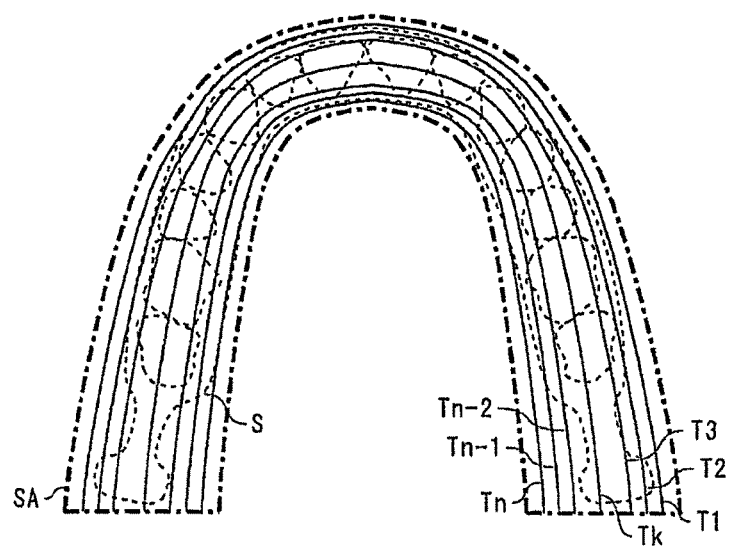
FIG. 4 is an example of the sectional plane along the curved surface of the dental arch.

The image producing part 73 recognizes the direction and the position of the transmitted line of the object "O" where each picture element on the frame image confirmed by the coordinate processing part 77 is positioned. Thus, it can confirm the picture element position on each frame image corresponding to each coordinate position of the sectional plane T1 to Tn (n is natural number) along the curved surface of the dental arch S in FIG. 4. The image producing part 73 synthesizes data (data representing the transmitted dose amount) of picture element position representing the same coordinate position on each frame image with respect to each sectional plane T1 to Tn and produces the panoramic X-ray image data (image data constituting panoramic X-ray image).

In more detail, with respect to each coordinate position of the sectional plane Tk (k is natural number from 1 to n), the frame image having the picture element position corresponding to the coordinate position is extracted and the data at the picture element position corresponding to each extracted frame are added. Namely, the frame images are summed. Summation for data of plural frame images are executed by addition or integration.

The frame image is an image projected in the projection direction and is aligned and synthesized in a direction intersecting the projection direction. Or weighted addition depending on the number of frames may be executed. Accordingly, the data amount on each coordinate position of the sectional plane Tk is calculated and is two-dimensionally distributed on the sectional plane Tk, thereby producing the panoramic X-ray image on the sectional plane Tk.

In order to obtain the panoramic X-ray image data of the sectional plane Tk, the panoramic X-ray image data production is completed here. However, the three-dimensional distribution information of the dental arch S is sometimes required.

In such a case, the image data of the plurality of sectional planes T1 to Tn including the sectional plane Tk are used. The image producing part 73 executes operation in a manner such that the panoramic X-ray image data on each produced sectional plane T1 to Tn are aligned in the direction perpendicular to the facial direction of each sectional plane T1 to Tn on the three-dimensional space. The image producing part 73 three-dimensionally distributes the data amount at each coordinate position which is two-dimensionally distributed in the panoramic X-ray image data by each sectional plane T1 to Tn and produces the three-dimensional distribution information of the X-ray absorption coefficient or the image data at plural sectional planes as 3D data of the objective area of panoramic radiography (corresponding to the curved sectional plane area SA in FIG. 2 or the local area SB in FIG. 3, mentioned later). Namely, in a similar manner to a back projection method for the image data obtained by Cr radiography, the three-dimensional distribution information of the X-ray absorption coefficient or the image data at plural sectional planes are produced. Thus produced three-dimensional distribution information or image data at plural sectional planes is linked to the image data group formed from the frame image and stored in the memory part 72.

Thereafter, the operating part 75 can select the sectional plane of the panoramic X-ray image to be outputted. The selectable sectional plane may be set at an optional shape and the above-mentioned sectional planes Ti to Tn are not necessarily selected. The panoramic X-ray image data of the sectional planes T1 to Tn have been already obtained, so that panoramic X-ray image data may be selected and displayed individually.

The image process controlling part 71, which functions as a main controlling part of the image processing part 70, specifies the sectional plane of the panoramic X-ray image to be outputted from the information inputted with the operating part 75 and provides the information on the sectional plane to the coordinate processing part 77. The coordinate processing part 77 calculates the three-dimensional coordinate of the sectional plane based on the information provided from the image process controlling part 71 and inform it to the image process controlling part 71. On the other hand, the image process controlling part 71 reads out the data at each coordinate position on the sectional plane with respect to the X-ray projection image from the three-dimensional distribution information stored in the memory 72 and provides it to the image producing part 73. Then, the image producing part 73 produces a panoramic X-ray image on the specified sectional plane from the data at each coordinate position provided from the image process controlling part 71 to be displayed on the display part 76.

Here explained is that the three-dimensional distribution information of the X-ray absorption coefficient or the image data at plural sectional planes is prepared in advance, and when the sectional plane is selected, the panoramic X-ray image of the sectional plane is produced. However, other structure is possible in that the panoramic X-ray images of plural sectional planes are produced in advance, when the sectional plane is selected, the panoramic X-ray image of the selected sectional image may be read out. After selecting or designating a sectional plane, the frame images may be synthesized. Or, for example, a CCD sensor is used as the two-dimensional image sensor and radiography is executed under TDI control and the panoramic X-ray image of the specific sectional plane may be produced.

The three-dimensional image of the radiography objective area, for example, the three-dimensional volume image, can be produced from the three-dimensional distribution information of the X-ray absorption coefficient. The three-dimensional distribution information and an optional section in the plural sectional plane image data may be displayed. Or intraoral method image by bisection method, parallel method, occulusal method and bite-wing method may be produced to be displayed on the display part 76.

According to the above-mentioned operation of the medical X-ray apparatus M, when a specific sectional plane is designated after the entire panoramic radiography, the panoramic X-ray image for the entire dental arch S is shown on the display part 76 as shown in FIG. 5a. Or when the sectional plane which is narrower than the radiography area is designated, the panoramic X-ray image of a part of the radiography object can be displayed.

Otherwise, the space between the sectional planes may be designed to be freely set in a manner such that the space between the sectional planes becomes narrow at a front tooth and it becomes wide at a cheek tooth.

Or the space between any sectional planes may be constant at every area, the number of sectional planes at a front tooth may be small, and the number of sectional planes at a cheek tooth may be large.

The sectional plane may be thick. For example, the panoramic X-ray image of the sectional plane Tk, the sectional plane T3, the sectional planes Tn-2 are synthesized so as to produce a thick panoramic sectional data including the sectional plane Tk, the sectional plane T3 and the sectional plane Tn-2, these planes T3, Tn-2 being adjacent to the plane Tk back and forth. Synthesis may be executed in such a manner that the three-dimensional coordinate position back and forth of the sectional plane is conformed. The number of sectional planes to be synthesized may be different at each region, and the thickness may be set per a region. Or the thickness of the curved sectional plane area SA which is the radiography object may be designed to be freely set in each region. Next, partial radiography is explained.

The medical X-ray apparatus M in FIG. 1 can execute partial radiography for only a local area which is a part of the curved sectional plane area SA of the entire dental arch S in addition to the above-mentioned entire radiography. Namely, the dental X-ray apparatus M can execute partial radiography on a local area when the X-ray image of a partial tooth of the dental arch S or a part of jaw bone is required, namely the interested area "r" is a local area.

The medical X-ray apparatus M may include a mode switching part, not shown, in the main body controlling part 60, which can execute both the entire radiography and the partial radiography, or execute only the partial radiography.

The tomography of the partial panoramic radiography with the medical X-ray apparatus M can be applied to other X-ray tomography. For example, X-ray tomography includes a plain surface tomography and a curved surface tomography. The apparatus may be used for tomography on a plain surface only for the jaw joint. The intraoral method image is known as a simple transmitted image which substantially includes the dental roots to the dental crowns of two to four teeth and such an image can be produced as the sectional image of the plain sectional plane of the intraoral method image.

Such a tomography on the plain sectional plane may use the X-ray detector 21 having a detection surface which can include the X-ray image from the dental roots to the dental crowns of two to four teeth, shift synthesis of the frame image may be executed in such a manner that the X-ray beam XB is irradiated so as to correspond to a desired sectional plane while moving the X-ray generator 11 and the X-ray detector 21 in the reverse direction with the objective interested area "r" interposed therebetween. Or radiography may be executed at the same or similar orbit of that of partial panoramic radiography, the coordinate operation may be executed with the objective sectional plane as a plain surface, and the frame image may be rendered to shift synthesis so as to correspond to a desirable sectional plane.

When the X-ray generator 11 and the X-ray detector 21 are moved in the reverse direction with the objective interested area "r" interposed therebetween, prior method such as plaingraphy in which the X-ray generator 11 and the X-ray detector 21 are moved along a straight line and tomography in which they are moved circularly may be used. In either case, the ratio of distance between the focus point where the X-ray is generated at the X-ray generator 11 and the objective sectional plane to the distance between the detection surface of the X-ray detector and the objective sectional plane is required to be constant.

The deflection angle of the X-ray generator 11 is preferably within 50 degrees. Or an objective sectional plane may be set in a direction perpendicular to or intersecting with the dental arch and radiography may be executed. Producing the sectional image on the plain sectional plane may sometimes eliminate such overlapping of images of the teeth that may be occured on the panoramic sectional plane. Namely, even when there is caries between adjacent teeth and it is hardly confirmed on the panoramic sectional image, for example radiography is executed with the sectional plane set in the direction orthogonal to the dental arch, diagnosis can be made possible.

Further, there is a possibility of tomography on the upper maxillary sinus, which includes tomography on the plain sectional plane and the curved sectional plane. In case of such X-ray tomography, partial X-ray tomography can be executed like the partial panoramic radiography.

The present invention can be widely applied to the radiography in which X-ray beam XB is partially irradiated on the interested area "r" and the entire interested area "r" can be finally irradiated with the X-ray beam XB to execute tomography.

Of course the panoramic radiography is an example of X-ray tomography and the panoramic radiography object area is an example of X-ray tomography objective area. In addition, the partial panoramic radiography is an example of partial X-ray tomography, the partial panoramic X-ray image is an example of partial X-ray tomography image, and the radiation objective area of partial panoramic radiography is an example of partial X-ray tomography objective area. An entire panoramic X-ray image and a partial panoramic X-ray image may be displayed such that the right jaw is at left and the left jaw is at right seen from the front or that the right jaw is at right and the left jaw is at left in reverse.

A plurality of preferred embodiments of partial panoramic radiography are explained hereinafter.

<First Embodiment>

The medical X-ray apparatus M in FIG. 1 can execute partial panoramic radiography in which radiography is executed only on a local area which is a part of a curved sectional plane area SA of the entire dental arch S in addition to the above-mentioned entire panoramic radiography.

Figure 3:
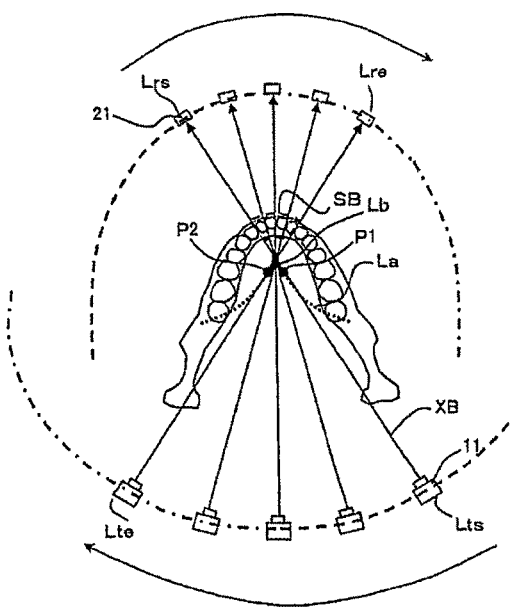
FIG. 3 shows the basic principle of partial panoramic radiography.

For example, as shown in FIG. 3, when partial panoramic radiography is executed on a local area SB only around the front teeth, X-ray beam XB from the X-ray generator 11 of the X-ray generating part 10 is irradiated in a manner such that the X-ray beam XB to be irradiated on the object to be examined "O" forms only a part Lb of an envelope curve La (solid lines in FIG. 3). In the figure, the local area SB which substantially includes two front teeth, and left and right neighbor teeth is shown in the figure. Accordingly, the X-ray detecting part 20 outputs a plurality of frame images of the X-ray transmitted image on the local area SB from the detector 21 as image data. Thus, the medical X-ray apparatus M can execute partial panoramic radiography on a local region which requires the panoramic X-ray image, so that the exposure of object "O" to radiation can be reduced comparing with the entire panoramic radiography.

Only when the X-ray beam XB forms the envelope curve Lb, the X-ray generation control part 62 controls the X-ray generating part 10 to generate X-ray. Namely, the supporting part 30 turns like in the entire panoramic radiography, however, X-ray is irradiated for only the period required for panoramic radiography on the local area SB.

The X-ray generation controlling part 62 receives the information based on the rotary degree of the supporting part 30 and the position of the X-ray generating part 10 and the X-ray detecting part 20 from the main controlling part 61. Therefore, the X-ray generation controlling part 62 recognizes a start position and an end position of radiography with respect to the local area SB and controls ON/OFF of radiation of the X-ray generator 11. ON/Off of X-ray radiation at the X-ray generator 11 may be controlled based on the driving amount of each motor, not shown, of the scan driving part 50. Further, the X-ray generation controlling part 62 may refer to a time table representing driving time of each motor of the scan driving part 50 from a start demand to rotate the supporting part 30 and sets ON/OFF period of X-ray radiation at the X-ray generator 11.

The supporting part 30 may be rotated more than a range of X-ray radiation on the local area SB in front and behind. According to such a structure, when the rotary moment of the supporting part 30 becomes enough, X-ray radiation can be started and the rotation can be stopped after mechanically reasonable deceleration. Rotation more than a range of X-ray radiation on the local area SB is required to be not the same but a part of rotary angle of the entire panoramic radiography.

For example, the supporting part 30 is at a home position and has an angle where entering and leaving of the object to be examined are not blocked, the supporting part 30 is designed to move in a manner such that the X-ray generator 10 and the X-ray detector 20 move at the minimum distance from the home position where the object enters to the starting position of X-ray radiation to the local area SB, so that it can be controlled to move at the minimum distance from the end position of X-ray radiation to the local area SB to the home position where the object leaves.

The X-ray generator 10 may have a shutter mechanism between the X-ray detecting part 20 and the X-ray generator 11. In such a case, the X-ray generation controlling part 62 controls the X-ray generator 11 to always irradiate X-ray. Only at a timing when the X-ray beam XB forms the envelope curve Lb, the shutter of the shutter mechanism is opened and X-ray beam XB is irradiated. Open and close control of the shutter mechanism can adopt the same method as ON/OFF control of X-ray radiation of the above-mentioned X-ray generator 11.

The X-ray generator 11 does not always irradiate X-ray but may irradiate X-ray for a period including the time before and after the shutter is opened and it may stop radiation in other period. Otherwise, it may irradiate X-ray in the period including some time only before the shutter is opened. According to such a structure, X-ray is irradiated under the condition that the X-ray generator 11 becomes active sufficiently.

Further according to the medical X-ray apparatus capable of partial panoramic radiography, for example, when the operating part 66 is operated following the display of the displaying part 67, the radiography objective area for panoramic radiography can be determined. For example, when a selection button for the entire panoramic radiography shown on the displaying part 67 is designated with the operating part 66, the entire panoramic radiography where the entire curved sectional plane area SA is a radiography object is selected. When partial panoramic radiography is selected, the schematic panoramic X-ray image of the upper and lower jaws or the schematic image of the dental arch is shown on the displaying part 67 and a local region to be a radiography object is specified on the image with the operating part 66.

The information of thus specified radiography objective region is given to the main controlling part 61, the main controlling part 61 sets a start position and an end position of radiography for the supporting part 30. For example, when partial panoramic radiography for the local area SB including only the front teeth is designated as shown in FIG. 3, the main controlling part 61 confirms the orbit which is already set for the scan orbit setting part 61a and calculates the start position P1 and the end position P2 on the orbit by operation, which set a starting position and an end position respectively. Specifically, the start position P1 and the end position P2 are calculated and set in the radiation area setting part 61b. P2 may be the starting position and P1 may be the end position by turning the supporting part 30 in reverse. The scan orbit is an orbit of X-ray beam XB as mentioned above, and is specifically an orbit of radiography portion when the X-ray beam XB forms the envelope curve La.

The scan orbit may be an orbit of the X-ray generator 11 and the X-ray detector 21 receiving the X-ray beam XB. The orbit can be controlled by the rotary angle of the supporting part 30 and the position of the rotary shaft Rx.

The main controlling part 61 calculates and sets the X-ray radiation range permitting X-ray radiation for the radiation area setting part 61b. The scan orbit is specified at each local region so that X-ray radiating conditions such as where and in what angle the X-ray beam XB is irradiated can be determined depending on the specified X-ray radiation range and the scan orbit.

Even after completing partial panoramic radiography, the medical X-ray apparatus M stores the image data group of a plurality of frame images, and synthesizes data from the frame images to produce panoramic X-ray image data, like the entire panoramic radiography. An image producing part 73 also produces image data to be an X-ray projection image on the sectional plane desired by an operator based on the data at each coordinate position given from the main controlling part 61.

The X-ray projection image includes not only the panoramic X-ray image on the sectional plane along the curvature of the dental arch S but also the sectional image on the sectional plane in an optional direction intersecting the sectional plane along the curvature of the dental arch S. Namely, when the position of the interested area "r" to be an objective area of partial X-ray tomography is designated, radiography can be executed on a sectional plane in an optional direction with the extending direction and its width of the sectional plane designated.

Figure 5B:
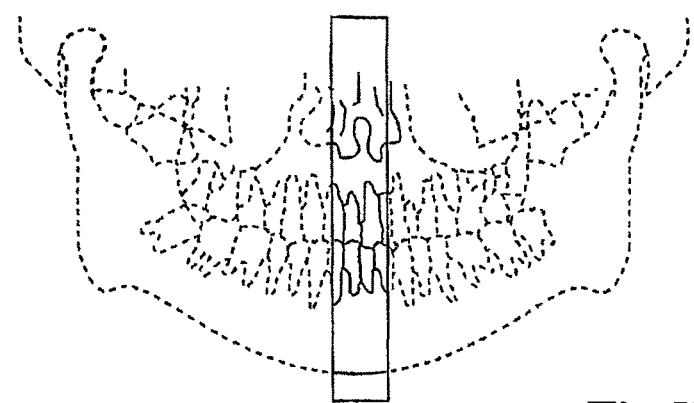
FIG. 5b is an example of panoramic X-ray image for a part of the dental arch.

When the medical X-ray apparatus M is operated as mentioned above, the entire panoramic radiography is executed in which the radiography area is the curved sectional plane area SA as shown in FIG. 2. When the panoramic X-ray image of a specified sectional plane is requested, the panoramic X-ray image for the entire dental arch S is displayed like FIG. 5a. On the other hand, when partial panoramic radiography is executed wherein the radiography area is the local area SB as shown in FIG. 3 and the panoramic X-ray image of a specified sectional plane is requested, the panoramic X-ray image for a part of the dental arch S on the local area SB is shown like FIG. 5b. Further, a desirable sectional plane can be specified as one intersecting the curved surface of the dental arch S to display the X-ray projection image on an optional sectional plane on the display part 76 within the radiography objective area. In addition, it is possible to specify a sectional plane narrower than the radiography area to display the X-ray projection image such as partial sectional image of a part of the radiography object on the display part 76.

Thus, the medical X-ray apparatus M can selectively execute partial panoramic radiography and entire panoramic radiography. When entire panoramic radiography is executed before dental treatment, all teeth of the patient are confirmed so that the tooth which requires treatment and its condition can be understood. After the treatment, the partial panoramic radiography may be executed with the medical X-ray apparatus M in order to confirm the treated tooth. In this case, the panoramic X-ray image which is already obtained by the entire panoramic radiography is displayed on the displaying part 67 and the radiography position to be executed with partial panoramic radiography may be designated by the operating part 66 on the panoramic X-ray image of the displaying part 67.

<Second Embodiment>

Figure 7:
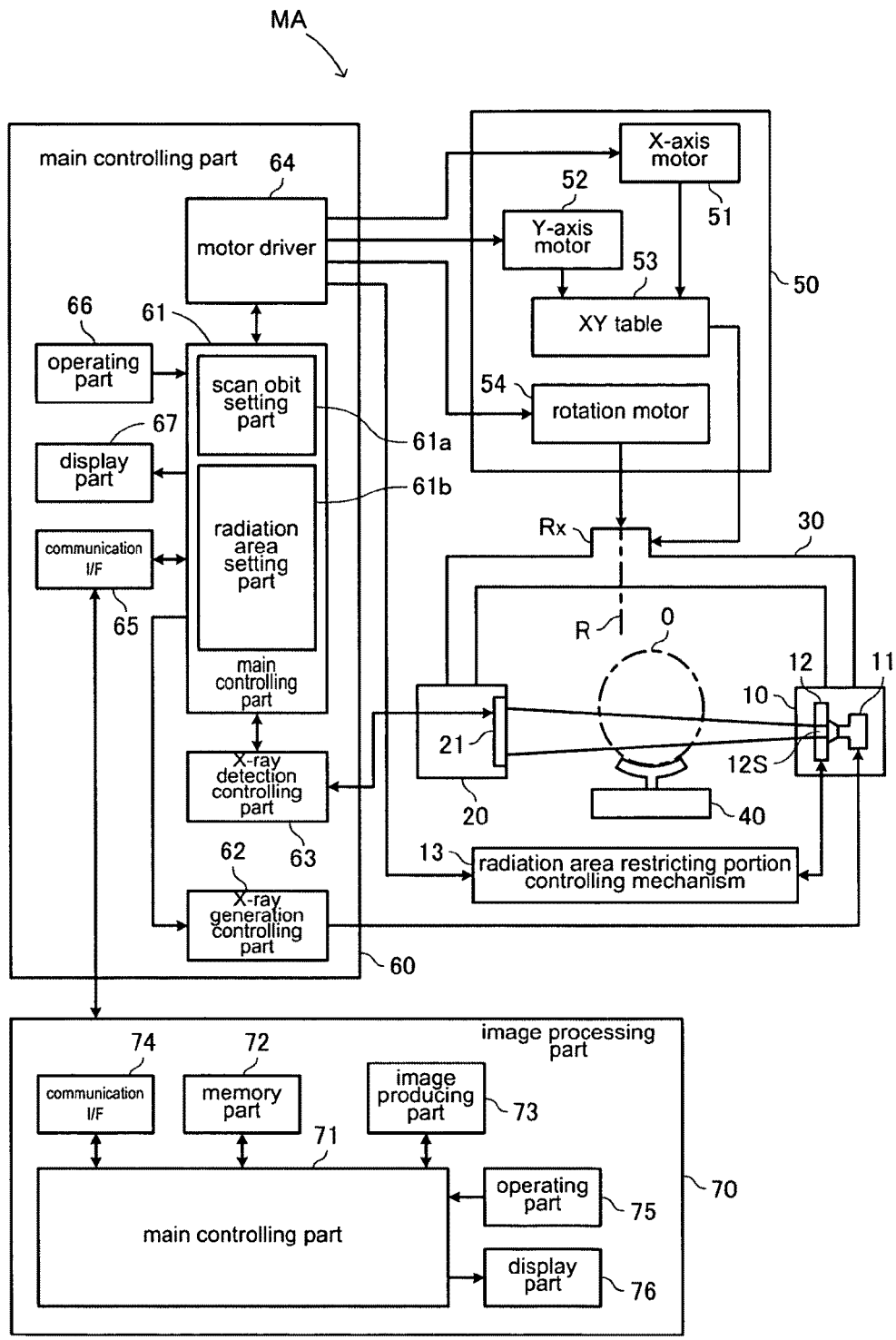
FIG. 7 shows a diagrammatic structure of other medical X-ray apparatus of the present invention.

FIG. 7 shows a basic structure of a medical X-ray apparatus MA. This apparatus MA is provided with, as mentioned in the medical X-ray apparatus M of FIG. 1, the X-ray generator 11, the X-ray generating part 10 having the radiation area restricting part 12, the X-ray detecting part 20 having the X-ray detector 21, the supporting part 30, the object holding part 40, the scan driving part 50, the main body controlling part 60 and the image processing part 70, and further provided with a radiation area restricting part driving mechanism 13.

The second embodiment is characterized by using the radiation area setting part 61b to control the radiation area restricting part driving mechanism 13 in such a structure that the radiation area restricting part 12 changes the shape of the opening 12S which restricts the X-ray irradiated from the X-ray generator 11, and the radiation area restricting part driving mechanism 13 actuates, at the time of scanning with the X-ray beam XB, the radiation area restricting part 12 to displace a radiating position of the X-ray beam XB in accordance with a radiography region of the object "O". Other structure is similar to the basic structure shown in FIG. 1 and explanation thereof is omitted by using like reference numbers to refer to corresponding parts.

The basic idea of the present embodiment is to provide the medical X-ray apparatus M which enables radiation of necessary minimum X-ray in alignment with an irregular shape of the interested area "r" and in accordance with the radiography mode.

Namely, the interested area "r" of the object "O", which becomes a radiography object, or an area contributing to the medical examination by observation of the area, does not usually have a regular geometric shape such as cuboid and cube, but has an irregular shape for the purpose of the medical examination per radiography mode, and if X-ray radiation is restricted to the interested area "r" as much as possible in radiography executed by scanning the interested area "r" with the X-ray beam XB, unnecessary exposure to X-ray can be avoided.

In view of such circumstances, in the X-ray computed tomography, improvements can be seen in some cases in such that exposure to X-ray is reduced by local radiation using cone-beam. However, in panoramic radiography, no device has been made to reduce exposure to X-ray to an optimum limit in accordance with the shape of the interested area "r" of the object "O".

On the contrary, the present inventors have designed a structure in which the radiation area setting part 61b according to the present embodiment is used to restrict the radiation area of the X-ray beam XB in the height direction by adjusting the position of both ends of the width of the X-ray beam in the height direction to a position and shape of the radiography region. Note that the radiation area of the X-ray beam XB may be changed in the height direction during scanning with the X-ray beam XB.

The basic idea of the present invention is also utilized in a third embodiment mentioned later.

In a scan control example of the X-ray beam XB shown in FIGS. 13a and 13b mentioned later, while the X-ray beam XB is moved in the scanning direction HD, X-ray is irradiated by changing the diaphragm of the X-ray beam XB or the distance VW thereof in the height direction to be wider or narrower in accordance with a radiography region of the object "O", and at least one of the both ends of the width of the X-ray beam in the height direction is restricted in the height direction depending on the radiography area position and its shape.

Figure 11A:
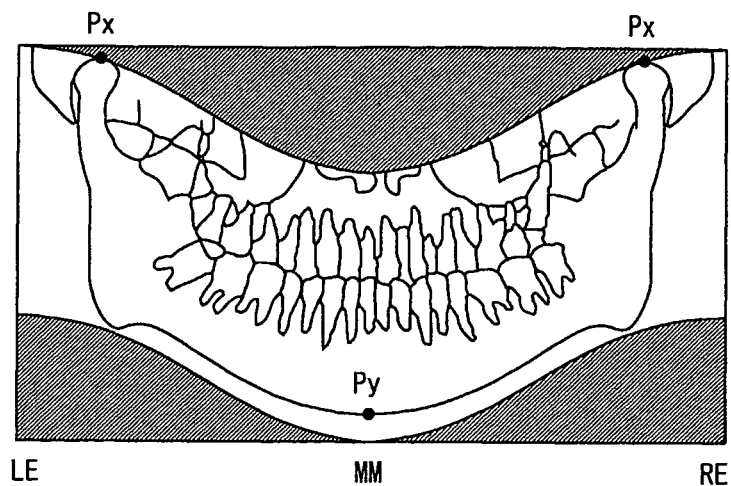
FIG. 11a shows an example of the panoramic X-ray image of the entire jaw obtained in the present invention.
Figure 14:
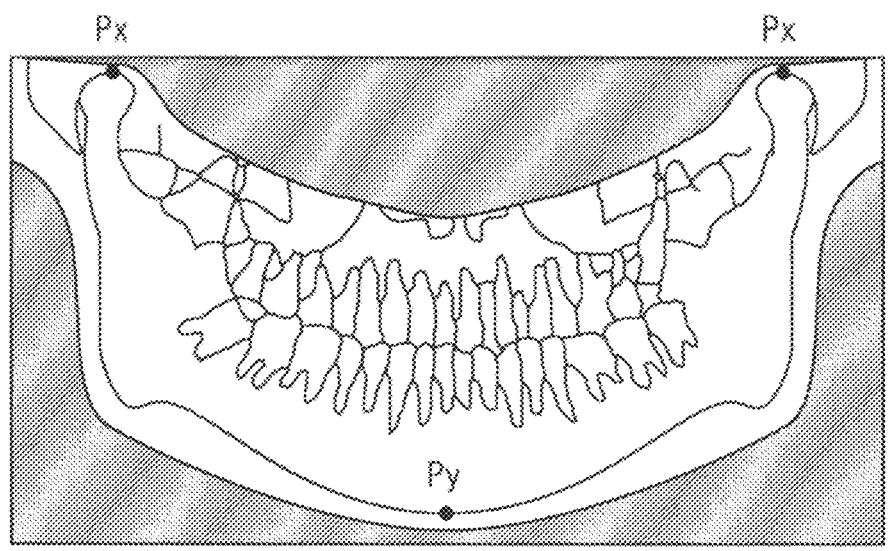
FIG. 14 is an example of panoramic X-ray image obtained in the present invention.

Accordingly, as a result of such scanning with the X-ray beam XB, it is made possible in the present invention to obtain a panoramic X-ray image as shown in FIG. 11a and FIG. 14 mentioned later without exposure to X-ray in areas other than the interested area "r" of the object "O".

Like an example of FIG. 13c mentioned later, while setting the width VW1 of the X-ray beam XB in the height direction to be constant, the width of the X-ray beam XB in the height direction may be restricted for scanning, in comparison with conventional scanning with the X-ray beam XB.

The radiation area restricting part 12 combines shielding members 134, 136, ... shown in FIG. 12 with a slit member 12a mentioned later and moves the opening 12S up and down to restrict the width of the X-ray beam XB in the height direction and irradiate it on the object "O" in slit-like form.

Figure 10A:
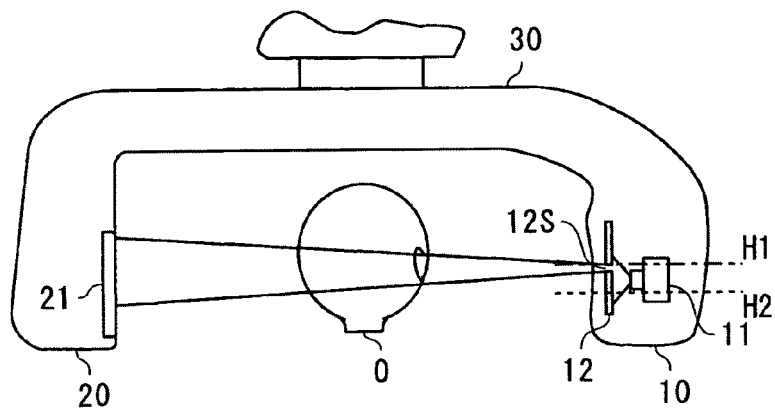
FIG. 10a to FIG. 10c show examples wherein the irradiation area restricting part is actuated to displace the opening of the radiation area restricting part in different height, respectively.
Figure 10B:
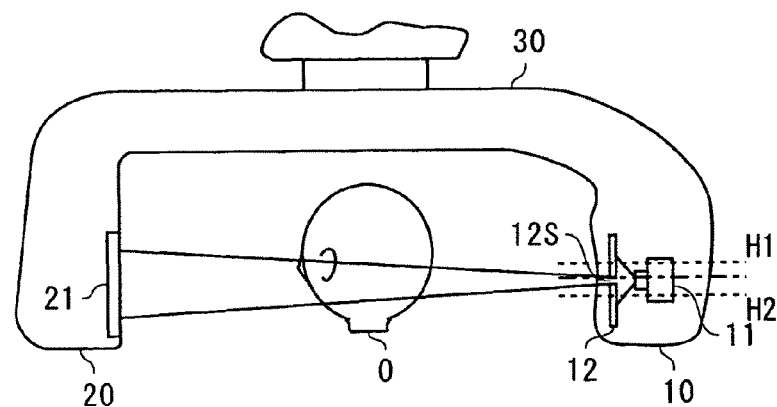
Figure 10C:
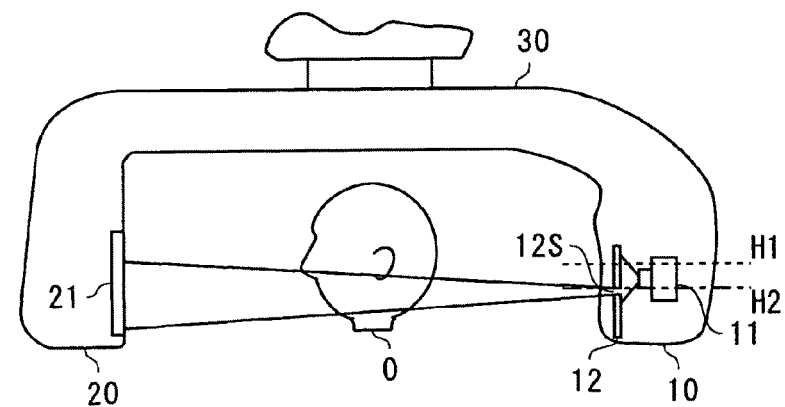

When panoramic radiography is executed, the radiation area restricting part 12 is actuated by the radiation area restricting part driving mechanism 13 to displace the opening 12S in the height direction as shown in FIGS. 10a to 10c, while causing the supporting part 30 to rotate around the object "O".

The width of the opening 12S in the height direction is restricted more than the width of the opening in the height direction for use in conventional panoramic radiography, and corresponds to the width of the interested area "r" in the height direction.

Here, H1 and H2 refer to the highest position and the lowest position of the opening 12S in height direction or the highest position and the lowest position of an upper end of the opening 12S in height direction here, respectively, wherein the opening 12S moves up and down between H1 and H2, along with a rotary operation of the supporting part 30, in accordance with a radiography region of the object "O" or the interested area "r".

In order to emphasize a positional change between H1 and H2, the radiation area restricting part 12 shown in FIG. 10a and FIG. 10c is drawn with H1 higher than an actual position and H2 lower than an actual position. Therefore, focal deviation of the X-ray beam XB in the figures is emphasized to promote understanding and an actual positional change of the radiation area restricting part 12 between H1 and H2 is not as large as shown in the figures.

Figure 11B:
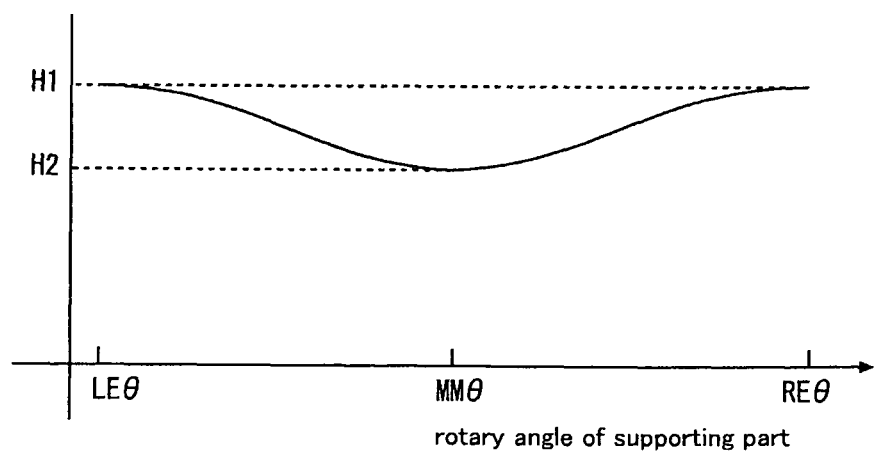
FIG. 11b shows the change in the height of the opening of the radiation area restricting part for obtaining the image.

FIG. 11a shows a panoramic X-ray image of the entire jaw obtained by the present invention. FIG. 11b is made to correspond to FIG. 11a in terms of position and shows a height position change of the opening 12S in accordance with a rotary angle of the supporting part 30 when panoramic radiography is executed, wherein the corresponding portions to the left end LE, the center MM and the right end RE, seen facing to a panoramic X-ray image, are sequentially subjected to X-ray irradiation in accordance with a rotary movement of the supporting part 30 from LEθ, where the left jaw is irradiated, to MMθ, where the front teeth are irradiated, to REθ where the right jaw is irradiated, and an X-ray transmitted image of the corresponding portions is generated on the X-ray detector 21.

When the panoramic X-ray image is displayed, generally, the right jaw is shown on the observer's left and the left jaw is shown on the observer's right, however, these positions are reversed in FIG. 11a for convenience sake.

In the present embodiment, while the supporting part 30 rotates, the opening 12S moves up and down between H1 and H2 by adjusting itself to the position of a radiography region of the object "O", thereby generating a panoramic X-ray image with high Px, Px on the left and right jaw joint sides and low MM on the front teeth side, and, as a result, X-ray exposure to a shaded portion can be eliminated.

Namely, the shaded portion is the X-ray radiation restricting area and a portion excluding the shaded portion serve as the interested area "r".

In the present embodiment, the width of the X-ray beam XB in the height direction is restricted by the opening 12S so that the X-ray beam XB is irradiated only on the interested area "r".

The position of the opening 12S may not always vertically move between H1 and H2 in height direction while the supporting part 30 is turned, and the position of the opening 12S may not be changed during radiography at each region even though the position of the opening 12S is changed at each region.

For example, X-ray may be irradiated only on the left jaw joint or only on the right jaw joint with the opening 12S fixed at H1 or X-ray is irradiated only on the front teeth with the opening 12S fixed at H2 in height direction keeping the height at fixed position during the radiography.

Thus the partial panoramic radiography for left jaw joint as for single region can be executed for example.

The partial panoramic radiography for right jaw joint or The partial panoramic radiography for front teeth is so as the same.

Plural region may be set for which serial X-ray radiation for each of them are executed.

For example, X-ray may be irradiated on the left jaw joint with the opening 12S fixed at H1 at first, and next the position of the opening 12S is changed, continually X-ray is irradiated on the front teeth the opening 12S fixed at H2.

Of course the regions may be not limited only two regions, three or more regions including entire area in total are available.

Note that, in the medical X-ray apparatus MA which executes panoramic radiography for an object "O" in a three-dimensional state, the scanning direction of the X-ray beam XB intersects the rotary shaft of the supporting part 30 and falls in a displacement direction of one point which is on the path of the X-ray beam XB on a horizontal plane or a substantially horizontal plane which is intersected by the X-ray beam XB. In contrast, in the medical X-ray apparatus M which executes panoramic radiography for the object "O" in a recumbent state, the scanning direction of the X-ray beam XB intersects the rotary shaft of the supporting part 30 and falls in a displacement direction of one point which is on the path of the X-ray beam on a vertical plane or a substantially vertical plane intersected by the X-ray beam XB.

The supporting part 30 is composed of, for example, a rotary arm. The rotary arm supports the X-ray generating part 10 and the X-ray detecting part 20, respectively, while interposing the object "O" therebetween, and is caused to rotate around the object "O" by the scan driving part 50 during panoramic radiography.

The scan driving part 50 is provided with an X-axis motor 51 for displacing the rotary shaft Rx of the supporting part 30 in the horizontal direction (or X-axis direction), a Y-axis motor 52 for displacing the rotary shaft Rx in a direction orthogonal to the X-axis direction (i.e. Y-axis direction), an X-Y table 53 for moving the supporting part 30 in the horizontal and vertical directions by driving the X-axis motor 51 and the Y-axis motor 52, and a rotary motor 54 for rotating the supporting part 30 by using the rotary center R of the rotary shaft Rx as a shaft center.

In the scan driving part 50, the X-axis motor 51 and the Y-axis motor 52 are driven to turn so as to move the rotary shaft Rx of the supporting part 30 on the X-Y table 53 and displace the shaft center R of the supporting part 30 to a predetermined position, and the rotary motor 54 is driven to turn the X-ray generating part 10 and the X-ray detecting part 20 around the object "O".

The X-axis motor 51 and the Y-axis motor 52 are driven to turn at the same time as driving the rotary motor 54 to turn, whereby above-mentioned panoramic radiography is executed by the X-ray generating part 10 and the X-ray detecting part 20.

The supporting part 30, which constitutes a radiography part along with the X-ray generating part 10 and the X-ray detecting part 20, may have the rotary shaft Rx which is fixed and driven to turn by the rotary motor 54.

The supporting part 30 may also be driven to turn by fixing the rotary shaft Rx to the X-Y table 53 and turnably attaching the supporting part 30 to the rotary shaft Rx so as to bring a driving power into effect in the rotary shaft Rx by the rotary motor 54 which is fixed to the supporting part 30.

The medical X-ray apparatus MA is provided with, like the medical X-ray apparatus M of FIG. 1, the main body controlling part 60, the main controlling part 61, the X-ray generation controlling part 62, an X-ray detection controlling part 63, a communication interface 65, the operating part 66, the displaying part 67 and other parts.

The main body controlling part 60 includes the main controlling part 61 for processing operation of various data transmitted to and received from each block in the main body controlling part 60, the X-ray generation controlling part 62 for controlling ON/OFF of the X-ray generator 11 in the X-ray generating part 10 and the value of the tube current and the tube voltage in the X-ray generator 11, an X-ray detection controlling part 63 for controlling the X-ray detector 21 in the X-ray detecting part 20 and receiving image data from the X-ray detecting part 20, a motor driver 64 for generating a control signal supplied to each of motors 51, 52 and 54 in the scan driving part 50 and the radiation area restricting part driving mechanism 13, the communication interface 65 for transmitting and receiving a signal to/from the image processing part 70, the operating part 66 for receiving an input by operation of an operator, and the displaying part 67 made of a liquid crystal display and the like.

The motor driver 64 plays a role of a drive signal converting part which receives a control signal from the scan orbit setting part 61a and converts it to a drive signal supplied to the scan driving part 50.

The main body controlling part 60 includes the operating part 66 made of an operation panel and the like, and when a panoramic radiography mode for executing radiography and a position and size of the radiography region are selected in response to an input of the sex and age of a subject being the object "O", a radiography orbit (or scan orbit) of the supporting part 30 is calculated with respect to the selected radiography mode and radiography region, and the calculated radiography orbit is set in the scan orbit setting part 61a, followed by, in accordance with scanning, radiation position information of the X-ray beam XB is set in the radiation area setting part 61b. If there are any other available radiography modes than the panoramic radiography, selection of a radiography mode is followed by setting a radiography orbit with respect to the selected radiography mode.

For example, in panoramic radiography selected as a radiography mode, an orbit of the rotary center R and a rotary angle of the supporting part 30 are calculated to determine a radiography orbit of the X-ray beam XB so that an image of a panoramic sectional plane with a position and size corresponding to a standard adult is taken if the object "O" is an adult or an image of a panoramic sectional plane with a position and size corresponding to a standard child is taken if the object "O" is a child.

Panoramic radiography is determined by a composite movement determined by the movement of the rotary shaft Rx of the supporting part 30 and the rotary operation around the rotary shaft Rx of the supporting part 30, so that a control pattern of the orbit of the rotary shaft Rx and the rotary angle of the supporting part in each position on the orbit (or scanning radiography orbit of the X-ray beam XB) may also be prepared as radiography profile information. This profile information may also include the height position of the opening.

Only one piece of such radiography profile information may be prepared to calculate a radiography orbit from the basic information or a plurality of control patterns of the radiography orbit corresponding to the difference of adult and child and the sex may be prepared in advance to selectively use a control pattern.

Note that, other than the above example which is a structure example to displace the rotary shaft Rx of the supporting part 30 by driving the X-axis motor 51 and the Y-axis motor 52, a mechanical rotary shaft movement guiding structure such as displacing the rotary shaft Rx along a prearranged groove in accordance with a rotary angle of the supporting part 30 may also be employed, and in this case, the scan orbit setting part 61*a* in the figure is not a control element like software.

The scan driving part 50 includes the X-axis motor 51, the Y-axis motor 52, the X-Y table 53, and the rotary motor 54, wherein radiography by scanning is executed by moving the supporting part 30 and therefore moving the X-ray beam XB restricted by the above-mentioned radiation area restricting part 12.

Other than the example in the figure for constituting the scan driving part by the X-axis motor 51, the Y-axis motor 52, the X-Y table 53 and the rotary motor 54, any structures may be employed as long as the X-ray beam XB is moved in order to realize scanning with the X-ray beam XB, with no limitations to the structure of using the above X-Y table 53, and an appropriate mechanism to allow two-dimensional movement of the X-ray generating part 10 and the X-ray detecting part 20 can be employed.

The main controlling part 61 notifies a motor driver 64 of radiography orbit information obtained from a calculated orbit of the rotary center R and a rotary angle, and the motor driver 64 outputs a driving signal to each of the motors 51, 52 and 54 in the scan driving part 50, whereby the X-ray generating part 10 and the X-ray detecting part 20 in respective positions are displaced to appropriate positions and rotated, while the supporting part 30 is displaced in the horizontal direction.

Note that the motor driver 64 in the example shown in the figure is indicated as an independent element provided in the main body controlling part, but it is not essential as an independent element because the function to output a drive signal to each motor can be provided in, for example, the main controlling part 61. Similarly, the motor driver 64 in FIG. 22 mentioned later is not essential.

The main controlling part 61 stores a displacement amount of the height position of the opening 12S relative to the rotary angle of the supporting part 30. It may be calculated every time the interested area "r" is designated.

This reference information includes information on a displacement amount of the opening 12S displaced in the height direction relative to a reference position every time the supporting part 30 rotates at a predetermined angle, wherein the height position of the opening 12S relative to the rotary angle of the supporting part 30 at the start of panoramic radiography is set as a reference position. Of course, the height position at the start of radiography does not necessarily need to be a reference position and optional positions may be set as a reference position.

The main controlling part 61 makes a control, during panoramic radiography, so that a height position of the opening 12S is displaced relative to a rotary angle of the supporting part 30. This displacement control of the height position of the opening 12S is realized by a drive signal outputted from the motor driver 64. The drive signal output by the motor driver 64 also causes movement of the supporting part 30 simultaneously.

The main controlling part 61 may also include, as a radiography profile, the height position of the opening 12S in addition to the scanning radiography orbit of the X-ray beam XB and the rotary angle of the supporting part 30 in each position on the orbit in accordance with a radiography region of the object "O". As for such radiography profile information, it is desirable to prepare a plurality of control patterns corresponding to the difference of adult and child and the sex and select any one of them for use, as mentioned above.

The main controlling part 61, which executes panoramic radiography based on the radiography profile information, may also calculate, without using the radiography profile information, the height position of the opening 12S relative to a rotary angle at the start of radiography by inputting a position of the radiography region using the operating part 66. In this case, the main controlling part 61 determines, based on a calculated height position of the opening 12S relative to a rotary angle at the start of radiography and stored reference information, a height position of the opening 12S relative to a rotary angle of the supporting part 30 as shown in FIG. 11*b*.

Furthermore, the main controlling part 61 synchronizes a control operation in the X-ray generation controlling part 62 and the X-ray detection controlling part 63 with a driving operation by the motor driver 64, and X-ray generation controlling part 62 can therefore control at least one value of the tube current and the tube voltage supplied to the X-ray generator 11, in accordance with a position and a rotary angle of the rotary center R of the supporting part 30 to be determined by driving the scan driving part 50 by the motor driver 64.

The tube current or the tube voltage supplied to the X-ray generator 11 can be set to a value corresponding to an area on which the X-ray beam XB is irradiated by the X-ray generating part 10. For example, if an obstacle (such as cervical vertebra) other than an object is present in an area through which the X-ray beam XB is passed, the amount of X-ray irradiated from the X-ray generating part 10 can be controlled to an optimum value by increasing at least one of the tube current and the tube voltage.

Following next is to explain the radiation area restricting part driving mechanism.

Figure 12A:
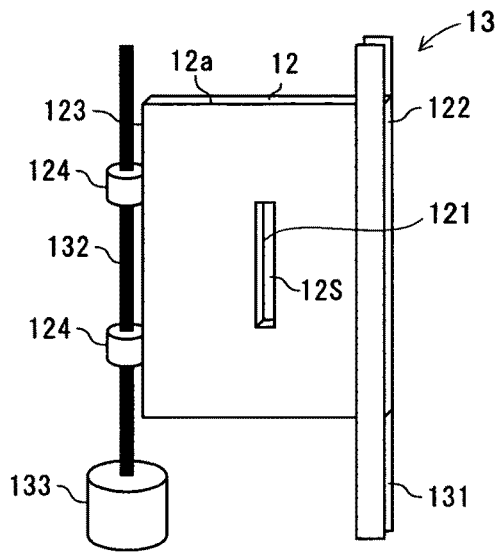
FIG. 12a to FIG. 12c show an example of the radiation area restricting part driving mechanism, respectively.
Figure 12B:
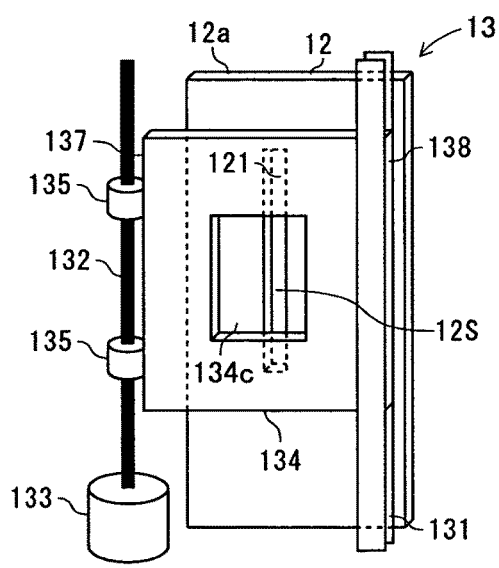
Figure 12C:
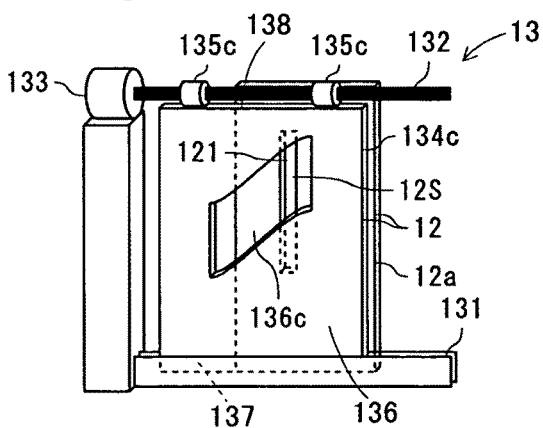

FIGS. 12*a* to 12*c* show an embodiment of the radiation area restricting part driving mechanism 13. Details of each structure are explained. The radiation area restricting part driving mechanism 13 shown in FIG. 12*a* is designed in such that one end 122 of the slit member 12*a* established with an opening 121 extending in the height direction is fitted into a guide groove 131, the other end 123 on the opposite side of the slit member 12*a* is arranged with female screw parts 124 and 124 each of which has an internally formed screw groove, and a rotary shaft 132 of a motor 133 formed with a screw thread is screwed through and penetrated into the female screw parts 124 and 124. The radiation area restricting part 12 is composed of the slit member 12*a*, and the opening 121 thereof constitutes the opening 12S.

The width of the opening 121 in the height direction in FIG. 12*a* is restricted more than a slit width for use in conventional panoramic radiography and set to a width suitable for the interested area "r". The slit member 12*a* is an example of an opening part which forms the opening 121 for permitting part of X-ray to pass therethrough.

According to such a structure, the slit member 12*a* can be moved up and down by screwing forward the female screw parts 124 and 124 which are screwed through the rotary shaft 132, owing to forward rotation and reverse rotation of the motor 133 by a control signal supplied from the main body controlling part 60 to the motor 133. Therefore, at the time of scanning with the X-ray beam XB, if forward/reverse rotation of the motor 133 is controlled in accordance with a radiography region of the object "O", a radiation position of the X-ray beam XB irradiated on a radiography region of the object "O" can be displaced along the height direction by moving the opening 12S up and down.

The radiation area restricting part driving mechanism 13 of FIG. 12*b* is structured by combining the radiation area restricting part 12, which is composed of the slit member 12*a* having the opening 121 with a width being wider than that of the opening 121 of the slit member 12*a* of FIG. 12*a* in the height direction and being the same as a slit width for use in conventional panoramic radiography, and a shielding plate 134 established with an opening 134c which is expanded more than the opening 121 of the slit member 12a in the horizontal direction, wherein one end 138 of the shielding plate 134 is fitted into the guide groove 131, the other end 137 on the opposite side of the shielding plate 134 is arranged with female screw parts 135 and 135 each formed with a screw thread internally, and a rotary shaft 132 of the motor 133 formed with a screw thread is screwed through and penetrated into the female screw parts 135 and 135.

According to such a structure, the opening 121 established in the slit member 12a and the opening 134c established in the shielding plate 134 are superposed to each other to form the opening 12S.

Dimensions of the opening 134c are such that it is smaller than the opening 121 in the longitudinal direction but larger than the opening 121 in the lateral direction.

Accordingly, the rotary shaft 132 is turned owing to forward rotation and reverse rotation of the motor 133 by a control signal supplied from the main body controlling part 60 to the motor 133, and the female screw parts 135 and 135 which are screwed through the rotary shaft 132 are screwed forward to move the shielding plate 134 up and down. Therefore, at the time of scanning with the X-ray beam XB, if forward/reverse rotation of the motor 133 is controlled in accordance with a radiography region of the object "O", a radiation position of the X-ray beam XB which is irradiated on the object "O" can be displaced along the height direction by moving the opening 12S up and down.

Moreover, if the slit member 12a is removed, X-ray cone-beam can be emitted from the opening 134c of the shielding plate 134, thereby enabling local X-ray computed tomography. Furthermore, by designing the slit member 12a to be detachable, the medical X-ray apparatus can be rendered to be the medical X-ray apparatus MA used for both the above-mentioned partial panoramic radiography and local X-ray computed tomography.

The above-mentioned entire panoramic radiography may also be realized by extending the rotary shaft 132 and the guide groove 131 much more than those shown in the figure and raising the shielding plate 134 to move the shielding plate 134 to a position in which the opening 121 is not closed at all.

In addition, when the opening 134c of the shielding plate 134 moves toward upper and lower ends of the opening 121 of the slit member 12a, a superposed portion made by the opening 134c of the shielding plate 134 and the opening 121 of the slit member 12a becomes smaller than the upper and lower widths of the opening 134c, and in a range of the superposed portion formed at this time, an opening dimension of the opening 12S in the longitudinal direction can be changed to increase and decrease.

The shielding plate 134 is an example of the shielding part, and the slit member 12a and the shielding plate 134 serve as an example of the opening part in which the opening 12S for permitting part of X-ray to pass therethrough is formed.

The radiation area restricting part driving mechanism 13 shown in FIG. 12C is also structured to use the slit member 12a similar to that of FIG. 12b in combination with a shielding plate 136, wherein the shielding plate 136 is designed to move in the horizontal direction.

Namely, the slit member 12a is established with the longitudinal opening 121 similar to the above-mentioned one, whereas the shielding plate 136 is designed so that a lower end 137 thereof is fitted into the guide groove 131 and an upper end 138 thereof is arranged with female screw parts 135c and 135c each formed with a screw groove internally, wherein the rotary shaft 132 of the motor 133 formed with a screw thread is screwed through and penetrated into the female screw parts 135c and 135c. Then, an opening 136c, which is established in the shielding plate 136, has the same upper and lower dimensions and extends to an oblique downward direction.

According to such a structure, the opening 121 established in the slit member 12a and the opening 136c established in the shielding plate 136 are superposed to each other to form the opening 12S, and if the motor 133 is rotated forward or reversely by a control signal supplied from the main body controlling part 60 to the motor 133, the rotary shaft 132 is turned and the female screw parts 135c and 135c screwed through the rotary shaft 132 are screwed forward so as to move the shielding plate 136 in the horizontal direction. Therefore, at the time of scanning with the X-ray beam XB, if forward/reverse rotation of the motor 133 is controlled in accordance with a radiography region of the object "O", a radiation position of the X-ray beam XB which is irradiated on the object "O" can be displaced along the height direction by moving the opening 12S up and down.

Moreover, if the opening 136c extending in the horizontal direction is formed into a shape corresponding to a radiography region of the object "O" in the shielding plate 136, the shielding plate 136 can be used as a simple X-ray transmitting filter and the X-ray beam XB irradiated beyond the shape of the opening 136c can be cut off. Therefore, if various kinds of shielding plates are prepared with an opening formed corresponding to a shape of the radiography region of the object "O", X-ray exposure to regions other than the radiography region can be simply prevented by replacing the shielding plates.

Note that, though it is not shown, as a modification of the second embodiment, the X-ray detector 21 may be displaced relative to the height direction in the X-ray detecting part 20. In this case, the height position of the X-ray detector 21 is displaced in alignment with displacement of the height position of the radiation area restricting part 12 in the X-ray generating part 10, and if, in the height direction, the center of the radiation area restricting part 12 or the center of the X-ray beam XB is constantly present on a straight line which is connected to the center of a detection surface of the X-ray detector 21 from the focus XF of the X-ray generator 11, an X-ray radiation area with respect to the X-ray detector 21 can be substantially constant, so that a detection surface area of the X-ray detector 21 can be narrowed. There may also be a structure to fix the X-ray detector 21 to the X-ray detecting part 20 and allow displacement of the X-ray detecting part 20 as a whole relative to the supporting part 30 in the height direction.

The shielding plate 136 is an example of the shielding part, and the slit member 12a and the shielding plate 136 serve as an example of the opening part in which the opening 12S for permitting part of X-ray to pass therethrough is formed.

<Third Embodiment>

A third embodiment of the medial X-ray apparatus according to the present invention is explained hereinafter.

This medical X-ray apparatus has no difference to FIG. 7 as long as it is shown in the block diagram and therefore a block diagram thereof is omitted. The present embodiment is characterized in such that the radiation area restricting part driving mechanism 13 has a function which enables to change the opening width of the opening to be wider or narrower in the height direction during scanning with the X-ray beam XB.

Figure 13A:
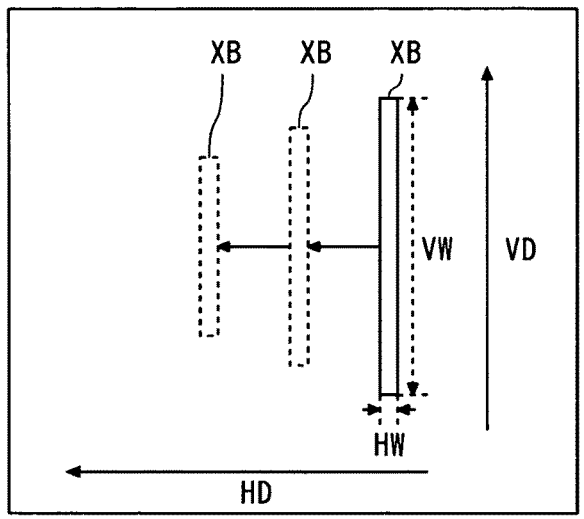
FIG. 13a to FIG. 13c show an example of scan control of the X-ray beam, respectively.
Figure 13B:
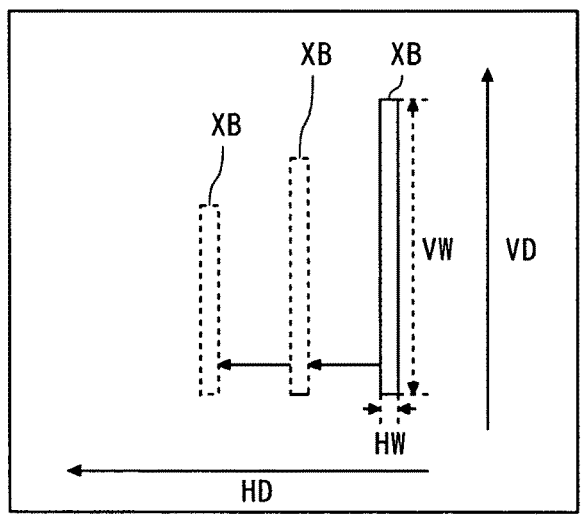

FIGS. 13a and 13b show a basic principle of the scan control of the X-ray beam XB to be executed in the third embodiment.

Characteristics of the scan control of the X-ray beam XB are explained in comparison with the second embodiment. In the second embodiment, as shown in FIG. 9b, the X-ray beam XB is displaced without changing a width thereof in the height direction during scanning. It is because a position of the opening 12S in the height direction is displaced in accordance with a radiography region of the object "O" without changing an opening width thereof. In contrast, as for the X-ray beam XB in the third embodiment, during scanning, the opening width of the opening 12S in the height direction, or the width of the X-ray beam XB in the height direction is changed to be larger or smaller in accordance with the radiography region of the object "O", and radiation of the X-ray beam XB is therefore more restricted to an optimum range with respect to the radiography region than the second embodiment.

In FIG. 13a, the X-ray beam XB in a detection surface 21a of the X-ray detector 21 is seen from the front from the focus XF to the radiation direction as an example of a plane intersected by the X-ray beam XB like FIG. 9b, showing a pattern to reduce, in accordance with scanning with the X-ray beam XB, the width of the X-ray beam XB in the height direction so that it is restricted sequentially in both top and bottom. FIG. 13b shows a pattern to change, in accordance with scanning with the X-ray beam XB, the width of the X-ray beam XB in the height direction to be smaller by sequentially decreasing only the width of a top end thereof while leaving the width of a bottom end as it is.

Changing the width of the X-ray beam XB in the height direction can be realized by controlling the width of the opening 12S in the height direction. The width of the opening 12S in the height direction can be set by the radiation area setting part 61b.

In actual radiography, the width of the X-ray beam XB in the height direction is changed to be expanded or reduced in accordance with a position and a shape of the radiography region of the object "O", and as a result, a panoramic X-ray image as shown in FIG. 14 can be taken.

The examples of FIGS. 13a and 13b are an example of changing the width of the X-ray beam XB in the height direction in accordance with scanning.

Figure 13C:
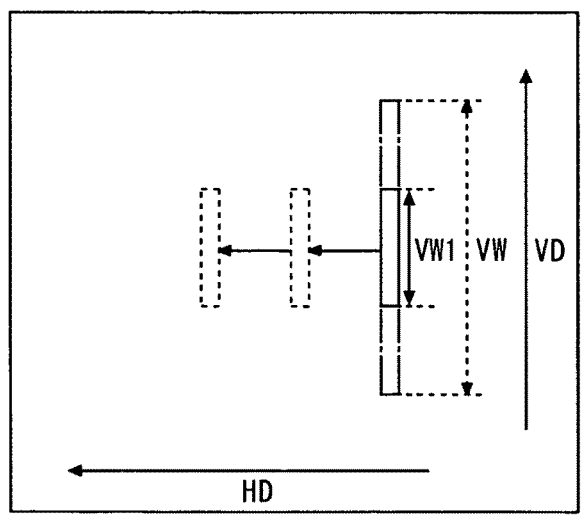

There may be an example as shown in FIG. 13c by utilizing the idea of restricting the width of the X-ray beam XB in the height direction in the implementation examples of FIGS. 9c, 13a and 13b.

In the example of FIG. 13c, the width of the X-ray beam XB is not changed in the height direction, but in comparison with conventional scanning with the X-ray beam XB, the width of the X-ray beam XB is restricted in the height direction so that only on the interested area "r" is irradiated.

The X-ray beam XB of FIG. 13c is seen from the front from the focus XF to the radiation direction in the detection surface 21a of the X-ray detector 21 as an example of a plane intersected by the X-ray beam XB like FIG. 9b.

In this scan control, a width VW1 of the X-ray beam XB in the height direction is restricted to be smaller than the width VW of the X-ray beam XB in the height direction according to the conventional scanning with the X-ray beam XB as shown in FIG. 9b. Scanning is directed to the scanning direction HD without changing the width VW1 in the height direction.

The X-ray beam XB can be thus irradiated only on the interested area "r". The position of the X-ray beam XB may be changed appropriately in accordance with the position of the interested area "r".

Although it is not shown, while restricting the X-ray beam XB as shown in FIG. 13c, the scanning direction may be changed to the height direction VD as shown in FIG. 9c.

FIG. 14 shows a panoramic X-ray image obtained in the third embodiment. A shaded portion in the figure is an area in which radiation of the X-ray beam XB is cut off like above.

When the panoramic X-ray image shown in this figure is compared to FIG. 11a obtained in the second embodiment, the X-ray radiation area is further cut off in a region from the left and right jaw joints to the front teeth part and the outside of the left and right jaw joints in the panoramic X-ray image of FIG. 14, and in comparison with the case of FIG. 11a, an area which contributes to the medical examination and an area which does not contribute to the medical examination are more strictly separated and exposure to X-ray is further reduced.

Figure 15A:
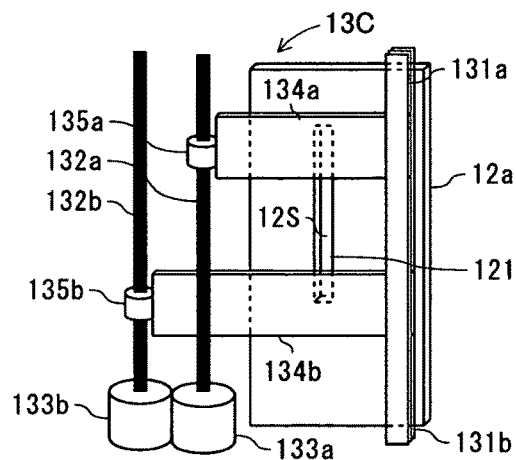
FIG. 15a to FIG. 15c show an example of the radiation area restricting part driving mechanism, respectively.
Figure 15B:
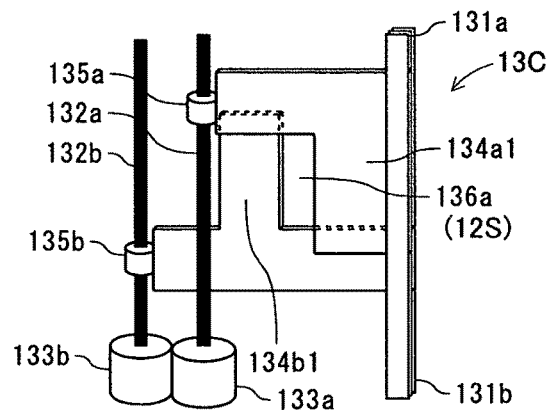
Figure 15C:
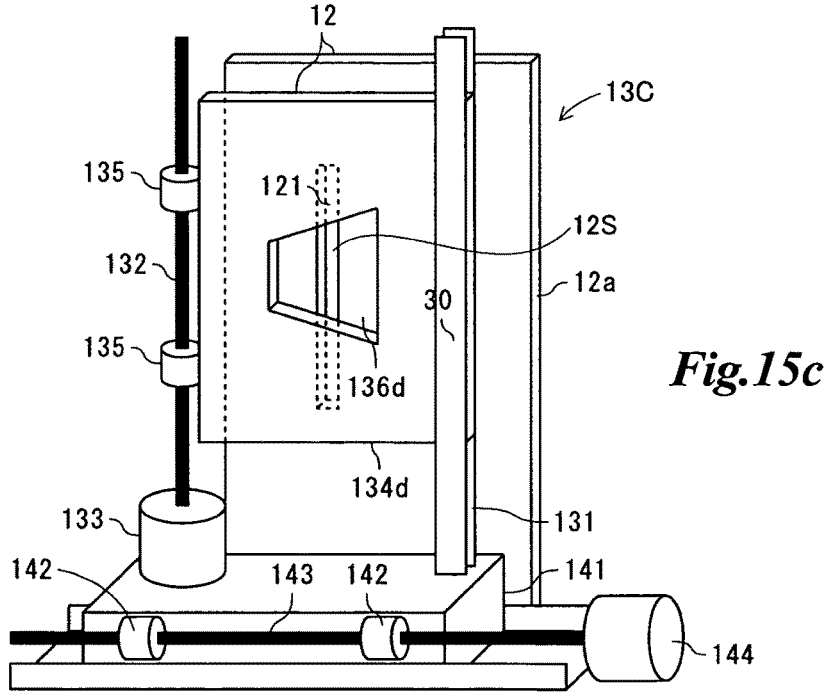

FIGS. 15a to 15c show examples of the radiation area restricting part driving mechanism used in the third embodiment. The third embodiment is characterized in that an X-ray radiation position changing part A is composed of a radiation area restricting part driving mechanism 13C, and any examples of the radiation area restricting part driving mechanism 13C are allowed to change the opening width of the opening freely in the height direction.

The radiation area restricting part driving mechanism 13C is an example of the radiation area restricting part driving mechanism 13.

The radiation area restricting part driving mechanism 13C shown in FIG. 15a is designed to combine the slit member 12a established with the opening 121 extending in the height direction and a pair of upper and lower shielding plates 134a and 134b arranged in parallel to each other relative to the opening, wherein the slit member 12a is fixed and the pair of the shielding plates 134a and 134b is fitted into correspondingly arranged guide grooves 131a and 131b in one end on the same side, respectively, and has female screw parts 135a and 135b each formed with a screw groove internally in the other end on the same side, respectively. These female screw parts 135a and 135b are screwed through and penetrated into rotary shaft 132a and 132b, each formed with a screw thread, of a pair of correspondingly arranged motors 133a and 133b, respectively.

The opening 121 of the slit member 12a in the height direction has a width which is the same as a width of a slit used for the conventional panoramic radiography.

Here, if the pair of the shielding plates 134a and 134b is moved in parallel so as to form a gap therebetween (at this time, the shielding plates 134a and 134b cover upper and lower ends of the opening 121, respectively), a superposed portion made by the gap generated at this time and the opening 121 established in the slit member 12a forms the opening 12S.

According to such a structure, the X-ray transmitting hole 12S can be expanded and narrowed in the longitudinal direction by supplying a control signal from the main body controlling part 60 to the two motors 133a and 133b and driving the respective motors 133a and 133b in combination, and moving the pair of the shielding plates 134a and 134b up and down. Therefore, at the time of scanning with the X-ray beam XB, in accordance with a radiography region of the object "O", a radiation position of the X-ray beam XB irradiated on the object "O" can be displaced along the height direction by changing an opening width of the opening 12S in the height direction with more detailed accuracy.

Note that the above-mentioned entire panoramic radiography may also be enabled by raising the shielding plate 134a and lowering the shielding plate 134b to move the opening 121 to a position in which the opening 121 is not blocked at all.

The shielding plates 134a and 134b are an example of the shielding part, and the slit member 12a and the shielding plates 134a and 134b serve as an example of the opening part in which the opening 12S for permitting part of X-ray to pass therethrough is formed.

The radiation area restricting part driving mechanism 13C shown in FIG. 15b does not use the slit member 12a as shown in FIG. 12a, and is designed to arrange two pieces of L-shape shielding plates 134a1 and 134b1 oppositely to each other so that an opening 136a is formed in the center therebetween, wherein female screw parts 135a and 135b each formed with a screw groove internally are arranged at respective ends of the two L-shape shielding plates 134a1 and 134b1 on the same side, and the female screw parts 135a and 135b are screwed through and penetrated into the rotary shaft 132a and 132b, each formed with a screw thread, of the two motors 133a and 133b, respectively.

In such a structure, the opening 136a formed in the center of the two shielding plates 134a1 and 134b1 can be used as the opening 12S, and therefore it can be the that the radiation area restricting part 12 is integrated in the structure.

Accordingly, by supplying a control signal from the main body controlling part 60 to the motors 133a and 133b and driving the respective motors 133a and 133b in combination, not only the opening 12S can be expanded and narrowed in the height direction, but also a position thereof can be changed in the height direction while maintaining a width thereof in the height direction, so that at the time of scanning with the X-ray beam XB, in accordance with a radiography region of the object "O", a radiation position of the X-ray beam XB irradiated on the object "O" can be displaced with more accuracy.

Here, the shielding plates 134a and 134b serve as the shielding part, and an example of the opening part in which the opening 136a (or 12S) for permitting part of X-ray to pass therethrough is formed.

In the radiation area restricting part driving mechanism 13C shown in FIG. 15C, the opening 121 extending in the height direction is combined with the established slit member 12a and a shielding plate 134d formed with an opening 136d, wherein the shielding plate 134d is arranged with a base board 141 downwardly and the base board 141 is arranged with a pair of female screw parts 142 and 142 each formed with a screw groove. Each of the female groove parts 142 and 142 is screwed through and penetrated into a rotary shaft 143, which is formed with a screw thread, of a motor 144.

In addition, one end of the shielding plate 134d is fitted into a guide groove and the other end thereof is arranged with a pair of the female screw parts 135 and 135 each formed with a screw groove, wherein each of the female screw parts 135 and 135 is screwed through and penetrated into the rotary shaft 132, which is formed with a screw thread, of the motor 133 fixed on the base board 141, and the opening 121 formed in the slit member 12a and the opening 136d formed in the shielding plate 134d are superposed to each other to form the opening 12S.

The opening 121 formed in the slit member 12a has a longitudinal shape, whereas the opening 136a formed in the shielding plate 134d has a trapezoidal shape with a dimension widely opened in a right side end rather than a left side end in the figure, so that if the shielding plate 134d is moved to the left direction by driving the motor 144 to turn and the opening 121 and the opening 136d are superposed to each other to form the transmitting hole 12S, the opening width of the opening 12S is increased in the height direction as it is moved, or if it is moved to the right direction in contrast, the opening width of the opening 12S is decreased in the height direction as it is moved.

Accordingly, the width of the opening 12S can be made wider or narrower in the height direction by supplying a control signal from the main body controlling part 60 to the two motors 133 and 144 and driving these motors 133 and 144 in combination, whereby at the time of scanning with the X-ray beam XB, in accordance with a radiography portion of the object "O", the object "O" can be irradiated by changing the width of the X-ray beam XB in the height direction with detailed accuracy.

Moreover, according to such a structure, a simple X-ray exposure preventing filter can be designed like the case of FIG. 12c by designing the shape of the opening 136d formed in the shielding plate 134d in alignment with the radiography region of the object "O".

Here, the shielding plate 134d is an example of the shielding part, and the slit member 12a and the shielding plate 134d serve as an example of the opening in which the opening 12S for permitting part of X-ray to pass therethrough is formed.

Note that, in the medical X-ray apparatus M according to the present embodiment, since the upper end position and the lower end position of the opening 12S can be displaced, using this structure makes it possible to select any of only the upper jaw, only the lower jaw and both upper and lower jaws as an object of partial panoramic radiography.

Figure 16A:
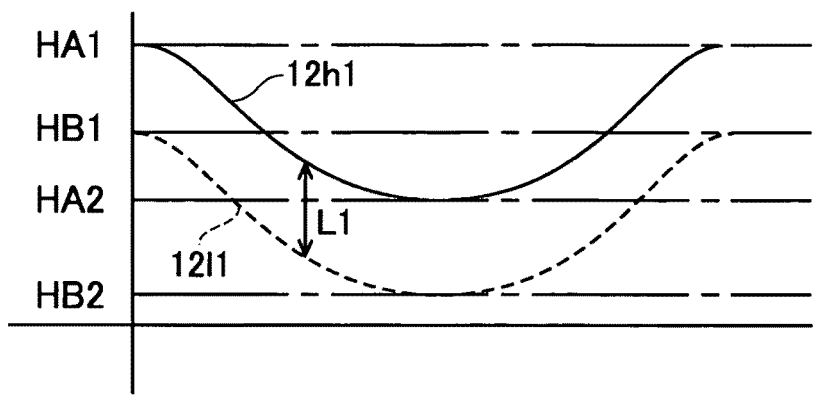
FIG. 16a to FIG. 16c shows the change in the height of the opening.
Figure 16B:
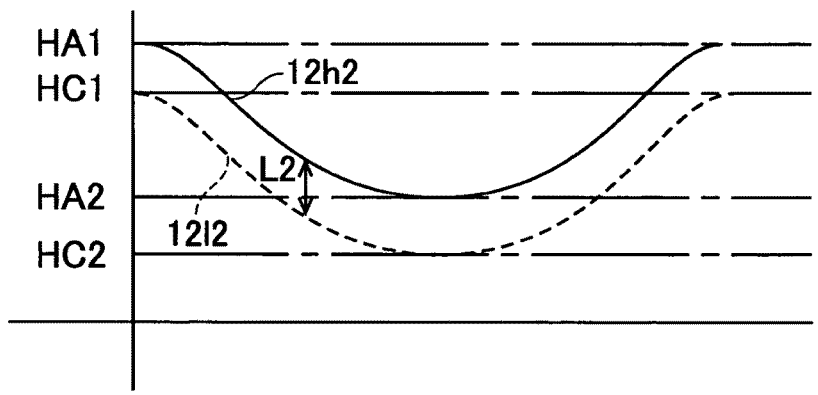
Figure 16C:
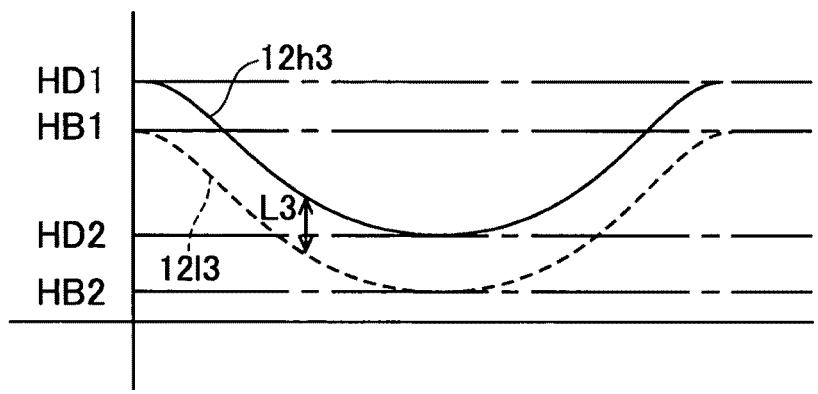

Panoramic radiography executed by selecting any of only the upper jaw, only the lower jaw and both upper and lower jaws is explained hereinafter with reference to FIGS. 16a to 16c. In FIGS. 16a to 16c, each of solid lines 12h1, 12h2 and 12h3 refers to a position in an upper end portion of the opening 12S, and each of broken lines 12l1, 12l2 and 12l3 refers to a position in a lower end portion of the opening 12S.

The positions in the upper end portion of the opening 12S correspond to, in the example of FIG. 15a for example, a lower end position of the shielding plate 134a, and the positions in the lower end portion of the opening 12S correspond to an upper end position of the shielding plate 134b.

If panoramic radiography is executed only for the upper jaw or the lower jaw, the radiation width of the X-ray beam XB, which is irradiated from the X-ray generator 11, in the height direction (or Z-axis direction) is narrowed by the radiation area restricting part 12 in comparison with the case of panoramic radiography executed for both upper and lower jaws. Namely, as shown in FIG. 16a, when panoramic radiography is executed for both upper and lower jaws, the height direction of the opening 12 (or the width in the Z-axis direction) which is formed by the radiation area restricting part 12 is set to a width L1. In contrast, as shown in each of FIGS. 16b and 16c, in the case of panoramic radiography for the upper jaw or the lower jaw, the height width of the opening (or the width in the Z-axis direction) which is formed by the slit member 12 is set to be a width L2 or L3 which is narrower than the width L1.

In FIG. 16a, if a radiation area of the X-ray beam XB falls in the jaw joint on the left side, the height position of the upper end portion of the opening 12S corresponds to the highest point HA1 and a highest position of the lower end portion thereof corresponds to a highest point HB1.

When the radiation area of the X-ray beam XB moves from the vicinity of the jaw joint on the left side to the vicinity of the front teeth, the height position of the upper end portion of the opening 12S is displaced to a lowest point HA2 and the height position of the lower end portion thereof is displaced to a lowest point HB2. When the radiation area of the X-ray beam XB moves to the jaw joint on the right side, the height position of the upper end portion of the opening 12S is displaced to the highest point HA1 and the height position of the lower end portion thereof is displaced to the highest point HB1.

In FIG. 16b, when the radiation area of the X-ray beam XB falls in the jaw joint on the left side, the height position of the upper end portion of the opening 12S corresponds to the highest point HA1 and the height position of the lower end portion thereof corresponds to a highest point HC1 which is positioned higher than the above-mentioned highest point HB1.

When the radiation area of the X-ray beam XB moves from the vicinity of the jaw joint on the left side to the vicinity of the front teeth, the height position of the upper end portion of the opening 12S is displaced to the lowest point HA2 and the height position of the lower end portion thereof is displaced to a lowest point HC2 which is positioned higher than the above-mentioned lowest point HB2.

The highest point HC1 and the lowest point HC2 are made to correspond to lower end positions of the dental arch of the upper jaw, respectively.

When the radiation area of the X-ray beam XB moves to the jaw joint on the right side, the height position of the upper end portion of the opening 12S is displaced to the highest point HA1 and the height position of the lower end portion thereof is displaced to the highest point HC1.

Note that, for simplification of explanation, only the upper jaw is subjected to panoramic radiography, but the upper jaw in an area with the presence of the teeth is set as a main radiography object, and if the vicinity of the jaw joint with no presence of the teeth is subjected to radiography, the X-ray beam XB is irradiated on an upper end portion of the mandible such as the head of the lower jaw.

In FIG. 16c, when the radiation area of the X-ray beam XB falls in the jaw joint on the left side, the height position of the upper end portion of the opening 12S corresponds to a highest point HD1 which is positioned lower than the above-mentioned highest point HA1, and the height position of the lower end portion thereof corresponds to the highest point HB1.

When the radiation area of the X-ray beam XB moves from the vicinity of the jaw joint on the left side to the vicinity of the front teeth, the height position of the upper end portion of the opening 12S is displaced to a lowest point HD2 which is positioned lower than the highest point HA2 and the height position of the lower end portion thereof is displaced to the lowest point HB2.

The highest point HD1 and the lowest point HD2 are made to correspond to upper end positions of the dental arch of the lower jaw, respectively.

When the radiation area of the X-ray beam XB moves to the jaw joint on the right side, the height position of the upper end portion of the opening 12S is displaced to the highest point HD1 and the height position of the lower end portion thereof is displaced to the highest point HB1.

Note that, for simplification of explanation, only the lower jaw is subjected to panoramic radiography, but the lower jaw in an area with the presence of the teeth is set as a main radiography object, and if the vicinity of the jaw joint with no presence of the teeth is subjected to radiography, the X-ray beam XB is irradiated on a lower end portion of the mandible.

The highest point HC1 in FIG. 16b and the highest point HD1 in FIG. 16c may coincide with the lowest point HC2 in FIG. 16b and the lowest point HD2 in FIG. 16c in terms of height.

As mentioned above, when any one of panoramic radiography for only the upper jaw or only the lower jaw and panoramic radiography for both upper and lower jaws is designated by the operating part 66 (refer to FIG. 2), the main controlling part 61 causes the radiation area setting part 61b (refer to FIG. 2) to determine the width L1 or L2 or L3 of the opening height in the radiation area restricting part 12 so that the height position of the X-ray beam XB irradiated on the object "O" is determined.

By thus changing the height width of the opening 12, it is made possible in the present embodiment to select any one of panoramic radiography for only the upper jaw or only the lower jaw and panoramic radiography for both upper and lower jaws. Then, if panoramic radiography is executed for only the upper jaw or only the lower jaw by narrowing the width of the opening height width of the opening 12, the height position of the radiation area restricting part 12 is adjusted by the radiation area restricting part driving mechanism 13, whereby any one of panoramic radiography for only the upper jaw and panoramic radiography for only the lower jaw can be selected.

Figure 17A:
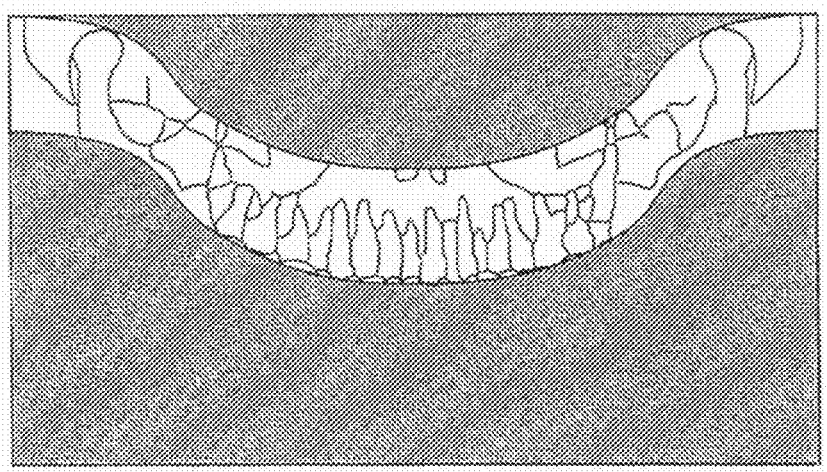
FIG. 17a shows the radiography objective area of panoramic radiography on the upper jaw.
Figure 17B:
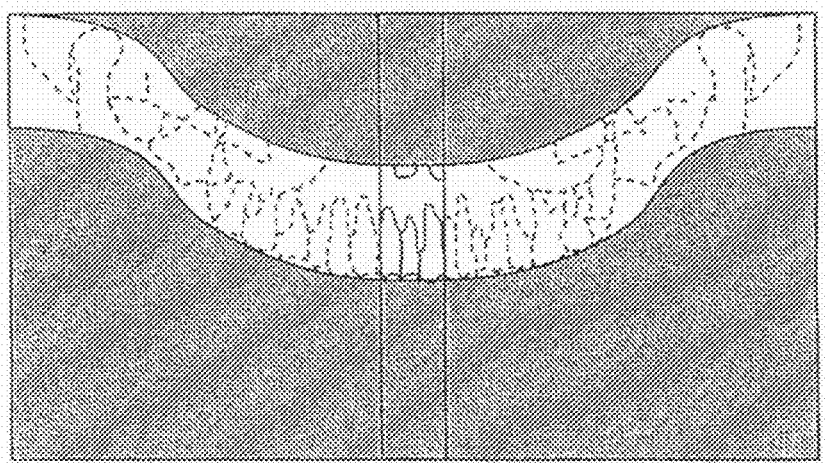
FIG. 17b shows the radiography objective area when the X-ray radiation area is further restricted.

FIG. 17a shows a radiography objective area in panoramic radiography (panoramic radiography objective area) for the upper jaw whose image is taken by a control of FIG. 16b, wherein a shaded portion in the figure refers to an area without radiation due to restriction of X-ray radiation. FIG. 17b shows how the X-ray radiation range is further restricted in the scanning direction of the X-ray beam XB under a control of FIG. 17a and the example in the figure shows X-ray radiation only in the vicinity of the front teeth.

Figure 18A:
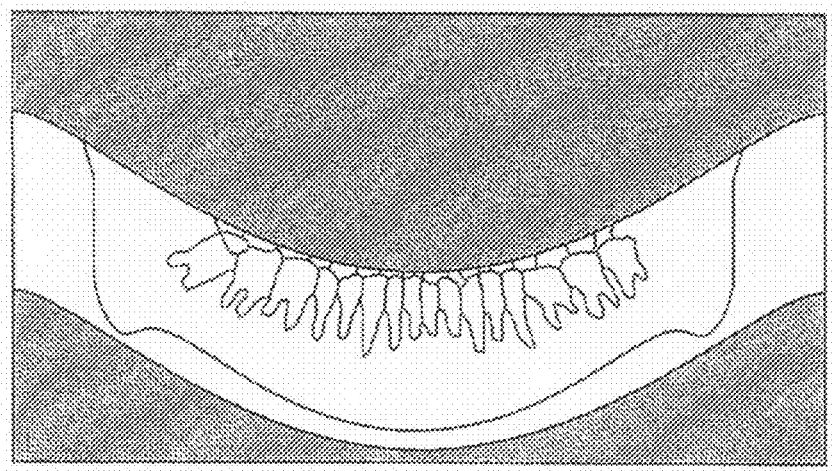
FIG. 18a shows the radiography objective area of panoramic radiography on the lower jaw.
Figure 18B:
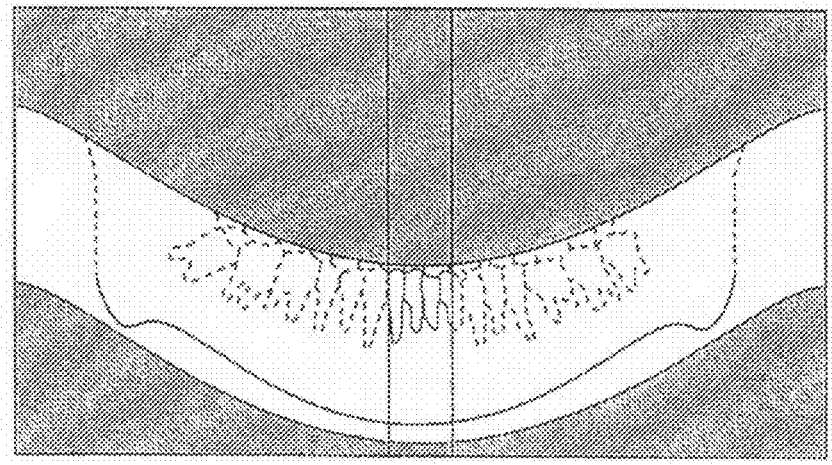
FIG. 18b shows the radiography objective area when the X-ray radiation area is further restricted.

FIG. 18a shows a radiography objective area in panoramic radiography (panoramic radiography objective area) for the lower jaw whose image is taken by a control of FIG. 16c, wherein a shaded portion in the figure refers to an area without radiation due to restriction of X-ray radiation. FIG. 18b shows how the X-ray radiation range is further restricted in the scanning direction of the X-ray beam XB under a control of FIG. 18a and the example in the figure shows X-ray radiation only in the vicinity of the front teeth.

The position of the opening 12S may not always vertically move between H1 and H2 in height direction while the supporting part 30 is turned, and the position of the opening 12S may not be changed during radiography at each region even though the position of the opening 12S is changed at each region.

For example, X-ray may be irradiated only on the upper part of the left jaw joint or only on the upper part of the right jaw joint with the upper end portion of the opening 12S at position HA1 and the lower end portion thereof at position HC1 in height direction or X-ray is irradiated only on the front teeth of the lower jaw with the upper end portion of the opening 12S at position HD2 and the lower end portion thereof at position HB2 in height direction keeping the height at fixed position during the radiography.

Thus the partial panoramic radiography each of above region (for single region) can be executed for example.

Plural region may be set for which serial X-ray radiation for each of them are executed.

For example, X-ray may be irradiated on the upper part of the left jaw joint with the opening 12S fixed at above mentioned position, and next the position of the opening 12S is changed, continually, X-ray is irradiated on the front teeth of the lower jaw at above mentioned position.

Of course the regions may be not limited only two regions, three or more regions including entire area in total are available.

Furthermore, only a specific tooth may also be set as a radiography object by setting at least one position of both end of the width of the scanning direction intersecting the height direction of the radiation area of the X-ray beam XB as a desired position.

Figure 1A:
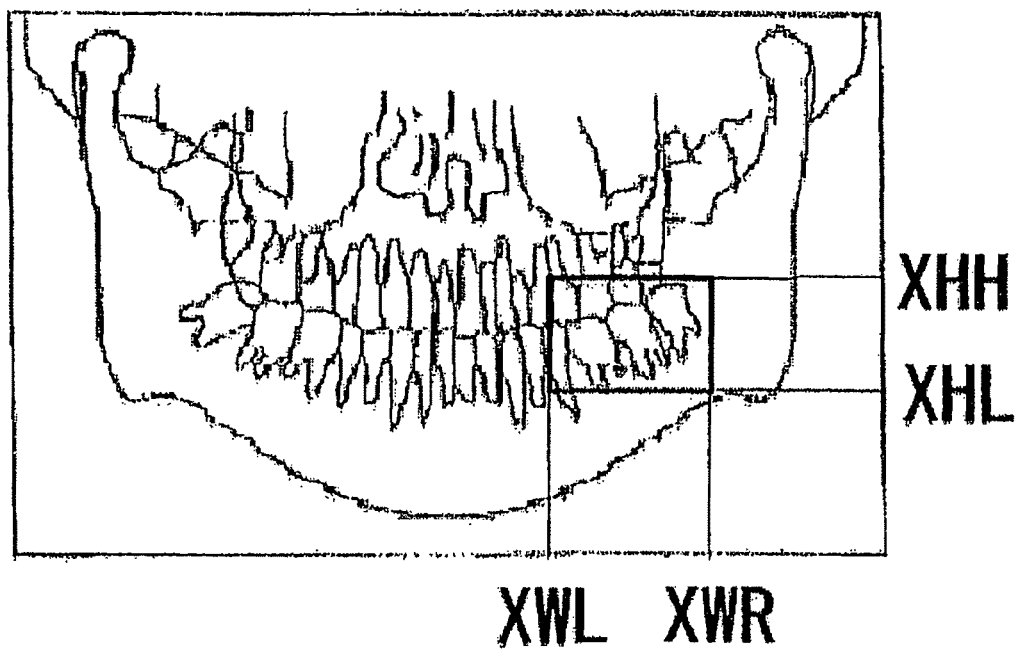
FIG. 1A shows the radiography objective area of partial panoramic radiography.
Figure 1B:
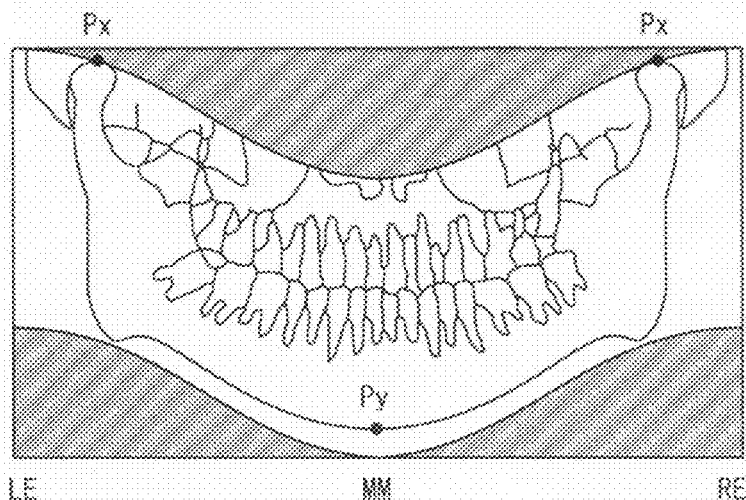
FIG. 1Ba is an example of the panoramic X-ray image of the entire jaw obtained in the present invention, and FIG. 1Bb shows the change in the height of the opening of the radiation area restricting part for obtaining the image.
Figure 1B:
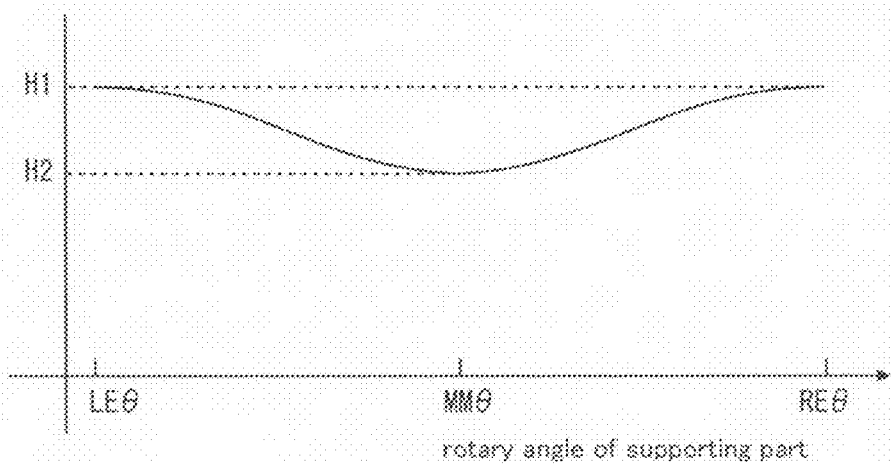

In such partial panoramic radiography, a schematic panoramic X-ray image of the lower jaw or a schematic image of the dental arch is displayed on the displaying part 67, and the operating part 66 is operated to specify a local region being a radiography object on the schematic image. At this time, by designating one point, a predetermined rectangle including the one point as a center may be set as a radiography objective area. Alternatively, four corners of a rectangle which should be a radiography objective area may also be designated. For example, if a partial panoramic X-ray image of an area in the vicinity of the molar on the right side of the lower jaw is necessary, a radiography objective area may be set as shown in FIG. 1A. In addition, regions to be considered as a radiography objective area include, for example, the front teeth of the upper jaw, the front teeth of the lower jaw, the molars of the upper jaw, the molars of the lower jaw and other regions, and any of these regions can be set as a radiography objective area.

Here, when information on the specified radiography objective area is supplied to the main controlling part 61, the main controlling part 61 sets a start position and an end position of radiography in the scanning orbit of the supporting part 30, and causes the radiation area setting part 61b to determine an opening height width and a height position in the radiation area restricting part 12.

In the partial panoramic radiography as shown in FIG. 1A, the height width and the height position of the opening 12S are maintained to be a calculated value during partial panoramic radiography. Namely, coordinates XHL and XHH of the height position are constant. Projection of the X-ray beam XB may be accepted in a section between a coordinate XWL of the start position calculated above and a coordinate VWR of the end position. The supporting part 30 may also be driven throughout the entire radiography orbit or only in a range with an approach section added before and after the section including the start position and the end position.

In such partial panoramic radiography, a minimum range required for the medical examination can be optionally set as a radiography objective area and it is possible to reduce the exposure by irradiating X-ray only on the area. Particularly when the height direction is restricted with restriction of the scanning direction as shown in FIG. 1A, an effect of reducing the exposure is large.

Figure 19A:
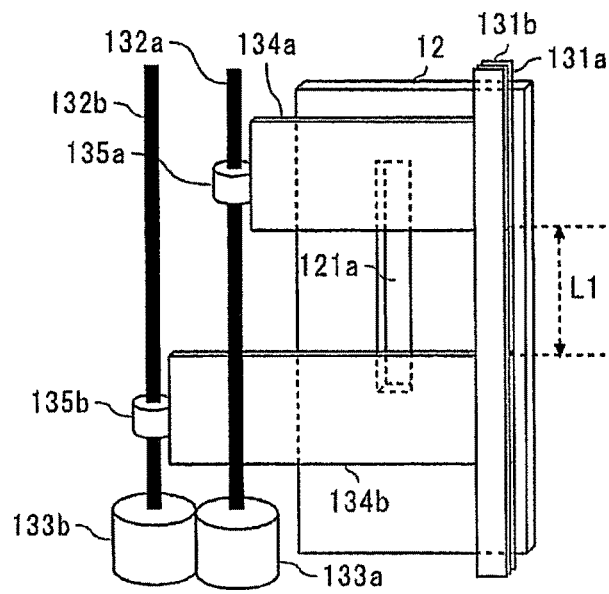
FIG. 19a and FIG. 19b show the operating conditions of the radiation area restricting part driving mechanism, respectively.

In the medical X-ray apparatus MA according to the present embodiment, the radiation area restricting part 12 and the radiation area restricting part driving mechanism 13 can be structured as shown in FIG. 19a in the same mariner with FIG. 15a. Namely, by providing the shielding members 134a and 134b which are displaced independently in the height direction (or Z-axis direction), a height width between the shielding members 134a and 134b (or the width in the Z-axis direction) can be set to either the width L1 or L2. In other words, when both upper and lower jaws are subjected to panoramic radiography, a height width between the shielding members 134a and 134b is set to the width L1 as shown in FIG. 19a. In the case of panoramic radiography for the upper jaw, a height width between the shielding members 134a and 134b is set to the width L2 as shown in FIG. 19b.

Figure 19B:
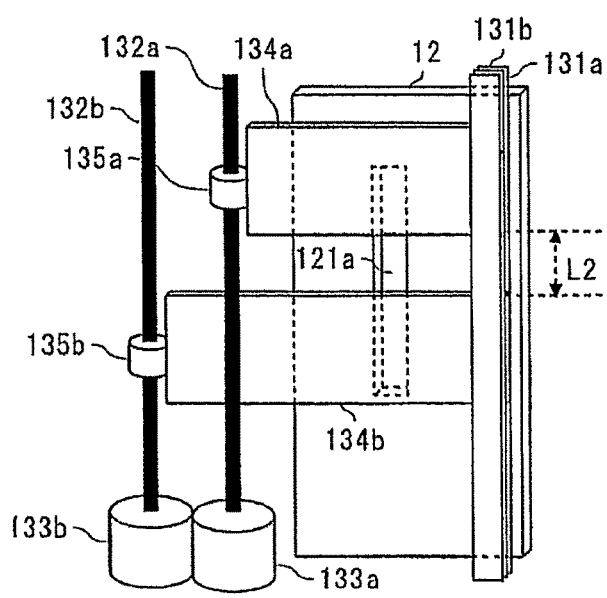

In the case of radiography for the lower jaw, the height width between the shielding members 134a and 134b is set to the width L3 like FIG. 19b, thought it is not shown.

Figure 20A:
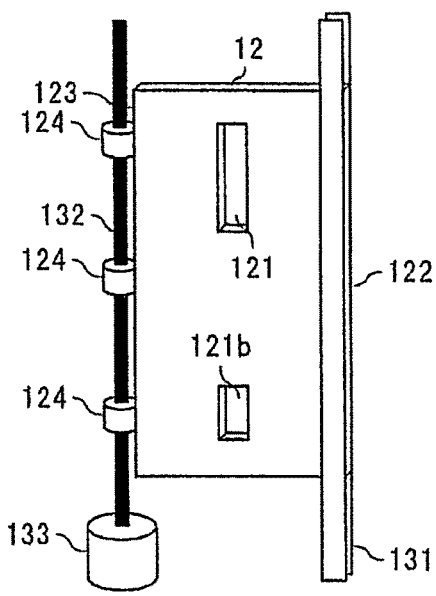
FIG. 20a and FIG. 20b show other radiation area restricting part driving mechanism, respectively.

Also, as a modified example of the present embodiment, the radiation area restricting part 12 and the radiation area restricting part driving mechanism 13 may also be, other than the above-mentioned structure of FIG. 19a, in a structure as shown in FIG. 20a. Namely, the radiation area restricting part 12 is structured so that the opening 121 whose height width is the width L1 and the opening 121b whose height width is the width L2 are arranged side by side on a straight line in the Z-axis direction. Owing to such a structure, any one of the openings 121 and 121b may be selected as an opening for permitting the X-ray beam XB to pass therethrough by using a slit moving mechanism 13 to turn a screw axis 132 by the motor 133 and displace the radiation area restricting part 12 in the height direction. Note that, in such a structure, if the opening height position of any one of the selected openings 121 and 121b is displaced by a panoramic radiography operation, it is set to a position in which the X-ray beam XB emitted from the X-ray generator 11 does not leak from the other opening.

Figure 20B:
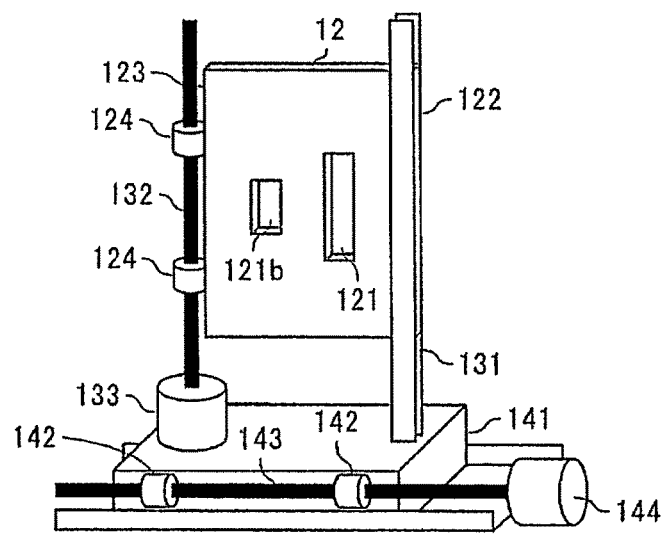

Furthermore, as shown in FIG. 20b, the radiation area restricting part 12 may also be structured so that the opening 121 whose height width is the width L1 and the opening 121b whose height width is the width L2 are arranged side by side in a vertical direction (or horizontal direction) relative to the Z-axis direction. Then, the X-ray detecting part 10 is provided with a pedestal part 141 for arranging the slit moving mechanism 13 including a rail groove 131, the screw axis 132 and the motor 133, and the radiation area restricting part 12. The pedestal part 141 has a female screw part 142 which is screwed through a screw axis 143 whose axial direction falls in the horizontal direction. Then, the motor 144 is provided to turn the screw axis 143. Owing to such a structure, the screw axis 143 is turned by the motor 144 to move the pedestal part 141 to the horizontal direction in which the openings 121 and 121b are arranged side by side. Displacement of the pedestal part 141 is followed by movement of the radiation area restricting part 12 to the horizontal direction, whereby any one of the openings 121 and 121b is selected as an opening for permitting the X-ray beam XB emitted from the X-ray generator 11 to pass therethrough.

Figure 21:
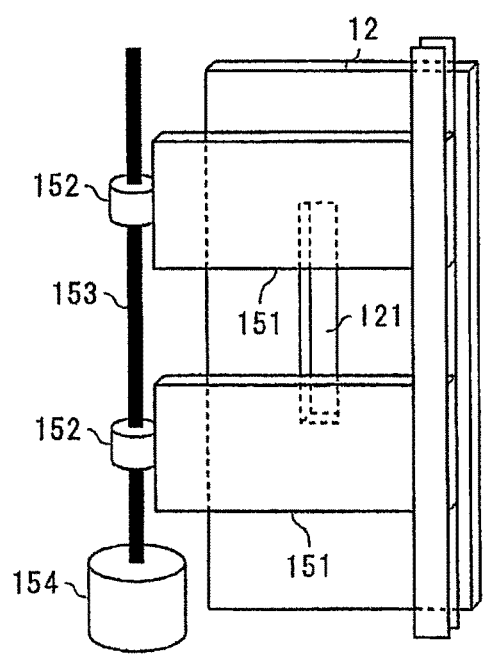
FIG. 21 shows other radiation area restricting part driving mechanism.

In addition, as shown in FIG. 21, there may also be a structure to arrange, in front of the radiation area restricting part 12 having the opening 121, two of shielding members 151 each provided with a female screw part 152 screwed through a screw axis 153. At this time, respective screw grooves of the female screw parts 152 of the shielding members 151 which are arranged in upper and lower spaces in the height direction (or Z-axis direction) are directed oppositely to each other. The screw axis 153 is designed so that a screw groove is directed oppositely in an area through which each of the female screw parts 152 is screwed. Therefore, when the screw axis 153 is turned by the motor 154, the two shielding members 151 are displaced simultaneously so as to be symmetrical, along the height direction (or Z-axis direction), relative to the center of the opening 121 of the radiation area restricting part 12. The two shielding members 151 are thus displaced simultaneously in the height direction so as to change a height width formed by the two shielding members 151, so that the height width of the radiation area of X-ray emitted from the X-ray generating part 10 can be changed.

Figure 6:
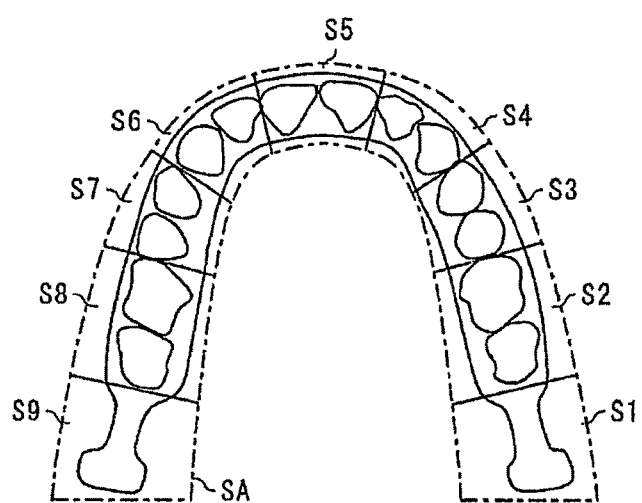
FIG. 6 shows the dental arch in which the curved sectional plane area is divided into a plural divisions.

Note that, in the above-mentioned first and second embodiments, the height position of the opening 12S set by the radiation area restricting part 12 is displaced continuously in panoramic radiography in accordance with a rotary angle of the supporting part 30, but it may be displaced stepwise. For example, as shown in FIG. 6, when the dental arch S is a radiography object and the curved sectional plane area SA is divided into a plurality of areas S1 to S9, the opening 12S is preset to height positions HA1 to HA9 corresponding to the areas S1 to S9, respectively. Owing to such operation, if any area Sn (n is a natural number of any of 1 to 9) is designated as a local area for partial panoramic radiography, partial panoramic radiography can be executed while the opening 12S is fixed to a height position HAn.

According to the present embodiment, an X-ray image similar to a conventional intraoral radiography image which is familiar to the doctor can be generated by partial panoramic radiography through X-ray radiation on the same range as a radiography area of the conventional intraoral radiography image.

<Fourth Embodiment>

A fourth embodiment of the medical X-ray apparatus according to the present invention is explained hereinafter with reference to drawings.

Figure 22:
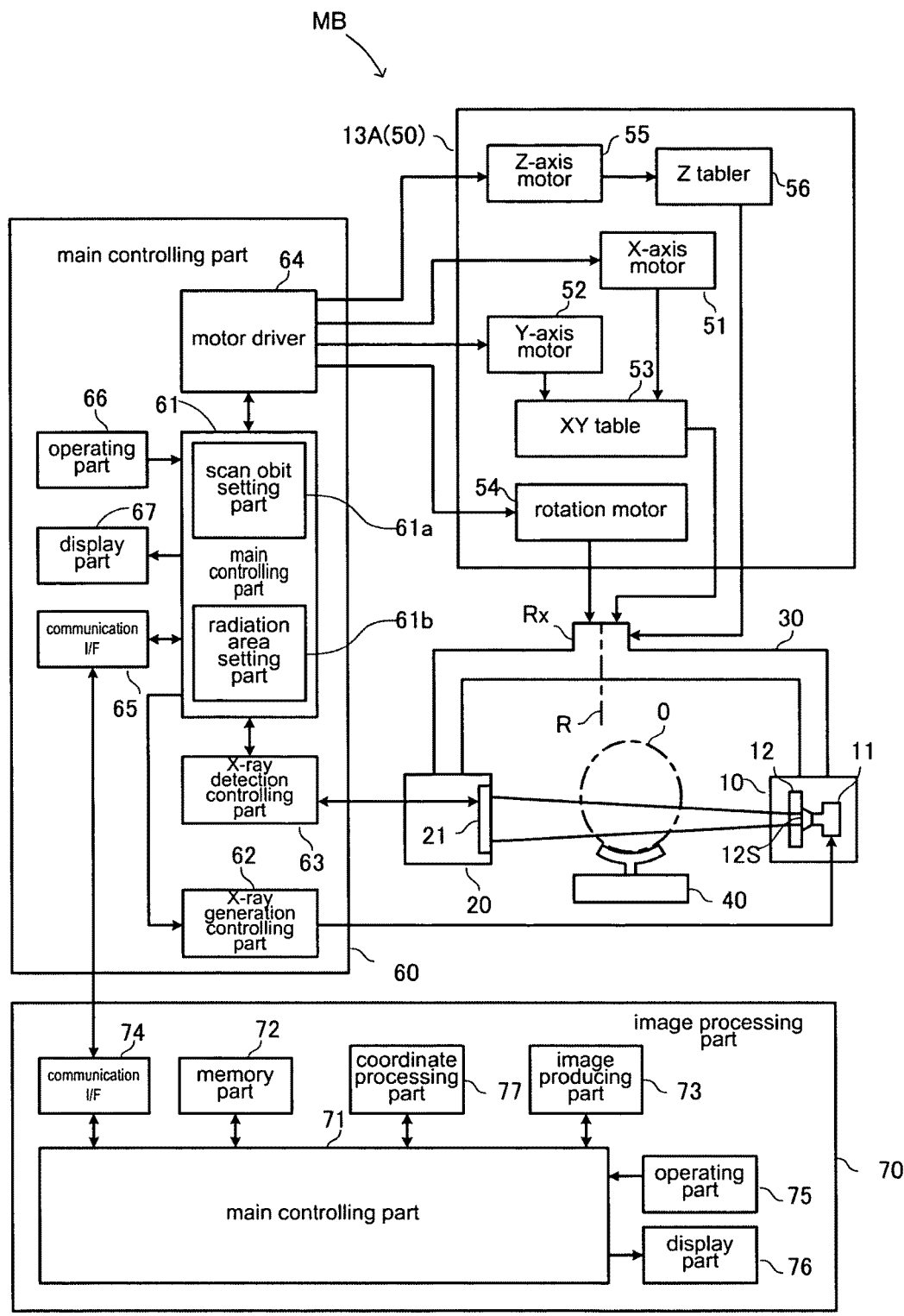
FIG. 22 shows a diagrammatic structure of other medical X-ray apparatus of the present invention.

FIG. 22 is a block diagram showing a basic structure of a medical X-ray apparatus MB.

This embodiment is characterized by controlling an X-ray radiation area by a supporting part moving mechanism. In the example of FIG. 22, a supporting part moving mechanism 13A is structured to further include the scan driving part 50, wherein the same reference numbers refer to parts used for the same purpose as the medical X-ray apparatus M shown in FIG. 1 and detailed explanation thereof is omitted.

The medical X-ray apparatus MB according to the present embodiment has the supporting part moving mechanism 13A, and the support moving mechanism 13A includes the rotary motor 54 for rotating the supporting part 30, a Z-axis motor 55 for displacing the supporting part 30 in the height direction (or Z-axis direction), and a Z-axis table 56 driven by the Z-axis motor 55 to displace the supporting part 30 in the height direction. The Z-axis motor 55 is turned in response to a control signal sent from a motor driver 64 provided in the main body controlling part 60, and drives the Z-axis table 56 to displace the supporting part 30 in the height direction (or Z-axis direction). The radiation area restricting part 12 which is composed of a slit member and the like is fixed in the X-ray generating part 10, which differs from the second embodiment.

The main controlling part 61 includes the scan orbit setting part 61a for setting the scan orbit of the supporting part 30, and the radiation area setting part 61b, and if a radiography area of the object "O" is specified by the above-mentioned profile information or other information, a program using CPU is executed to specify a scan orbit of the X-ray beam XB at the time of scanning, whereby the above-mentioned scan control of the X-ray beam XB is achieved.

Namely, in the fourth embodiment, CPU arranged in the main controlling part 61 calculates a scan orbit of the supporting part 30 by reading profile information and sets the calculated scan orbit in the scan orbit setting part 61a, while the radiation area setting part 61b is set to have a radiation position of the X-ray beam XB corresponding to a radiography region of the object "O" at the time of scanning with the X-ray beam XB, wherein the main controlling part 61 transmits, based on these set information, a control signal to the motor driver 64 to actuate the supporting part moving mechanism 13A. As a result, the supporting part moving mechanism 13A is moved up and down in the height direction in accordance with a radiography region of the object "O" while rotating the supporting part 30, whereby the X-ray beam XB emitted from the opening 12S is irradiated only on the radiography region of the object "O".

Figure 23:
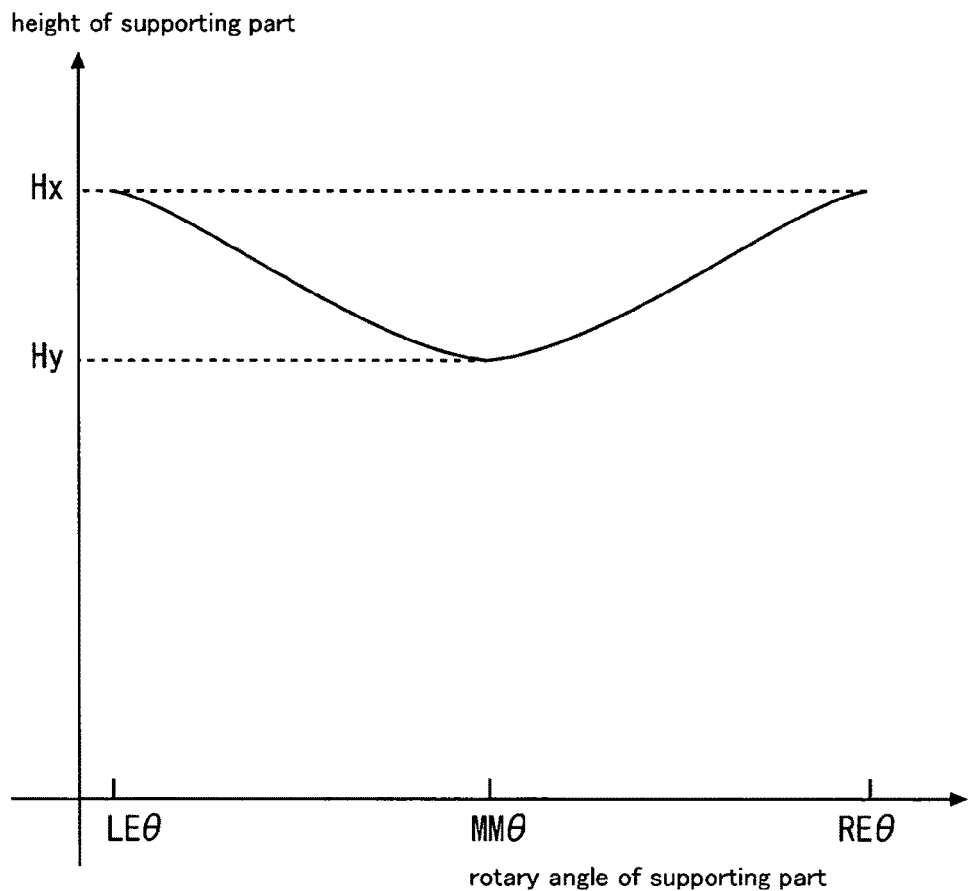
FIG. 23 shows the change in the height of the supporting part.
Figure 24A:
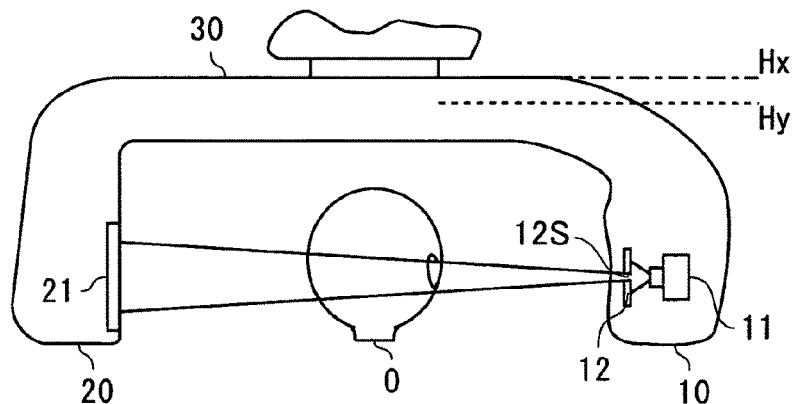
FIG. 24 shows the positional relation of the supporting part and the object to be examined.
Figure 24B:
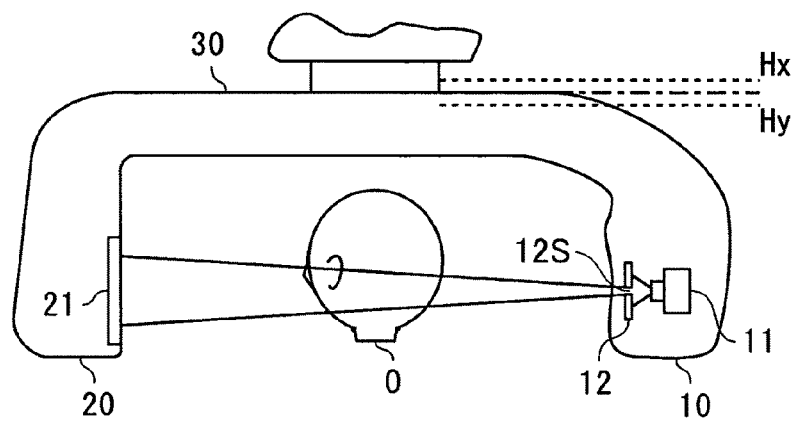
Figure 24C:
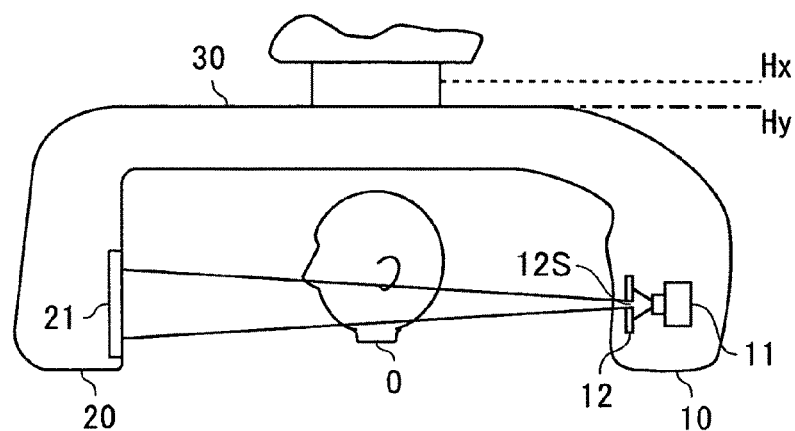

FIG. 23 shows, when panoramic radiography is executed in the third embodiment, a height position of the supporting part 30 at the time of scanning with the X-ray beam XB, which moves up and down, is made to correspond to a rotary angle of the supporting part 30 by the supporting part driving mechanism. FIGS. 24a to 24c show a positional relationship between the supporting part 30 and the object "O" at the time of scanning with the X-ray beam XB, in correspondence to a rotary operation of the supporting part 30.

When panoramic radiography is executed for the entire jaw of the object "O", according to the present embodiment, the supporting part 30 is moved to a highest point Hx in an area of the left and right jaw joints and moved to a lowest point Hy in an area of the front teeth, while rotating around the object "O", so that the supporting part 30 moves up and down continuously between the highest point Hx and the lowest point Hy.

Rotational movement of the supporting part 30 from LEθ to MMθ to REθ is similar to FIG. 11b and description thereof is omitted.

At this time, the object "O" and the opening 12S provided in the radiation area restricting part 12 are in a fixed state, but the object "O" and the opening 12S may also be moved up and down simultaneously, or in short, during scanning with the X-ray beam XB, they can be in any states as long as a radiation range is not expanded inadvertently by deviation of a radiation position of the X-ray beam XB from a radiography region of the object "O".

Note that, in the present embodiment, the supporting part driving mechanism 13A may also be structured by, rather than being structured to move the rotary shaft Rx of the supporting part 30 up and down directly, a mechanism to lift lifting means which is arranged to pivot the supporting part 30 and lift the supporting member 30 as a whole.

Figure 26:
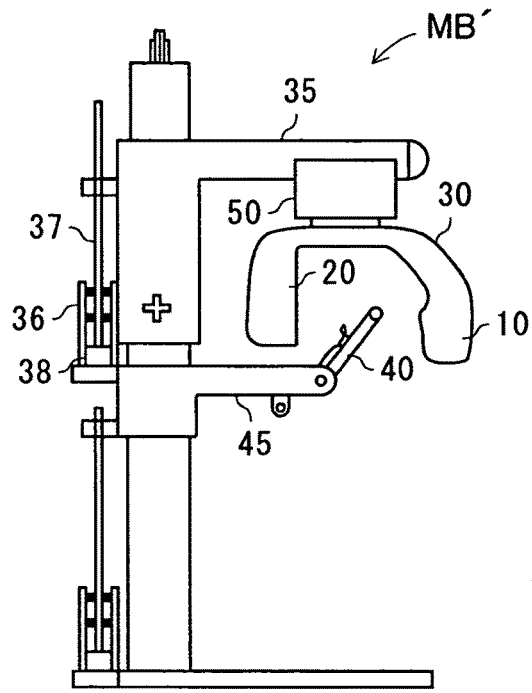
FIG. 26 is a side view of the medical X-ray apparatus of the present invention.

FIG. 26 shows a medical apparatus MB' in which a lifting arm 35 being the lifting means for pivoting the supporting part 30 and lifting the supporting part 30 as a whole is lifted in the height direction relative to the patient frame 45 which is connected to the object holding part 40, wherein a Z-axis moving mechanism 36 is interposed between the lifting arm 35 and the patient frame 45.

The Z-axis moving mechanism 36 may also be structured to have a screw axis whose axial direction is the Z-axis direction (or height direction) and turn the screw axis by a motor.

In such a structure, an X-ray radiation area for the object "O" can be displaced in the height direction by driving the Z-axis moving mechanism 36 to displace and lift the height position of the lifting arm 35 relative to the patient frame 45, while irradiating the X-ray beam XB on the object "O" for radiography.

Figure 25A:
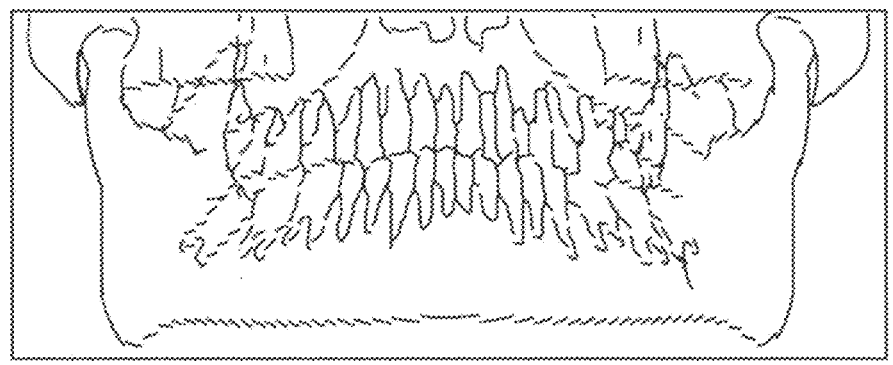
FIG. 25a and FIG. 25b show an example of panoramic X-ray image obtained in the present invention.
Figure 25B:
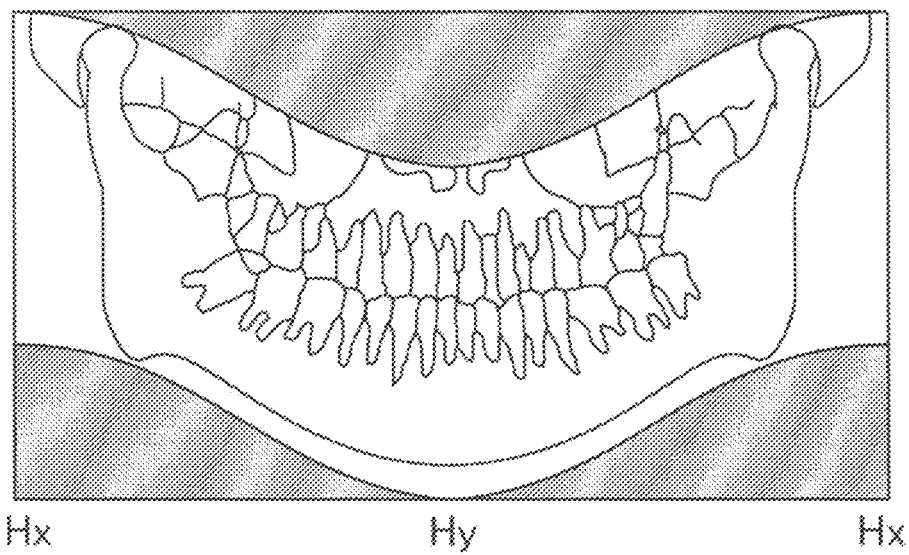

FIGS. 25a and 25b show panoramic X-ray images obtained in the third embodiment.

The width of the X-ray beam XB to be irradiated in the height direction is restricted more than the conventional panoramic radiography and radiography is executed with a width suitable of the interested area "r". To this restriction, it is possible to apply, for example, the structure of the radiation area restricting part 12 used in the second and third embodiments.

When X-ray transmitted images generated by the X-ray detector 21 through radiation of the X-ray beam XB are combined as they are and placed side by side, the generated images produce a panoramic X-ray image as shown in FIG. 25a by ignoring the position in the height direction. Therefore, the image producing part 73 makes a positional correction in the height direction and, as a result, a panoramic X-ray image with radiography regions arranged in a natural height position is generated as shown in FIG. 25b.

Note that, in the present embodiment, similar to the second embodiment, when panoramic radiography is executed, the structure to change the height width of the opening 12S may be employed or the structure to enable selection of both upper and lower jaws and only any one thereof may also be employed.

Namely, when panoramic radiography is executed for both upper and lower jaws, a height width of the opening 12S is set to the width L1 and the height position of the supporting member 30 is displaced as shown in FIG. 23 in accordance with a rotary angle of the supporting part 30. In addition, when panoramic radiography is executed for only the upper jaw, a height width of the opening 12S is set to the width L2 and, similar to the case of panoramic radiography for both upper and lower jaws, the height position of the supporting part 30 is displaced in accordance with a rotary angle of the supporting part 30 as shown in FIG. 23. Then, in panoramic radiography executed for only the lower jaw, the height width of the opening 12S is set to the width L3 and the height position of the supporting part 30 is displaced, in accordance with a rotary angle of the supporting part 30, in a position lower than the case of panoramic radiography for only the upper jaw.

If it is thus structured to displace the height position of the supporting part 30, the radiation area restricting part 12 may also be designed to arrange the openings 121 and 121b, each having a different height width, side by side in the Z-axis direction as shown in FIG. 20a, or arrange the openings 121 and 121b side by side in the horizontal direction (or a direction vertical to the Z-axis direction) as shown in FIG. 20b. If the openings 121 and 121b are arranged side by side in the Z-axis direction as shown in FIG. 20a, an opening used for panoramic radiography is selected by sliding the radiation area restricting part 12 in the Z-axis direction. In contrast, if the openings 121 and 121b are arranged side by side in the horizontal direction as shown in FIG. 20b, an opening used for panoramic radiography is selected by sliding the radiation area restricting part 12 in the horizontal direction.

By employing the structure of the radiation area restricting part 12 of FIG. 20 in which the respective screw grooves of the female screw parts 152 of the shielding members 151 are directed oppositely to each other, the width of the X-ray beam XB may also be designed to be variable in the height direction while displacing the height of a radiation area.

<Fifth Embodiment>

A fifth embodiment of the medical X-ray apparatus M according to the present invention is explained hereinafter with reference to drawings.

The present embodiment is structured to move the X-ray generator 11 and the radiation area restricting part 12 integrally, while the object "O" and the supporting part 30 are in a fixed state.

Figure 27:
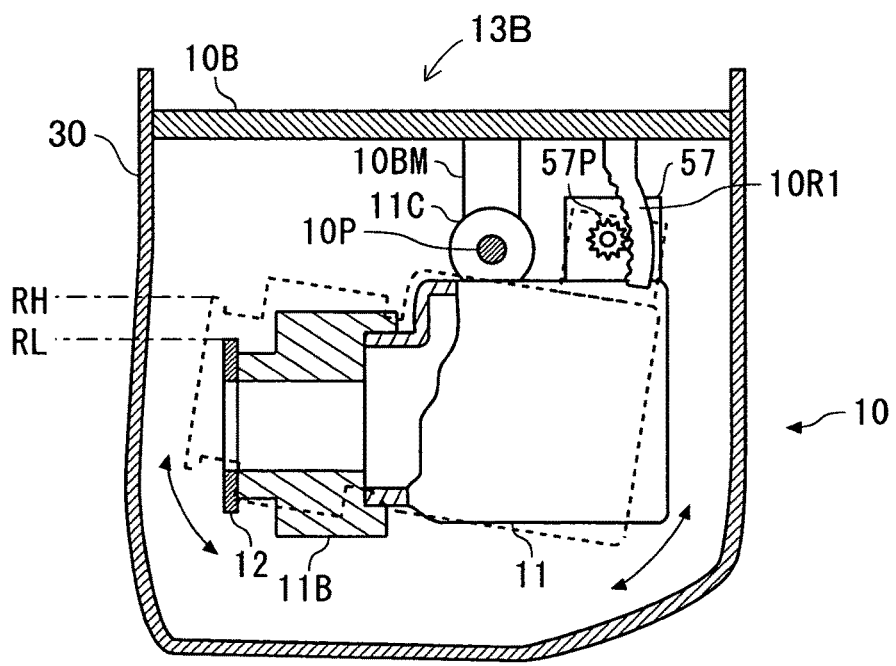
FIG. 27 is a partially broken view of the X-ray generating part.

FIG. 27 shows a schematic structure of the X-ray generating part 10 which is an essential part of the present embodiment.

A base part 10B extending from the supporting part 30 to the X-ray generating part 10 has a beam part 10BM suspended therefrom and includes a shaft 10P on the top end thereof. In the X-ray generator 11, the radiation area restricting part 12 is fixed via a hollow block 11B and a bearing 11C through which the shaft 10P is penetrated is fixed on the top thereof, wherein the bearing 11C can turn around the shaft 10P.

An arc-shaped rack 10R1 whose center of an arc coincides with the shaft center of the shaft 10P is also arranged in the base part 10B, a motor 57 is fixed to the top of the X-ray generator 11, and a pinion 57P engaged with the rack 10R1 is fixed to a rotary shaft of the motor 57.

According to such a structure, if the motor 57 is driven to turn, the pinion 57P is moved while being turned on the rack 10R1, and the movement is accompanied by turn of the X-ray generator 11 by using the shaft 10P as a center.

Accordingly, if the X-ray beam XB is irradiated on the object "O" and the X-ray generator 11 is driven rotationally while rotating the supporting part 30, the turn of the X-ray generator 11 is accompanied by displacement of the radiation area restricting part 12 in a direction from a low position RL to a high position RH, not shown, or in a reverse direction, so that a height direction of X-ray beam XB restricted by the radiation area restricting part 12 can also be displaced in the height direction.

In addition, in this embodiment, a mechanism including a combination of the shaft 10P, the bearing 11C, the motor 57, the rack 10R1, the pinion 57P, the X-ray generator 11, the radiation area restricting part 12, and the block 11B constitutes the radiation area restricting part driving mechanism 13B.

This embodiment is characterized in that the radiation area restricting part driving mechanism 13B constitutes the X-ray radiation position changing part A.

Figure 28:
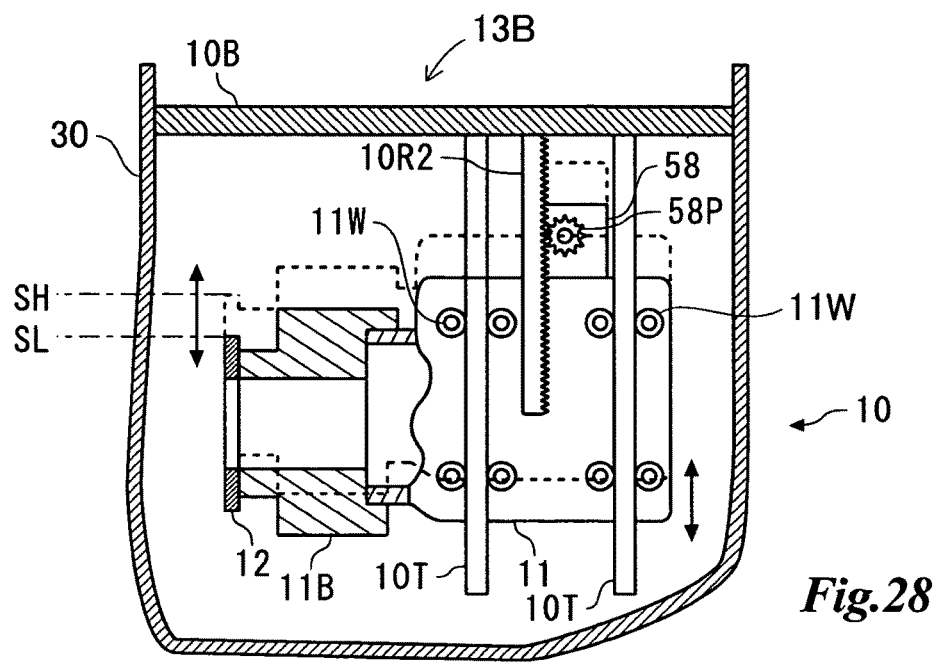
FIG. 28 is a partially broken view of other X-ray generating part.

FIG. 28 is a schematic diagram showing another structure of the fifth embodiment. The present embodiment is structured to slide and displace the X-ray generator 11 in the height direction.

A basic structure is explained. The base part 10B extending to the X-ray generating part 10 in the supporting member 30 has a pair of guide members 10T and 10T and a rack 10R2 which are suspended therefrom, and a plurality of rollers 11W . . . are arranged correspondingly in the X-ray generator 11, wherein each of the guide members 10T and 10T is sandwiched by these rollers 11W and a pinion 58P arranged in a rotary shaft of the motor 58 which is disposed in an upper space of a case of the X-ray generator 10 is engaged with the rack 10R2.

The radiation area restricting part 12 is also fixed to a front surface of the X-ray generator 11 via the hollow block 11B.

In such a structure, if the X-ray beam XB is irradiated on the object "O" and the motor 58 is driven to turn while rotating the supporting part 30, the pinion 58P is moved while being rotated on the rack 10R2 and the movement is also accompanied by sliding and moving the X-ray generator 11 inside the X-ray generating part 10 in the height direction.

In this embodiment, a mechanism including a combination of the guide member 11T, the roller 11W, the motor 58, the rack 10R2, the pinion 58P, the X-ray generator 11, the radiation area restricting part 12, and the block 11B constitutes the radiation area restricting part driving mechanism 13B.

According to such a structure of the present embodiment, it is unnecessary to move the supporting part 30 as a whole like the fourth embodiment, and moving only the X-ray generator 11 makes it possible to displace a radiation position of the X-ray beam XB relative to a radiography region of the object "O".

Note that, though it is not shown, as a modification of the fifth embodiment, it may also be structured to displace a radiation position of the X-ray beam XB in the height direction by moving only the X-ray generator 11 in the height direction relative to the radiation area restricting part 12 which is fixed to the supporting part 30 inside the X-ray generating part 10.

In addition, as for panoramic radiography, like the local X-ray CT apparatus according to Japanese Patent No. 3919048 which is an application of the present applicant, panoramic radiography may be realized by irradiating X-ray cone-beam on a virtual local region and extracting image data being a partial image obtained by ortho-X-ray cone-beam.

When such panoramic radiography using a virtual local region is executed, a rotary arm being the supporting part 30 can be rotated by maintaining a rotary center thereof in a fixed state.

In this case, the rotary center of the rotary arm is arranged in the vicinity of a central center of the dental arch S (or in an appropriate position between the dental arch S and the cervical vertebra on the bilaterally symmetric axis line of the dental arch S), and X-ray radiation using X-ray cone-beam is performed on the virtual local region which is around the rotary center, in order to use partial components of the radiation by the X-ray beam XB to generate a panoramic X-ray image. Also, when the X-ray cone-beam is irradiated, out of the irradiated X-ray cone-beam, components required for a panoramic X-ray image may be exclusively irradiated on the object "O" by restricting the radiation in the scanning direction using a slit and collimator or the like and displacing a restriction position in accordance with the scanning direction of the X-ray beam XB.

<Sixth Embodiment>

An embodiment for designating a local region being a radiography object is explained hereinafter.

This embodiment relates to designation of the local region and therefore the above-mentioned first to fifth embodiments can be applied appropriately.

An example using a dental arch illustration is explained first.

Figure 29:
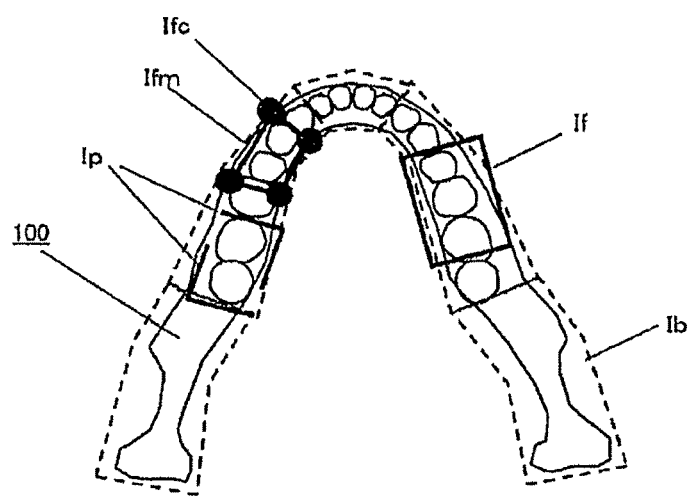
FIG. 29 is an example of illustration of a dental arch.

A dental arch illustration 100 as shown in FIG. 29 is displayed on a displaying part 67. Note that an illustration to be displayed is not limited to be two-dimensional as shown in FIG. 29 and may be three-dimensional. Considered as an example of three-dimensional display is to generate three-dimensional image data of three-dimensional dental arches of upper and lower teeth, which is seen in so-called computer graphics and the like, and display it in, for example, an oblique view or turning display by adding operations. The interested area "r" is specified by looking at the displaying part 67 on which the dental arch shown in FIG. 29 is displayed, and designating a position of an object region using the operating part 66 with operations such as, for example, moving, expanding and reducing a frame If in the figure which is displayed by being superposed on the dental arch illustration 100. Note that, in a three-dimensional illustration, the interested area "r" is also displayed by a three-dimensional semitransparent cube and the like.

Although the interested area "r" is displayed by the frame If in FIG. 29, the interested area "r" may also be held and surrounded by two hook-shaped indicators Ip which oppose to each other in the figure, or the interested area "r" may also be surrounded by a movable frame Ifm which is deformed freely by dragging a corner Ic using a pointer as shown in the figure.

The shape of the frames is not limited to a rectangle and various shapes such as circle, triangle and polygon equal to or more than pentagon can be considered.

There may also be other display methods such that, when the center of the interested area "r" is displayed by a crisscross, an area in the vicinity thereof is designated automatically.

A method to select and designate a desired block out of a plurality of blocks Ib predetermined as shown in a broken line may also be employed.

If the interested area "r" is specified as shown in FIG. 29, panoramic radiography is executed for the interested area "r" by a control made in the above-mentioned main control part 61 or other controls.

An image used for specifying an area, which is displayed on the screen of the displaying part 67, may be an image obtained by illustrating the object "O" like the dental arch illustration 100 as shown in FIG. 29, or as long as a position is set appropriately, an image obtained by taking an actual picture of the object "O" using a camera which photographs normal visible light may also be used instead of illustrations.

An example using a schematic illustration is explained next.

Figure 30A:
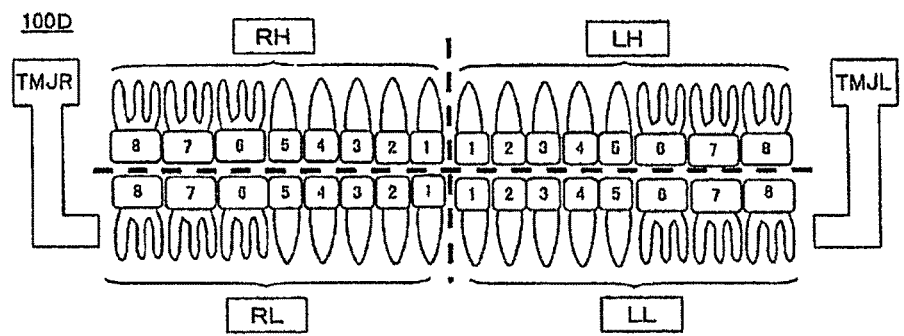
FIG. 30a and FIG. 30b are other examples of illustration of a dental arch.
Figure 30B:
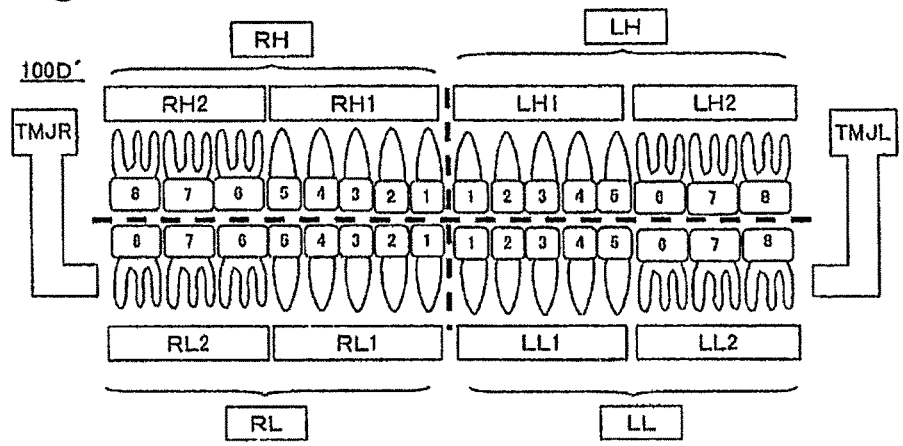

The illustration, which may be in a practical shape, may also be an image like a schematic illustration 100D as shown in FIG. 30*a* and FIG. 30*b*.

In FIG. 30*a*, a range from the front teeth to the molars on the right side of the upper jaw is displayed as an RH group including first to eighth teeth, a range from the front teeth to the molars on the left side of the upper jaw is displayed as an LH group including first to eighth teeth, a range from the front teeth to the molars on the right side of the lower jaw is displayed as an RL group including first to eighth teeth, and a range from the front teeth to the molars on the left side of the lower jaw is displayed as an LL group including first to eighth teeth.

In FIG. 30*a*, TMJR refers to the jaw joint on the right side and TMJL refers to the jaw joint on the right side. The RL group and the LL group are in a symmetrical relationship to the RH group and the LH group, respectively, across an occlusal surface, while the LH group and the LL group are in a symmetrical relationship to the RH group and the RL group, respectively, across a plane including a median line. TMJR and TMJL are also in a symmetrical relationship to each other across the plane including the median line.

In order to specify a region, for example, an applicable area may be touched and specified using the displaying part 67 as a touch panel, or it may be specified by moving a pointer displayed on the screen of the displaying part 67 with a mouse and the like, or if it is desired to specify an upper right first image for example, a number displayed in the image may be inputted with a keyboard like "RH8". In addition, an entire group may also be set as a radiography object by designating anywhere in the group or the range may be freely specified.

For example, in the case of using the displaying part 67 as a touch panel, by touching teeth like tracing with a finger from a tooth to another tooth, teeth included in the range can be controlled to be a radiography object.

For specifying the range, a structure to divide a range into zones to allow zone specification as shown in FIG. 30*b* can also be considered. In the example shown in the figure, a schematic image such as an illustration 100D' which is similar to the illustration 100D of FIG. 30*a* is divided into zones including RH1 for a zone more adjacent to the first to fifth front teeth in the RH group, and RH2 for a zone of the sixth to eighth molars therein. Similarly, a zone more adjacent to the first to fifth front teeth in the LH group is set to LH1, a zone of the sixth to eighth molars in the LH group is set to LH2, a zone more adjacent to the first to fifth front teeth in the RL group is set to RL1, a zone of the sixth to eighth molars in the RL group is set to RL2, a zone more adjacent to the first to fifth front teeth in the LL group is set to LL1, and a zone of the sixth to eighth molars in the LL group is set to LL2.

For example, if the displaying part 67 is used as a touch panel, it is structured so that a touch on a frame portion of "RH2" shown in FIG. 30*b* is followed by specifying a range containing the sixth to eighth teeth in RH2 as a radiography object.

It may also be structured to simply specify a group such as RH group, LH group, RL group and LL group. As for such an example, if the displaying part 67 is used as a touch panel, a structure is considered in such that touching a frame portion of "RH" shown in FIGS. 30a and 30b is followed by specifying a range containing the entire front to eighth teeth in the RH group as an object of computed tomography.

A frame may also be prepared in advance so that a desired range is contained within the frame on the displaying part 67 by moving the frame for range specification.

In addition, as an image displayed on the screen of the displaying part 67 for specifying the area, an image taken by radiography of the object "O" may also be used.

Figure 31A:
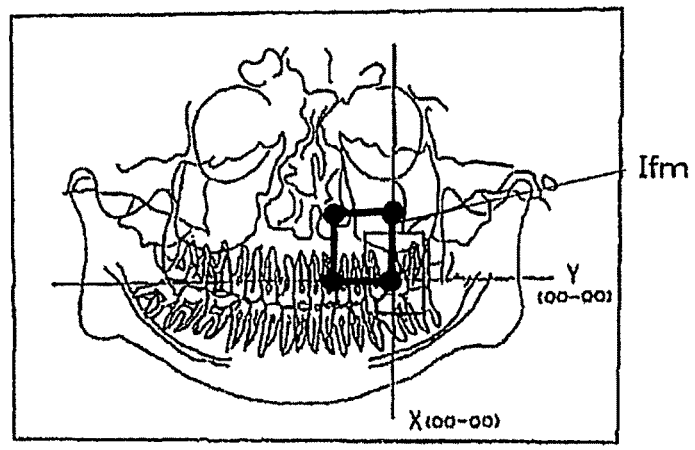
FIG. 31a is an example of position designation using a panoramic X-ray image and FIG. 31b is an example of position designation using a transmitted X-ray image.

For example, there is considered an example in which, as mentioned later, a panoramic X-ray image taken by panoramic radiography of the object "O" like a panoramic X-ray image 200 shown in FIG. 31a is displayed for specifying position.

Various kinds of frames and indicators as explained in FIG. 29 may also be displayed and used in a panoramic X-ray image of FIG. 31a by displaying, for example, a movable frame Ifm which is the same as the variable frame Ifm explained in FIG. 29 or the like.

As the medical examination which is often practiced in the dental surgery, panoramic radiography is executed once in the initial medical examination, followed by executing radiography again after the treatment. In this case, by using a panoramic X-ray image taken in the initial medical examination for specifying the position, only a treated region can be subjected to partial panoramic radiography after the treatment.

Figure 31B:
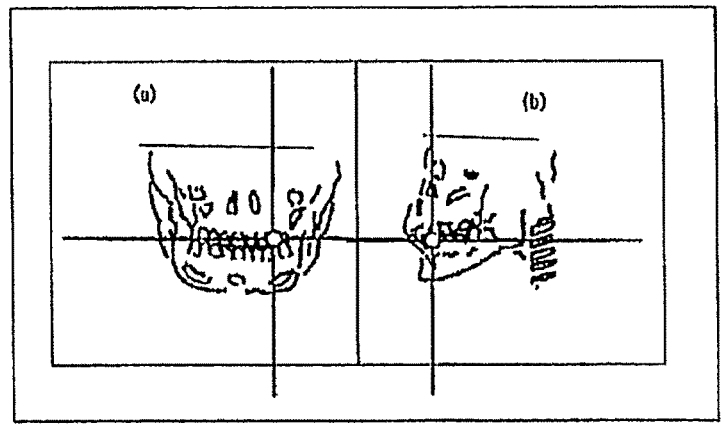

As shown in FIG. 31b, there are considered examples such as executing computed tomography for a target region by taking X-ray fluoroscopic images of the object "O" from different angles, displaying the X-ray fluoroscopic images obtained per angle, and specifying a target position on the displayed fluoroscopic images.

As an example of FIG. 31, it is possible to apply, for example, Japanese patent publication WO2006/209808, which is an application of the present applicant, appropriately.

Although the example of displaying a schematic illustration is mentioned above for FIGS. 30a and 30b, a structure considered as an example of direct specification of a region without displaying an image for area specification on the screen is to specify a position by arranging a plurality of bottoms in the illustration which is displayed in a three-dimensional shape and arrangement.

It is possible among the embodiments to apply the above-mentioned method to specify each tooth, specify a range, and specify each divided group or the like to each other appropriately.

In order to obtain an X-ray image according to the present invention, it is necessary to specify, first of all, a radiography region of the object "O" and control the displacement of the opening 12S hole and the supporting part 30 as mentioned above depending on the region.

Since different radiography regions of the object "O" are expected depending on the purpose of radiography and individual differences of the subject, it is desirable that a radiography region can be prepared easily before execution of radiography.

To meet such a demand, a camera device may be provided to take an image of the object "O" so that a radiography region can be specified from the taken image.

Figure 32:
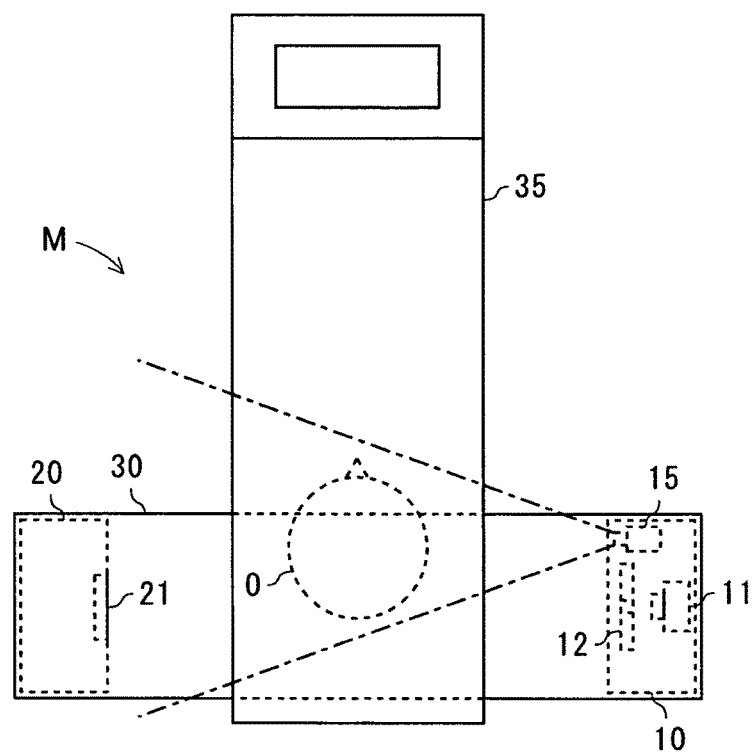
FIG. 32 is a diagrammatic plan view (seen from the side of object to be examined) of the medical X-ray apparatus of the present invention having a camera device.
Figure 33:
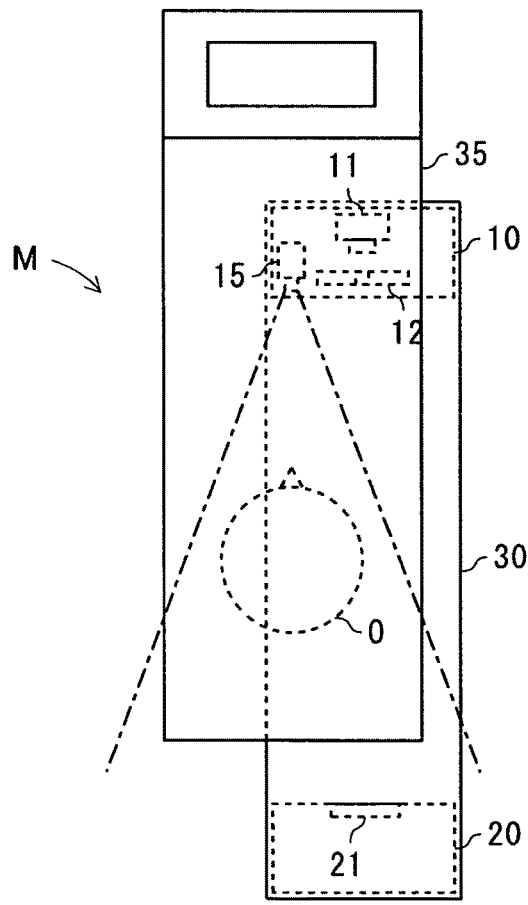
FIG. 33 is a diagrammatic plan view (seen from the front of object to be examined) of the medical X-ray apparatus of the present invention having a camera device.

FIGS. 32 and 33 show that the medical X-ray apparatus M, MA, MB is provided with a camera device 15 which takes an image by using visible light ray, wherein, based on the image taken by the camera device 15, a radiography region is set for panoramic radiography.

The camera device 15 is composed of a digital camera provided with a CCD sensor or a CMOS sensor as an image sensor, and takes images of the front surface and the side surface of the object "O".

Image data of the object "O" taken by the camera device 15 is taken into the image processing part 70 and displayed in the display part 76, so that an operator operates the operating part 75 while looking at the image data and specifies a radiography region.

Figure 34A:
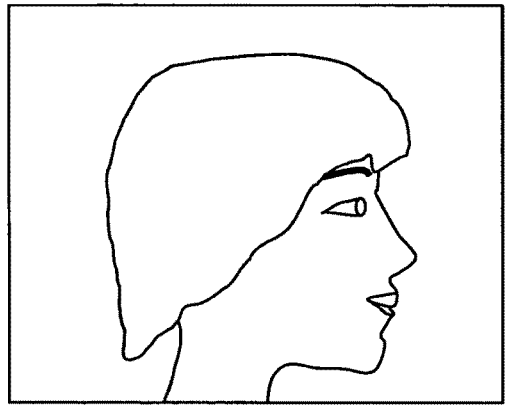
FIG. 34 is a view explaining the basic principle of image process for setting an X-ray radiation area.

When an image of the temporal of the object "O" is taken by a camera device 12, the display part 76 of the image processing part 70 displays, for example, a whole image of the temporal of the object "O" as shown in FIG. 34a, so that an operator is allowed to specify a radiography region by operating a pointing device or other devices, while looking at the whole image of the temporal.

When the radiography region is thus specified by the operator, the main controlling part 61 executes a predetermined arithmetic process and calculates, at the time of scanning with the X-ray beam XB, according to the specified radiography region, necessary control data in order for the opening 12S and the supporting part 30 to control a radiation position of the X-ray beam XB.

FIG. 34 conceptually shows the point of how a radiography region is specified automatically from an image of the temporal of the object "O" taken by the camera device.

Figure 34B:
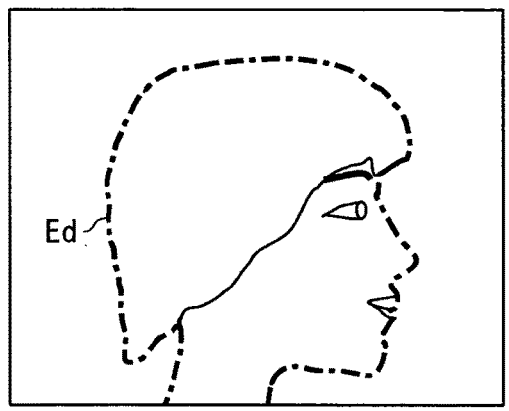

When an image of the object "O" as shown in FIG. 34a, which was taken by the camera device 12, is inputted to an image processing part 73, the image processing part 73 detects a contour line Ed of the entire temporal area of the object "O" as shown in FIG. 34b.

This contour line Ed is detected, for example, based on a variable amount such as differential value of a data amount between pixels, by a contour detection method for detecting a contour portion in an image.

Figure 34C:
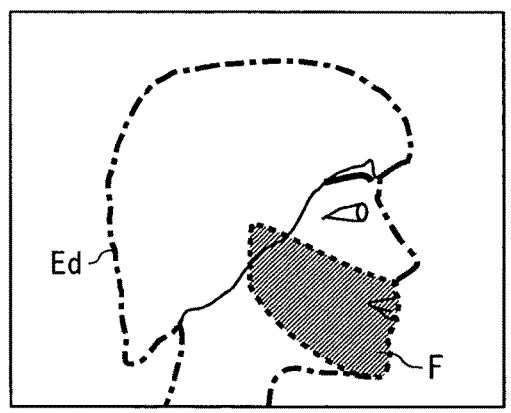

Then, after detecting the contour line Ed of the entire temporal area of the object "O", the main controlling part 61 obtains a radiography region corresponding to each position of the contour line Ed by operation, followed by determining a radiography region F in the temporal of the object "O" as shown in FIG. 34c.

For example, in accordance with the detected contour line Ed, each radiography region F such as the head, forehead, eye, nose, mouth, jaw and neck of the object "O" is determined.

After the main controlling part 61 estimates, based on each radiography region F which was thus determined, an area in which the upper and lower jaw bones are located with respect to an area surrounded by the contour line Ed, the main controlling part 61 causes the scan orbit setting part 61a to set a scan orbit and causes the radiation area setting part 61b to move the opening 12S and the supporting part 30 in order to set control data required to control a radiation position of the X-ray beam XB to fall in a radiography area.

Resulting from determination of the radiography region F, the main controlling part 61 calculates and prepares a control parameter used to control a height position of the opening 12S or the opening 12S relative to a rotary angle of the supporting part 30.

The radiography region F, which is thus determined, may also be partially modified or partially expanded or reduced by an operator who operates the operating part 66, while the radiography region F is displayed in the displaying part 67 together with an image taken by the camera device 15.

The camera device 12 may also take an image of the front surface of the object "O" or take images of the front surface and side surface thereof in combination in order to specify a radiography area of the object "O".

In this case, as shown in FIG. 33, the supporting part 30 is driven by the scan driving part 50, and the position of the camera device 15 is determined to a position, in front of the object "O", in which an image of the entire face surface of the object "O" can be taken. Then, similar to the case of capturing an image of the temporal of the object "O", the camera device 15 takes an image of the face surface of the object "O" by visible light ray and outputs image data thereof to the main controlling part 61.

Figure 35:
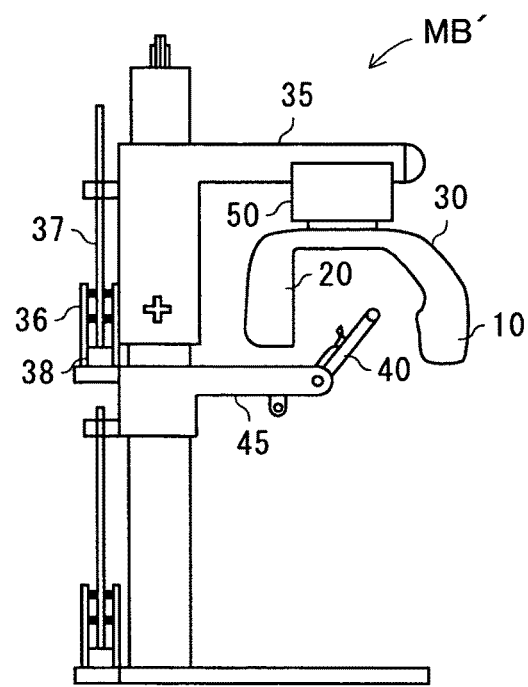
FIG. 35 shows the diagrammatic structure of other medical X-ray apparatus according to the present invention.

A plurality of the camera devices 15 may also be arranged to take images of the object "O" from a plurality of different directions at once. At this time, other than the camera device 15 provided in the X-ray detecting part 10, for example, a camera device may also be arranged in the lifting means for supporting the supporting part 30 as shown in FIG. 35.

Figure 36:
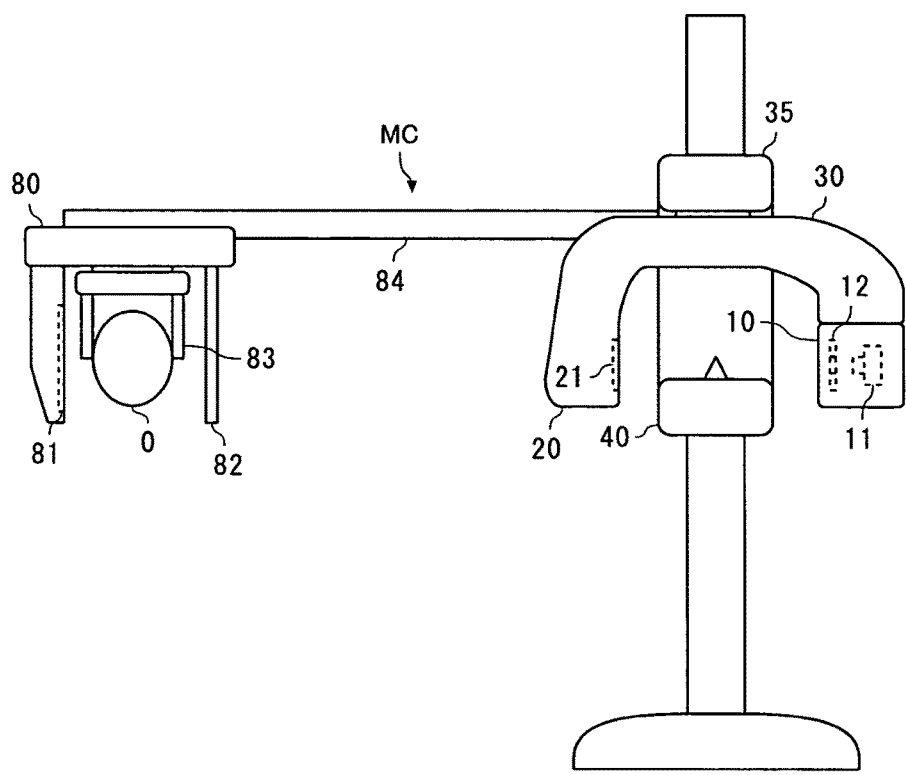
FIG. 36 is a side view of the medical X-ray apparatus of the present invention which can be also used for cephalometric radiography and panoramic radiography.

The above-mentioned camera device 15 can be, similar to the case of panoramic radiography, applied to the case of cephalometric radiography like a medical X-ray apparatus MC as shown in FIG. 36 which is mentioned later.

Cephalometric radiography is explained.

Figure 37:
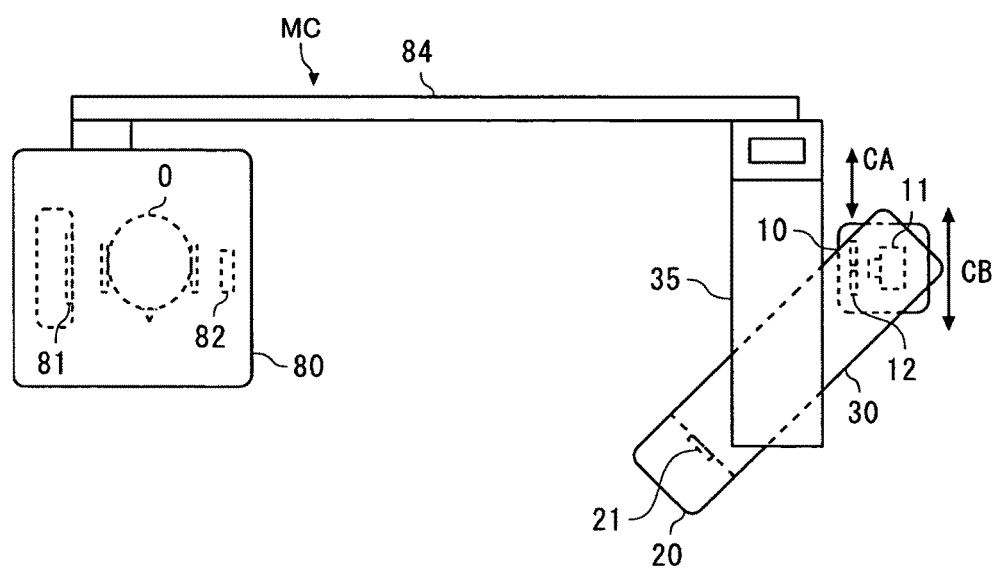
FIG. 37 is a plan view of the medical X-ray apparatus of the present invention which can be also used for cephalometric radiography and panoramic radiography.

FIG. 36 and FIG. 37 show the medical X-ray apparatus MC used for both panoramic radiography and cephalometric radiography.

In this medical X-ray apparatus MC, a fixed arm 84 is extended from the lifting arm 35 being the lifting means which pivots the supporting part 30 and is lifted along a column, and the object holding part 80 is arranged on the top end of the fixed arm 84.

The supporting part 30 is rotatably attached to the lifting arm 35 and provided with the X-ray generating part 10 in one end and the X-ray detecting part 20 in the other end, wherein the X-ray generator 11 is arranged in the X-ray generating part 10 and the X-ray detector 21 is arranged in the X-ray detecting part 20, so that the object "O", which is held between the X-ray generating part 10 and the X-ray detecting part 20, is rotated for panoramic radiography.

The X-ray generating part 10 provided in one end of the supporting part 30 is also turnable itself, whereby a radiation direction of the X-ray beam XB can be moved and set to a position corresponding to a radiography mode.

On the other hand, head fixing means 83 for fixing the head of the object "O" is suspended from and supported by the object holding part 80 which includes an X-ray detector 81 and a radiation area restricting part 82 serving as a second slit. The X-ray detector 81 and the second radiation area restricting part 82 are provided for cephalometric radiography.

Because the X-ray generator 11 provided in the supporting part 30 is shared in cephalometric radiography, the supporting part 30 is directed to a direction oblique to the main body lifting part 30 and the X-ray generating part 10 is further faced to oppose the object holding part 80, as shown in FIG. 37, in order to irradiate the X-ray beam XB on the object "O" for scanning in a state that the X-ray detecting part 20 of the supporting part 30 is not positioned on a path of the X-ray beam XB which is irradiated from the X-ray generator 11 and received in the X-ray detector 81, or in a state that the angle of the supporting part 30 is set to prevent the X-ray detector 20 from disturbing the X-ray beam XB irradiated for cephalometric radiography. Scan movement is achieved by synchronization of the radiation area restricting part 12 such as, for example, a slit plate in front of the X-ray generator 11 fixed in the X-ray generating part 10, the X-ray detector 81 and the radiation area restricting part 82 with respect to the scanning direction.

To these structures, the structure of the medical X-ray apparatus M proposed and disclosed in Japanese patent publication JP-2002-17718-A, which is an application of the present applicant, can be applied appropriately.

Then, the X-ray beam XB emitted from the X-ray generating part 10 is irradiated on the object "O", and the X-ray detector 81 carries out a radiography operation corresponding to the scanning timing of the X-ray beam XB and transmits generated image data to the main body controlling part 60 sequentially. Image data which was thus received by the main body controlling part 60 is transmitted to the image processing part 70 sequentially in order to generate image data serving as a sheet of a cephalometric image.

Figure 39A:
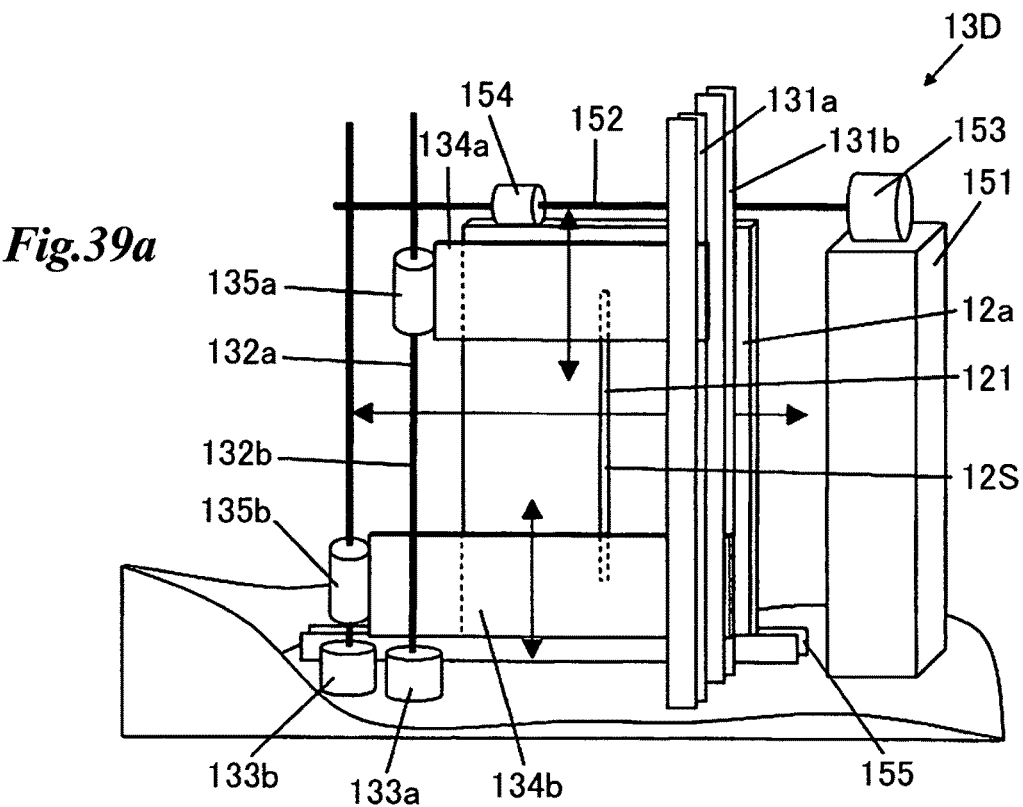
FIG. 39a is a perspective view of a radiation area restricting part driving mechanism and FIG. 39b is a perspective view of a slit member.
Figure 39B:
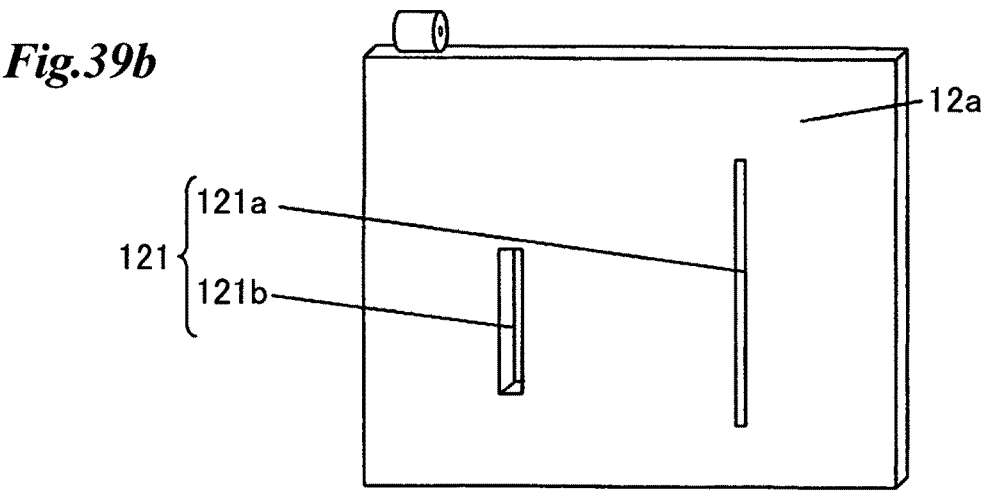

FIG. 39a shows an example of a radiation area restricting part driving mechanism 13D which constitutes the X-ray radiation position changing part A in the medical X-ray apparatus 37 shown in FIG. 36 and FIG. 37.

The radiation area restricting part driving mechanism 13D has a structure which is basically the same as that of the radiation area restricting part driving mechanism 13C shown in FIG. 15a, but the only difference is the slit member 12a which is designed to be movable in the scanning direction. Characteristic features are such that a female screw part 154 formed with a screw groove is provided in the upper end of the slit member 12a and the female screw part 154 is screwed through and penetrated into a rotary shaft 152, which is formed with a screw thread, of a motor 153 fixed on a motor fixing stand 151 which is fixed and arranged on the same base used to fix the motors 133a and 133b. The slit member 12a is fitted into a guide groove 155 in the lower end and can be displaced in the scanning direction by driving the motor 153. It is because the opening 12S is moved in the scanning direction, in front of the X-ray generator 11, for scanning in cephalometric radiography.

Figure 38:
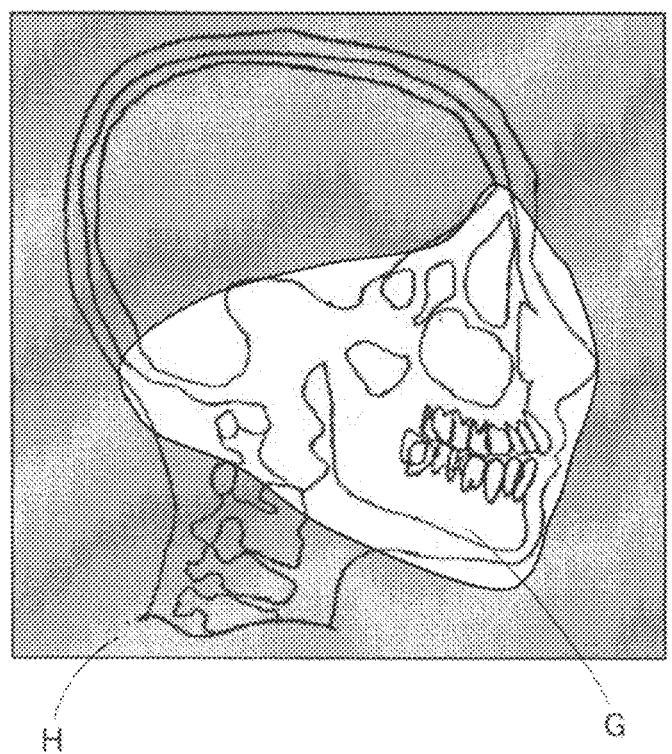
FIG. 38 is a view explaining the concept of cephalometric image.

FIG. 38 explains the concept of the cephalometric image.

An area which contributes to the medical examination as an image in cephalometric radiography is a portion shown by G in FIG. 38, and a shaded portion H corresponds to an area which is desired to avoid the X-ray exposure and does not contribute to medical examination.

Namely, a radiography region of the object "O" has a narrow area width in the height direction on the occipital side of a subject, and a wide area width in the height direction on the face side.

According to the present invention, owing to the above-mentioned principle, the X-ray beam XB can be irradiated by restricting it to a radiography region, so that irradiation of the X-ray beam XB on the shaded portion H shown in FIG. 38 can be cut off.

Also, in the medical X-ray apparatus MC which enables such cephalometric radiography, a radiation area of the X-ray beam XB to scan the object "O" can be restricted by the radiation area restricting part 12 in the X-ray generating part 10, so that the radiation area restricting part 82 in the object holding part 80 may be removed from the structure.

Even in the case of using the structure provided with the radiation area restricting part 82 or the like, the height position and the opening 12S in the radiation area restricting part 82 may be designed to be changeable along the scanning direction of the X-ray beam XB so as to restrict, corresponding to a radiography objective area, X-ray irradiation on the object "O" by the radiation area restricting part 82.

As mentioned above, similar to the case of panoramic radiography, the camera device 15 shown in FIG. 32 and FIG. 33 can be applied to the case of cephalometric radiography like the medical X-ray apparatus MC. The camera device 15 may be provided in optional two places of the medical X-ray apparatus MC to take images of the object "O" from a plurality of angles, or to take images of the object "O" from a plurality of angles while rotating the supporting part 30. Moreover, in cephalometric radiography, in the stage of FIG. 34c, a radiography region G of FIG. 38 is recognized in place of the radiography region F.

The radiation area restricting part driving mechanism 13D of FIG. 39a can be used for both panoramic radiography and cephalometric radiography.

The slit member 12a of the radiation area restricting part driving mechanism 13D may be further deformed and applied to arrange a panoramic radiography exclusive opening 121a and a cephalometric radiography exclusive opening 121b in the slit member 12a as shown in FIG. 39D, wherein the panoramic radiography exclusive opening 12a is selectively arranged in panoramic radiography and the cephalometric radiography exclusive opening 121b is selectively arranged in cephalometric radiograph in front of the X-ray generator 11.

Each of the openings can be easily selected by driving the motor 153.

The X-ray detector 81 may be provided in such that, as mentioned above, the X-ray detector 81 in the scanning direction is designed to have a width which is substantially equivalent to the width of the slit X-ray beam XB to be received, and move in synchronization with the scanning with the slit X-ray beam XB, or it may be made of a large-sized X-ray detector having a detection surface which allows radiation of the entire head and the X-ray detector 81 is fixed so that the slit X-ray beam for scanning the object "O" is received in a part of the detection surface.

In addition, as for the scanning with the X-ray beam XB emitted from the X-ray generator 11, it may be realized by agitating the radiation area restricting part 12 in front of the X-ray generator 11, which is fixed as mentioned above, in the scanning direction relative to the X-ray generator 11 or by using the XY table 53 to move the supporting part 30 as a whole in the scanning direction.

The invention claimed is:

1. A medical X-ray apparatus comprising
    a supporting part for supporting an X-ray generator and a two-dimensional X-ray detector while interposing a dental arch to be examined therebetween,
    a radiation area restricting part for restricting a radiation area of X-ray generated from said X-ray generator by restricting the X-ray to form a slit X-ray beam,
    a scan driving part for scanning said dental arch with the slit X-ray beam restricted by said radiation area restricting part in panoramic radiography, wherein
        a direction intersecting with an X-ray scan direction is defined as a height direction;
        said radiation area restricting part forms said slit X-ray beam extending in said height direction, and
        said radiation area restricting part comprises a slit with a top end and a bottom end, at least one of which is moveable in said height direction,
    a radiation area setting part for setting the radiation area,
    a mode switching part for switching between
        a partial panoramic radiography mode for executing a partial panoramic radiography wherein only a part of radiography objective area of panoramic radiography as a local area is set as the radiation area, and
        an entire panoramic radiography mode for executing an entire panoramic radiography wherein an entire radiography objective area of panoramic radiography is set as the radiation area, wherein
    said radiation area setting part sets the local area in said partial panoramic radiography mode,
        the local area is set so that the radiation area in the height direction and in said X-ray scan direction is more restricted than the radiation area in the entire panoramic radiography mode,
        an X-ray radiation range of the local area in the height direction is set by moving at least one of said top and bottom ends of said slit in said height direction by said radiation area restricting part at a desired position in accordance with a position of the local area,
        the X-ray radiation range of the local area in the scan direction is set so that said slit X-ray beam is permitted to let only the local area be radiated,
        a displaying part displays an image of the dental arch for specifying the local area, and
        an operating part receives an operation to the image of the dental arch to change the range of the radiation area in the height direction and in the scan direction in the partial panoramic radiography mode.

2. The medical X-ray apparatus as set forth in claim 1, wherein said radiation area setting part changes a position of at least one of said top and bottom ends of said slit in said height direction of said radiation area of X-ray while said slit X-ray beam is scanned.

3. The medical X-ray apparatus as set forth in claim 1, wherein said radiation area setting part sets as said radiation area for partial panoramic radiography only a tooth or teeth on an upper jaw or a tooth or teeth on a lower jaw as selected from the dental arch as used for said radiography objective area of panoramic radiography.

4. The medical X-ray apparatus as set forth in claim 1, wherein said X-ray generator irradiates said X-ray only when said slit X-ray beam passes through said radiation area for partial panoramic radiography.

5. The medical X-ray apparatus as set forth in claim 1,
    further comprising an X-ray generation controlling part for controlling a tube voltage and a tube current of said X-ray generator,
    wherein when said panoramic radiography including said partial panoramic radiography is executed, said X-ray generation controlling part controls at least one of the tube voltage and the tube current of said X-ray generator in conformity with an area of said dental arch where said slit X-ray beam is irradiated from said X-ray generator.

6. The medical X-ray apparatus as set forth in claim 1, further comprising a camera for taking a picture of said dental arch, wherein said radiation area setting part sets said radiation area of the X-ray of said dental arch based on the picture of said dental arch taken by said camera.

7. The medical X-ray apparatus as set forth in claim 1, further comprising an image processing part for producing a partial panoramic X-ray image of said radiation area of X-ray of said partial panoramic radiography in such a manner that X-ray transmitted images as frame images with respect to said dental arch detected on said two-dimensional X-ray detector are synthesized together to produce image data in a predetermined section of said dental arch, when said partial panoramic radiography is executed.

8. The medical X-ray apparatus as set forth in claim 7, wherein said image processing part produces a plurality of image data of a plurality of sectional planes from said frame images along a panoramic sectional plane, and the produced image data of the plurality of sectional planes are synthesized together.

9. The medical X-ray apparatus as set forth in claim 7, wherein said image processing part produces an X-ray image similar to a conventional intraoral radiography image processing an image data obtained by said panoramic radiography.

10. The medical X-ray apparatus as set forth in claim 1, wherein said radiation area setting part sets the radiation area so that a position of the top and bottom ends of said slit for irradiating a front teeth area is set lower than a position of the top and bottom ends of said slit for irradiating a jaw area in said height direction.

11. The medical X-ray apparatus as set forth in claim 1, wherein
said displaying part displays a movable frame on the image of the dental arch for specifying said local area, and
said operating part receives an operation to move a movable frame to change the range of the radiation area in the partial panoramic radiography mode.

12. A medical X-ray apparatus comprising:
a supporting part for supporting an X-ray generator and a two-dimensional X-ray detector while interposing a dental arch to be examined therebetween;
a radiation area restricting part for restricting a radiation area of an X-ray generated from the X-ray generator by restricting the X-ray to form a slit X-ray beam;
a scan driving part for scanning the dental arch with the slit X-ray beam restricted by the radiation area restricting part in panoramic radiography, wherein
a direction intersecting with an X-ray scan direction is defined as a height direction,
the radiation area restricting part forms the slit X-ray beam extending in the height direction, and
the radiation area restricting part comprises a slit with a top end and a bottom end, at least one of which is movable in the height direction;
a radiation area setting part for setting the radiation area, and
a mode switching part for switching between:
a partial panoramic radiography mode for executing a partial panoramic radiography in which only a part of a radiography objective area of panoramic radiography as a local area is set as the radiation area, and
an entire panoramic radiography mode for executing an entire panoramic radiography in which an entire radiography objective area of panoramic radiography is set as the radiation area, wherein
the radiation area setting part sets the local area in the partial panoramic radiography mode,
the local area is set so that the radiation area in the height direction and in the X-ray scan direction is more restricted than the radiation area in the entire panoramic radiography mode,
an X-ray radiation range of the local area in the height direction is set by moving at least one of the top and bottom ends of the slit in the height direction by the radiation area restricting part at a preset position in accordance with a position of the local area,
the X-ray radiation range of the local area in the scan direction is preset so that the slit X-ray beam is permitted to let only the local area be radiated,
a displaying part displays an image of the dental arch for specifying the local area, wherein the image of the dental arch is an image in which a curved area of the dent& arch is divided into a plurality of areas in accordance with the position of the local area, and
an operating part receives an operation to the image of the dental arch to select one of the plurality of areas in the partial panoramic radiography mode.

13. The medical X-ray apparatus as set forth in claim 12, wherein the displaying part displays a line of frames or a hook-shaped indicator for each of the plurality of areas in the partial panoramic radiography mode.

14. The medical X-ray apparatus as set forth in claim 12, wherein the radiation area setting part changes a position of at least one of the top and bottom ends of the slit in the height direction of the radiation area of X-ray while the slit X-ray beam is scanned.

15. The medical X-ray apparatus as set forth in claim 12, wherein the radiation area setting part sets as the radiation area for partial panoramic radiography only a tooth or teeth on an upper jaw or a tooth or teeth on a lower jaw as selected from the dental arch as used for said radiography objective area of panoramic radiography.

16. The medical X-ray apparatus as set forth in claim 12, wherein the X-ray generator irradiates the X-ray only when the slit X-ray beam passes through the radiation area for partial panoramic radiography.

17. The medical X-ray apparatus as set forth in claim 12, further comprising an X-ray generation controlling part for controlling a tube voltage and a tube current of the X-ray generator,
wherein when the panoramic radiography including the partial panoramic radiography is executed, the X-ray generation controlling part controls at least one of the tube voltage and the tube current of the X-ray generator in conformity with an area of the dental arch where the slit X-ray beam is irradiated from the X-ray generator.

18. The medical X-ray apparatus as set forth in claim 12, further comprising a camera for taking a picture of the dental arch, wherein the radiation area setting part sets the radiation area of the X-ray of the dental arch based on the picture of the dental arch taken by the camera.

19. The medical X-ray apparatus as set forth in claim 12, further comprising an image processing part for producing a partial panoramic X-ray image of the radiation area of X-ray of the partial panoramic radiography in such a manner that X-ray transmitted images as frame images with respect to the dental arch detected on the two-dimensional X-ray detector are synthesized together to produce image data in a predetermined section of the dental arch, when said partial panoramic radiography is executed.

20. The medical X-ray apparatus as set forth in claim 19, wherein the image processing part produces a plurality of image data of a plurality of sectional planes from the frame images along a panoramic sectional plane, and the produced image data of the plurality of sectional planes are synthesized together.

* * * * *